(12) United States Patent  (10) Patent No.: US 7,681,433 B2
Konno et al.  (45) Date of Patent: Mar. 23, 2010

(54) DETECTION SENSOR AND RESONATOR

(75) Inventors: Mitsuo Konno, Tsukuba (JP); Tsuyoshi Ikehara, Tsukuba (JP); Ryutaro Maeda, Tsukuba (JP); Takashi Mihara, Hachioji (JP)

(73) Assignees: National Institute of Advanced Industrial Science and Technology, Tokyo (JP); Olympus Corporation, Tokyo (JP)

( * ) Notice: Subject to any disclaimer, the term of this patent is extended or adjusted under 35 U.S.C. 154(b) by 675 days.

(21) Appl. No.: 11/441,829

(22) Filed: May 26, 2006

(65) Prior Publication Data

US 2007/0119232 A1  May 31, 2007

(30) Foreign Application Priority Data

May 30, 2005 (JP) ............................. 2005-157217
Jan. 11, 2006 (JP) ............................. 2006-004197
Mar. 17, 2006 (JP) ............................. 2006-073742

(51) Int. Cl.
*G01N 29/02* (2006.01)

(52) U.S. Cl. ................................... 73/24.06

(58) Field of Classification Search ............... 73/24.06, 73/570, 579, 649, 652, 662, 73
See application file for complete search history.

(56) References Cited

U.S. PATENT DOCUMENTS

| 5,705,399 | A * | 1/1998 | Larue ........................ 436/501 |
| 5,852,229 | A * | 12/1998 | Josse et al. ................ 73/24.06 |
| 6,457,361 | B1 * | 10/2002 | Takeuchi et al. ............. 73/580 |
| 6,805,009 | B2 * | 10/2004 | Burdess et al. ............... 73/579 |
| 6,964,196 | B2 * | 11/2005 | Turner et al. ................ 73/580 |
| 6,997,039 | B2 * | 2/2006 | Rao et al. ................. 73/24.06 |
| 2004/0194548 | A1 * | 10/2004 | Dayagi et al. ............... 73/580 |
| 2006/0254362 | A1 * | 11/2006 | Luharuka et al. ............. 73/649 |
| 2007/0028668 | A1 * | 2/2007 | Goto et al. ................ 73/24.06 |
| 2007/0119232 | A1 * | 5/2007 | Konno et al. ............... 73/24.01 |

* cited by examiner

*Primary Examiner*—John Fitzgerald
(74) *Attorney, Agent, or Firm*—Hogan & Hartson LLP

(57) ABSTRACT

By using a disc type resonator, a sensor detects a substance having a mass and the mass with high sensitivity. Moreover, it is preferable to detect a change in vibrations of a substance attached or adsorbed to an area having a vibration amplitude equal to or larger than a constant value. This disc type resonator can be fabricated by the MEMS technique by using single-crystal or polycrystalline Si as a structural material. To improve the attachment efficiency of molecules and the like to be detected, irregularity or a groove is preferably provided on the surface of the disc type resonator.

21 Claims, 44 Drawing Sheets

$n=0\ (\varpi=0),\ m=1$ $n=0\ (\varpi=0),\ m=2$ $n=0\ (\varpi=0),\ m=3$ $n=0\ (\varpi=0),\ m=4$ $n=0$ ($\Delta=0$), $m=1$ $n=0$ ($\Delta=0$), $m=2$ $n=0$ ($\Delta=0$), $m=3$ $n=0$ ($\Delta=0$), $m=4$ U(Rb) ———
U(Ra) ----------
V(Rb) —·—·—
V(Ra) ——

U(Rb) ———
U(Ra) --------
V(Rb) —·—·—
V(Ra) ▬▬▬

U(Rb) ————
U(Ra) - - - - - - -
V(Rb) —·—·—·—
V(Ra) ——————

DETECTION SENSOR AND RESONATOR

BACKGROUND OF THE INVENTION

1. Field of the Invention

The present invention relates to a detection sensor and a resonator preferably used to detect presence or absence of a substance having a mass and the mass of the substance.

2. Description of the Related Art

In accordance with the progress of the microfabrication technique such as the micromachine/MEMS (Micro Electro Mechanical Systems) technique, a mechanical resonator with a very small size has been obtainable. Thereby, the mass of the resonator itself can be decreased, and a high-sensitivity resonator is being realized in which frequency or impedance characteristics are fluctuated by a mass change due to attachment of a very small substance (such as molecule or virus) at a molecule level. Use of this high-sensitivity resonator makes it possible to constitute a sensor capable of detecting presence and quantity of a very small substance. That is, because the size of the resonator is greatly decreased, the frequency of the resonator is increased up to GHz level and moreover, Si can be used as the material of the resonator. Therefore, the study aiming at integration with a semiconductor circuit is being progressed.

Moreover, by using the way of generating vibration (vibration mode) having a small vibration energy loss due to air viscosity or the like, it is possible to cause the resonator to generate the vibration having a very high Q value (Quality Factor) even in air and accurate observation of the frequency fluctuation has been achievable.

As an apparatus for detecting the quantity of a substance based on the frequency change of a resonator, a QCM (Quartz Crystal Microbalance) sensor is known. This uses the property of a vibration frequency fluctuating (or lowering) depending on the mass of a substance when the substance attaches to a quartz resonator. The QCM sensor has a superior performance as a mass sensor for measuring a very small mass change. For example, the QCM sensor is frequently used as a thickness meter (vapor deposition monitor) (for example, refer to Non-patent Document 1: WHAT IS A QUARTZ CRYSTAL MICROBALANCE—QCM, Internet<URL: http://www.pharmaceutical-int.com/categories/qcm-technolo gy/what-is-a-quartz-crystal-microbalance-qcm.asp>).

Moreover, a technique has also been proposed which measures a mass change of a lipid bilayer formed on the surface of a quartz resonator by allowing molecules for providing a gustatory sense or olfactory sense to be adsorbed by the bilayer (for example, refer to Non-patent Document 2: Ikuo Okabatake, "To measure gustatory sense or olfactory sense by weight", Analysis, The Japan Society for Analytical Chemistry, 2003, No. 10, pp. 606-609).

By using this system, it has been already reported that a hydrogen-gas detection sensor to which platinum or palladium is applied as a hydrogen-molecule adsorption film or alcohol component detection using a PMMA polymer or food smell detection can be realized.

However, in the case of the sensor using a resonator whose vibration characteristic is changed due to attachment of above-described very-small mass, there is always a demand for sensors of more sensitive, more compact, and lower in cost.

Moreover, in the case of the technique described in Non-patent Document 2, a lipid bilayer having a high adsorption property of molecules has been used. However, this bilayer indispensably requires moisture and the use thereof in a dry atmosphere is subjected to restrictions. Moreover, there are problems that it is difficult to freely micro-fabricate quartz and integrate the quartz with silicon. Because of these reasons, further ingenuity is necessary to improve the sensitivity.

In the case of a QCM sensor, a vibration frequency is shown by the following expression.

$$f_o = \alpha/t$$

In the expression, $\alpha$ denotes a constant for determining a frequency and t denotes the thickness of a quartz resonator.

Thus, because the vibration frequency of the QCM sensor is inversely proportional with the quartz resonator thickness, it is impossible to sufficiently decrease the thickness. This means that increase of the ratio between a very small mass to be detected and the effective mass of a resonator is limited in the QCM sensor.

Moreover, when constituting a sensor for detecting the mass of a substance and when other substance other than a substance of interest attaches to a resonator, detection accuracy is deteriorated. Therefore, there is a demand for sensor capable of performing high-accuracy detection independently of an environment in which the sensor is used.

The present invention is made in light of the above technical problems and its object is to provide a detection sensor with high sensitivity, small size, low price, and high accuracy.

SUMMARY OF THE INVENTION

To achieve the above object, a detection sensor of the present invention is provided with a disc type resonator whose vibration characteristic is changed by attachment or adsorption of a substance having a mass, a driving unit for vibrating the resonator, and a detection unit for detecting a substance by detecting the change in vibrations in the resonator.

In this case, it is also allowed that the substance attaches to the surface of the resonator. In addition, the resonator may be provided with an adsorption member for adsorbing the substance. In this case, it is possible to separate the adsorption member from the resonator or set the adsorption member integrally with the resonator.

In the case of the detection sensor, when a substance having a mass attaches to the resonator, the vibration characteristic of the resonator such as the number of vibrations due to the mass changes. Therefore, the detection unit can detect the substance by electrically monitoring the vibration of the resonator. In this case, detection of a substance encompasses not only detecting presence or absence of attachment of the substance but also detecting the quantity of the substance attached to the resonator. Thereby, it is possible to realize a disc type detection sensor which is not ever present.

The driving unit and detection unit may use any means in order to detect the vibration of the resonator and the change in vibrations, however, use of electrostatic coupling with the resonator is preferable.

Moreover, it is allowed to add an adsorption material capable of efficiently adsorbing molecules to the substance (molecule) attachment face of the resonator. The adsorption material includes global recognition materials and selective recognition materials. The global recognition materials are polymers for adsorbing certain molecule groups such as alcohol and ether though the selectivity is not strong. It is also effective to increase the surface area by changing these polymers to nanofiber state or porous state. Also, as recognition material having strong selectivity, there are a material derived from organism which causes an antigen-antibody reaction, combination of acceptor and receptor, and probe or the like having a particular base sequence for causing hybridization with gene, DNA, or RNA. Moreover, it is allowed to use a lipid bilayer. This absorption material is normally formed separately from the resonator and set to the surface of the resonator in general. However, when the adsorption material has a density of a certain extent, the adsorption material and the resonator may be integrally formed. In addition, it is allowed to form the resonator itself of the adsorption material.

Furthermore, nanofiberization of a polymer denotes changing the polymer to fiber having a size (length) of several nanometers to several hundreds of micrometers in order to dramatically improve the adsorption performance of polymers having different adsorption characteristics with respect to various molecules.

Furthermore, it is preferable to form irregularity or groove on at least a part of the surface of the resonator. Thereby, the surface area of the resonator increases and a substance efficiently attaches to the surface of the resonator. Moreover, in combination with nanofiberization of the above-described adsorption material, the sensitivity can be further improved.

As a substance to be detected, this detection sensor may employ a specific molecule or a plurality of kinds of molecules having a specific characteristic or feature. Thereby, it is possible to use the detection sensor for a gas detection sensor and smell sensor or the like. When the resonator is intended for the specific molecule such as gas, molecule derived from organism, floating molecule in a life space, or volatile molecule, it is preferable to detect only a specific kind of a molecule with high selectivity. Moreover, with use of a plurality of detection sensors having a high selectivity, it is possible to recognize a plurality of kinds of molecules or broaden the use application. Furthermore, molecule groups such having a specific feature referred to as global recognition and such having the same side chain are also detectable. In this case, by using a plurality of detection sensors, it is also allowed to recognize a molecule group by signal processing or processing using software in accordance with the difference of detection performance between these detection sensors. Moreover, it is allowed to detect specific protein, enzyme, and sugar chain by changing a configuration as to operate in liquid.

Furthermore, a detection sensor of the present invention makes it possible to realize a configuration in which a plurality of the resonators are provided and one resonator electrostatically couples with the other resonator. In this case, a detection unit detects attachment of a substance to a resonator by detecting the change in the difference between vibration frequencies when a substance attaches to one resonator and the other resonator. Thus, one resonator and the other resonator vibrate in reverse phase from each other by electrostatic coupling. Therefore, the change in the difference between vibration frequencies due to attachment of the substance are output in accordance with a low-frequency signal and detection becomes easy.

Furthermore, by setting a reference resonator to which a substance does not attach in parallel with a resonator and detecting the change in vibrations of a resonator on the basis of the vibration of the reference resonator when a substance attaches to the resonator, the detection unit can detect attachment of a substance to the resonator. By setting the resonator to which the substance attaches and the reference resonator to which the substance does not attach under the same detection environment, the detection unit can perform high-sensitivity detection without being influenced by disturbance.

In the case of this resonator and reference resonator, by connecting the resonator with the reference resonator so that reverse-phase vibration occurs, it is possible to easily detect the change in vibrations of the resonator.

The present invention can also be used as a resonator for detecting attachment of a substance having a mass. This resonator includes a resonator body, a driving electrode that adds a voltage to the resonator body by electrostatic coupling and a detection electrode that detects the change in voltages due to the vibration of the resonator body by electrostatic coupling where the driving electrode and the detection electrode are spaced apart from the resonator body.

In this case, the peripheral portion of the resonator body may be a free end or fixed end. When the peripheral portion is the fixed end, a driving electrode and a detection electrode are preferably provided on the surface of the resonator body so as to have a space therebetween and be faced each other. Thereby, it is possible to perform the electrostatic coupling between the resonator body and the driving and detection electrodes on a plane and it is possible to increase the coupling capacity.

Moreover, the present invention has an aspect as a detection sensor provided with at least a pair of resonators in which the vibration characteristic changes when a substance having a mass attaches to the surface, a driving unit that vibrates the resonators, and a detection unit that detects attachment of a substance to the resonators by comparing the change in vibrations when a substance attaches between at least a pair of resonators.

In this case, the detection unit detects the change in the difference between vibration frequencies of the resonators when a substance attaches between at least a pair of resonators and thereby attachment of a substance to a resonator can be detected.

Moreover, by using one of at least a pair of resonators as a reference resonator to which a substance does not attach and detecting the change in vibrations of the other resonator on the basis of the vibration of the reference resonator when the substance attaches to the resonator, the detection unit can also detect attachment of the substance to the resonator.

This detection sensor detects a change in vibrations of a resonator generated when a substance is directly or indirectly attached or adsorbed to the resonator and thereby detects the substance. Not only presence or absence of the substance but also the quantity of the substance attached to the resonator can be detected.

In the case of this resonator, the amplitude of vibration depends on the position in the resonator. Moreover, the distribution of amplitudes of vibrations depends on the vibration mode or the order of harmonic vibration. The present invention uses these phenomena and electrically monitoring the vibration of the resonator so as to detect the change in vibrations of a resonator due to a substance which is attached or adsorbed to a region of the surface of the resonator. That is, when the substance is attached or adsorbed to a region having a large vibration amplitude, vibration is greatly changed compared to the case in which the substance is attached or adsorbed to a region having a small vibration amplitude. Thus, high-sensitivity detection can be made.

This region may include a portion in which the vibration amplitude of the resonator becomes 50% or more with respect to the maximum vibration amplitude of the resonator. In this case, this region may not always include the portion of the maximum vibration amplitude.

Moreover, it is also possible to set the region so as to include a portion in which the vibration amplitude of a resonator becomes maximum.

Moreover, it is possible to set two or more of the above region and cause substances different from each other to be attached or adsorbed to these regions. Thereby, a plurality of substances are detectable at the same time.

To cause a substance to be attached or adsorbed to a region of a resonator, it is also allowed to add an adsorption material capable of efficiently adsorbing molecules described above to a region of the surface of the resonator.

To add the adsorption material capable of efficiently adsorbing molecules to a region of the surface of a resonator, the following methods are considered.

1) Resist is patterned to portions other than a portion which selectively grows by using photolithography, a molecule recognition film is grown, and then the resist is removed by oxygen plasma or the like.

2) Resist is patterned on portions other than a portion which selectively grows by using photolithography, hydrophobic treatment such as silane treatment are applied to a selectively growing portion, a molecule recognition film is grown, and after the film is grown, the resist is removed by oxygen plasma or the like (in this case, it is allowed to remove the resist at the beginning).

3) Items 1) and 2) are performed by using the selective soft lithography.

4) A molecule recognition film is dissolved in a solvent, the concentration is adjusted, the molecule recognition film is selectively grown by using the ink jet method, spray method capable of forming a fine pattern, printing method, or soft lithography method, and then the solvent is dried to obtain a molecule recognition film of a predetermined organic or inorganic substance.

Generally, this adsorption material is formed separately from a resonator and is provided on the surface of the resonator. However, when the adsorption material has a certain degree of density, it is also allowed to integrally form the adsorption material and the resonator. Moreover, the resonator itself may be of the adsorption material. In this case, a mask film is preferably provided in a region to which a substance is not attached.

Furthermore, nanofiberization of polymer denotes change of polymer to fiber having a size (length) of several nanometers to several hundreds of micrometers in order to dramatically improve the adsorption performance of polymers having different adsorption characteristics to various molecules.

Furthermore, irregularity or groove is preferably formed on a part of the surface of the resonator so as for a substance to be attached or adsorbed to a region of a resonator. Thereby, the surface area of the resonator increases, and leads to efficient attachment of a substance to the surface of the resonator. By combining it with nanofiberization of the above-described adsorption material, further improvement of sensitivity can be achieved.

The basic study on the mechanical vibration of a disc type resonator has been performed for a long time and it can be said that the basic study such as vibration figure (vibration mode) for specifying the vibration state of a disc type resonator is already completed. At present, the study for purposing application of a resonator fabricated by the micromachine/MEMS technique to an RF signal wave filter is vigorously performed (for example, refer to Non-patent Document 3: C. T.-C. Nguyen, "Vibrating RF MEMS Technology; Fuel for an Integrated Microchemical Circuit Revolution?" The 13th International Conference on Solid-State Sensors, Actuators and Microsystems (Transducers '05), Korea, Jun. 5-9, 2005).

Study subjects according to change of disc type resonator to MEMS, include improvement of Q value for high sensitivity, driving and detecting method of resonator, and performance control by combination of resonators aiming at an application to wave filter, dedicated study has been performed on them. The present invention can provide a technique capable of improving the sensitivity of resonator by the following configuration.

As to improvement of the Q value for high sensitivity, the present inventors considered whether to improve the holding method of a resonator when changed to MEMS.

The Q value serving as a parameter for evaluating a resonator is determined by whether the resonator is present without loosing vibration energy and it can be shown by the relation of the expression (1).

$$\frac{1}{Q_{total}} = \frac{1}{Q_{air}} + \frac{1}{Q_{TED}} + \frac{1}{Q_{anchorLoss}} + \frac{1}{Q_{others}} \quad (1)$$

That is, the following are considered as main causes by which the vibration energy of a resonator is lost.

1) Loss $Q_{air}$ due to a peripheral medium such as air
2) Loss $Q_{TED}$ caused when a resonator vibrates and deforms
3) Loss $Q_{anchor\,Loss}$ due to holding mechanism of resonator and other loss $Q_{others}$ To decrease the energy loss as $Q_{air}$ in Item 1) where the representative peripheral media is air, this is settled by controlling the vibration of a resonator and selecting a vibration mode in which energy movement to peripheral media is less though the vibration energy of the resonator is large. For example, a disc type mechanical resonator vibrates only in the in-disk-face direction of the resonator (in the case of a cylindrical coordinates, vibration occurs only in r and θ directions but no vibration occurs in Z direction) and hardly moves large vibration energy to peripheral media whereas a drum film vibrating in Z direction does.

$Q_{TED}$ in Item 2) is caused when the resonator vibrates and adiabatic expansion and adiabatic compression occur due to the deformation. Therefore, it is said that the region where the adiabatic expansion occurs is cooled whereas the region where the adiabatic compression occurs is heated, a temperature gradient occurs in the resonator, and energy is lost when the heat is conducted and averaged. That is, the energy loss can be determined by the vibration mode and material of the resonator.

$Q_{anchor\,loss}$ in Item 3) is a loss due to the holding portion of the resonator, which is generated when vibration of the resonator goes down the holding portion. For example, by setting the holding portion to a place where the resonator does not vibrate, it is considered that energy loss can be eliminated. However, in the case of a normal disc type resonator, the above condition is not found as long as Si signal crystal serving as the most general resonator material is used.

For example, a mode most-well known in resonant modes of a disc type resonator is Wine-Glass mode (2,1). The radial-directional displacement U (r, θ) and tangential-directional displacement V (r, θ) which are mode functions in the vibration of a disc type resonator can be shown by the following expression (2).

$$U(r, \theta) = \left[A\frac{\partial}{\partial r}J_n(hr) + B\frac{n}{r}J_n(kr)\right]\cos n\theta \quad (2)$$

$$V(r, \theta) = -\left[A\frac{n}{r}J_n(hr) + B\frac{\partial}{\partial r}J_n(kr)\right]\sin n\theta$$

In the above expression (2), Wine-Glass mode (2,1) denotes the resonant mode of a lowest frequency when n=2.

In the case of the vibration of the (2,1) mode, the r component has a finite value in every r except r=0 in the radial direction, the finite value changes the circumferential direction in accordance with cos 2θ. In the case of angles θ=π/4, 3π/4, −3π/4, and −π/4, radial-directional vibration disappears. This position is referred to as nodal point and a technique for holding a resonator at the position is also proposed.

However, the (2,1) mode is a compound mode and there is a vibration component in the tangent direction. Therefore, the r component has a finite value in every r except r=0 in the tangent-directional vibration and the finite value changes in accordance with sin 2θ in the circumferential direction. Therefore, in angles θ=π/4, 3π/4, −3π/4, and −π/4 where U(r,θ) is 0, that is cos 2θ is 0, the amplitude of V(r,θ) becomes maximum because sin 2θ becomes 1, −1, 1, and −1. That is, to hold a circular resonator which vibrates in the Wine-Glass mode (2,1) at a point where there is no vibration of the radial component, the circular resonator is held with interrupting the vibration of the tangential component and it is impossible to hold the resonator at a point where there is no vibration for any directional component.

Therefore, as a result of earnest study, the present inventors found a technique using an annular resonator capable of eliminating vibrations of the radiant component and tangential component differently from the above case.

A detection sensor of the present invention thus constituted is provided with a resonator whose vibration characteristic is changed due to attachment or adsorption of a substance having a mass, driving unit that vibrates the resonator, detection unit that detects a substance by detecting the change in vibrations of the resonator and the resonator is annular because an opening is formed at the central portion thereof and its outside diameter is Ra and its inside diameter is Rb. Moreover, in the case of the displacement of the position r when the resonator vibrates on the positional coordinates (r,θ), the radiant-directional displacement is shown by U(r) and the tangential-directional displacement is shown by V(r) as shown in the following expression (3). In this case where r is Ra or Rb, the resonator is characterized by having the outside diameter Ra and inside diameter Rb almost satisfying U(r)=0 or V(r)=0.

$$U(r) = \frac{\partial}{\partial r}J_n(hr) + A_6\frac{n}{r}J_n(kr) + A_7\frac{\partial}{\partial r}Y_n(hr) + A_8\frac{n}{r}Y_n(kr) \quad (3)$$

$$V(r) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)$$

In the expression (3), $$h = \omega\sqrt{\frac{\rho(1-\sigma^2)}{E}},$$

$$k = \omega\sqrt{\frac{\rho(2+2\sigma)}{E}},$$

$$k = h\sqrt{\frac{2}{1-\sigma}}$$

σ: Poisson's ratio of resonator material, E: Young's modulus of resonator material, ρ: Density of resonator material, ω: Angular frequency, A6, A7, and A8: Coefficient, n: Order of vibration mode.

In the expression (3), A6, A7, and A8 are uniquely determined by the natural vibration mode specified by the outside and inside diameters of the resonator, the Young's modulus, density and Poisson's ratio of the resonator material, boundary condition (in this case, free-free condition) of the resonator. Specifically, when setting A5 to 1 in expression (36) to be described later, A6, A7, and A8 are solutions of the simultaneous linear equations in expression (36).

Thus, in the case of an annular resonator, vibration may not occur in the outside or inside-diameter portion of the annular resonator depending on the ratio between the outside diameter Ra and the inside diameter Rb. The ratio in this case depends on the Poisson's ratio of a resonator material, mode number n in the vibration mode when vibrating the resonator, or the order m of a harmonic vibration.

Moreover, when r is equal to Ra in expression (3), a resonator is supported by the outside-diameter portion when U(r)=0 or V(r)=0 is almost satisfied. Furthermore, when r is equal to Rb in expression (3), the resonator is supported by the inside-diameter portion when U(r)=0 or V(r)=0 is almost satisfied.

Furthermore, when r is equal to Ra or Rb in expression (3) and U(r)=0 is almost satisfied, the resonator is supported at a position θ where sin (nθ) is equal to 0. Moreover, when r is equal to Ra or Rb in expression (3) and V(r)=0 is almost satisfied, the resonator is supported at a position θ where cos(nθ) is equal to 0.

Thus, it is possible to eliminate vibrations of the radial component and tangential component in the resonator.

Here, the present invention allows not only a case of completely satisfying U(r)=0 or V(r)=0 but also a case of almost satisfying U(r)=0 or V(r)=0. This is because it is difficult to form a resonator in accordance with the outside diameter Ra and inside diameter Rb capable of completely satisfying the condition of U(r)=0 or V(r)=0 due to manufacturing tolerance or the like and even in the case of slightly deviating from the condition of U(r)=0 or V(r)=0, there is a case in which vibration is sufficiently small in the outside-diameter portion or inside-diameter portion.

This detection sensor detects the change in vibrations of a resonator caused by the fact that a substance directly or indirectly attaches or adsorbs to the resonator and thereby, detects the substance. Detection of the substance realizes not only detection of presence or absence of the substance but also detection of the quantity of the substance attached to the resonator.

To cause the substance to be attached or adsorbed to the resonator, the above-described adsorption material may be added to the surface of the resonator so that adsorption of molecules can be efficiently performed.

This detection sensor can employ a specific molecule, or a plurality of kinds of molecules having a specific characteristic or feature as a substance to be detected. Thereby, the present detection sensor can be used for a gas detection sensor, smell sensor or the like. For this, when the resonator is, for example, intended for molecules derived from gas or organism, floating molecules in a life space, or volatile molecules as a specific molecule, it is preferable to detect only a specific type of a molecule with high selectivity. Moreover, by using a plurality of detection sensors having a high selectivity, it is possible to recognize a plurality of kinds of molecules or broaden the use application. Furthermore, it is possible to detect a molecule group having a specific feature referred to as global recognition or a molecule group having the same side chain. In this case, by using a plurality of detection sensors, it is allowed to recognize a molecule group by the signal processing or processing using software in accordance with the difference of detection performances between a plurality of detection sensors. Moreover, it is allowed to detect specific protein, enzyme, or sugar chain by changing a configuration so as to operates in liquid.

Detection of a very small mass can be used for film thickness monitoring when forming a thin film and bio-study such as antibody antigen reaction or protein adsorption action. A detection sensor of the present invention is preferable for this purpose.

Moreover, for a compact stable high-sensitivity household or private gas sensor or portable and disposable purpose of detection of a toxic substance floating in air, it is considered to use a detection sensor or resonator of the present invention. The higher sensitivity can provide a broader range of applications and might possibly enable detection and identification of smells. Furthermore, a detection sensor of the present invention can be used in the purposes other than the above.

Furthermore, if single-crystal or polycrystalline Si is used as a structural material for a detection sensor of the present invention, the detection sensor can be fabricated by the MEMS technique, making it possible to form the detection sensor in the same chip as a Si semiconductor. In this case, a very-inexpensive high-performance apparatus for detecting a very-small substance is obtainable.

DETAILED DESCRIPTION OF THE PREFERRED EMBODIMENTS

The present invention is described below in detail in accordance with the embodiments shown in the accompanying drawings.

Figure 1:
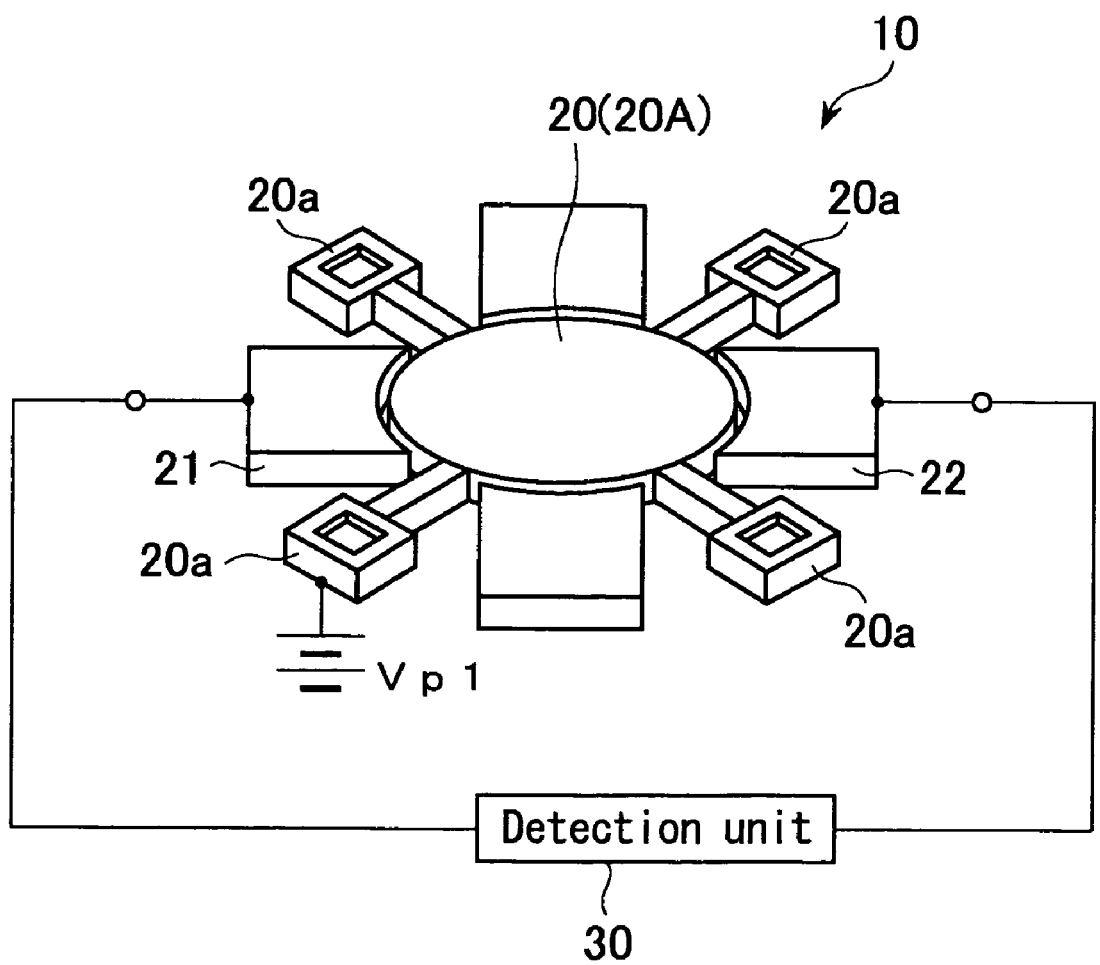
FIG. 1 shows a configuration of a sensor of a first embodiment.

FIG. 1 is an illustration showing a basic configuration of a sensor (detection sensor) 10 of an embodiment of the present invention.

The sensor 10 shown in FIG. 1 is provided with a disc type resonator (resonator) 20 which is disc shaped and has circular, rectangular, and properly other shapes as a whole and whose vibration frequency changes when a substance to be detected such as a molecule having a mass is attached, a driving source (not illustrated) for vibrating the disc type resonator 20, and a detection unit 30 for detecting a change in vibration characteristics of the disc type resonator 20.

The driving source (not illustrated) uses the electrostatic effect or piezoelectric effect depending on the current generated by an external not-illustrated controller to vibrate the resonator 20.

Moreover, the detection unit 30 detects the vibration of the resonator 20 in accordance with the electrostatic effect or piezoelectric effect and outputs the vibration as an electrical signal. In this case, when a substance having a mass attaches to the resonator 20, the number of vibrations of the resonator 20 changes due to the mass. The detecting potion 30 can detect presence or absence of attachment of a substance to the resonator 20 or the quantity of a substance attached to the resonator 20 by monitoring electrical vibration outputted from the detection unit 30.

The basic principle of the sensor 10 using the disc type resonator 20 is described below.

A frequency function for determining the number of vibrations of the disc type resonator 20 under a state in which the outer periphery of the resonator 20 is not fixed (free) and the mode function showing the shape of the vibration are determined as described below and they are not related to the thickness of the resonator 20.

That is, the vibration frequency (frequency function) of the disc type resonator 20 in an open-end condition and vibration figure (mode function) become the following description in accordance with the analysis using cylindrical coordinates (r, θ, and z). A denotes the amplitude of dilatation (expansion or contraction direction) and B denotes the amplitude of rotation (rotational direction).

The vibration generated in the disc type resonator 20 has the following three modes: (a) radial mode (mode in which it vibrates only in the diameter direction), (b) tangential mode (mode in which it vibrates only in θ direction), and (c) compound mode (mode in which diameter-directional vibration and θ-directional vibration are conjugated).

In the case of the radial mode, frequency function and mode function are shown below.

Frequency function:

$$hR\frac{J_0(hR)}{J_1(hR)} = 1-\sigma \quad (4)$$

Mode function: $U(r,\theta)=AhJ_1(hr)$, $V(r,\theta)=0$ (5)

Moreover, in the case of the tangential mode, the frequency function and mode function are shown below.

Frequency function:

$$kR\frac{J_0(kR)}{J_1(kR)} = 2 \quad (6)$$

Mode function: $U(r,\theta)=0$, $V(r,\theta)=-BkJ_1(kr)$ (7)

In the case of the compound mode, the frequency function and mode function are shown below. For example, in the case of a compound mode n, (n,m) denotes a mode in which the m-th value in ascending order of kR or hR satisfying the frequency function shown in (9) is to be a solution.

Frequency function (n=1):

$$hR\frac{J_0(hR)}{J_1(hR)} = 4 - \frac{(kR)^2}{2} - kR\frac{J_0(kR)}{J_1(kR)} \quad (8)$$

Frequency function (n>1):

$$\left[hR\frac{J_{n-1}(hR)}{J_n(hR)} - n - \frac{(kR)^2}{2(n^2-1)}\right]\left[kR\frac{J_{n-1}(kR)}{J_n(kR)} - n - \frac{(kR)^2}{2(n^2-1)}\right] = \quad (9)$$

$$n^2\left[\frac{(kR)^2}{2(n^2-1)} - 1\right]^2$$

Mode function:

$$U(r,\theta) = [A(\partial/\partial r)J_n(hr) + nB(1/r)J_n(kr)]\cos n\theta$$

$$V(r,\theta) = -[nA(1/r)J_n(hr) + B(\partial/\partial r)J_n(kr)]\sin n\theta \quad (10)$$

The optional coefficient A denotes the amplitude of diameter-directional vibration and the optional coefficient B denotes the amplitude of axis-directional vibration and the ratio between A and B are shown by the following expression.

$$\frac{B}{A} = \frac{2hRJ_{n-1}(hR)/J_n(hR) + (kR)^2 - 2n(n+1)}{2n\{kRJ_{n-1}(kR)/J_n(kR) - (n+1)\}}, \quad (11)$$

$$n \neq 0$$

$J_n(x)$ denotes first-class Bessel function.

$$h = \omega_0\sqrt{\frac{\rho(1-\sigma^2)}{E}},$$

$$k = \omega_0\sqrt{\frac{2\rho(1+\sigma)}{E}}$$

In this case,
n: Number of modes
$\omega_0$: Vibration angular frequency (=$2\pi f_0$)
R: Radius of resonator
$\rho$: Density of resonator material
$\sigma$: Poisson's ratio of resonator material
E: Young's modulus of resonator material Moreover, the effective mass $M_{re}$ can be determined as shown below.

$$M_{re}(R_0, \theta_0) = \rho t \frac{\int_0^R \int_0^{2\pi} [U(r,\theta) + V(r,\theta)]^2 r\,dr\,d\theta}{U(R_0,\theta_0)^2 + V(R_0,\theta_0)^2} \quad (12)$$

In this case, t denotes the thickness of a resonator.

Moreover, by using the effective mass $M_{re}$ and vibration frequency $\omega_0$, the equivalent rigidity $K_{re}$ is determined as shown below.

$$K_{re} = \omega_0^2 M_{re} \quad (13)$$

The above expression shows that the vibration of the disc type resonator 20 is equivalent to a vibration at the vibration frequency (angular frequency) $\omega_0$ when the weight having an effective mass $M_{re}$ is dangled on a spring having a rigidity $K_{re}$.

Moreover, by rewriting the above expression, the vibration frequency when the effective mass $M_{re}$ increases by $\delta M_{re}$ can be shown by the following expression.

$$\omega_{re} = \sqrt{\frac{K_{re}}{M_{re} + \delta M_{re}}} \approx \sqrt{\frac{K_{re}}{M_{re}}}\left(1 - \frac{\delta M_{re}}{2M_{re}}\right) = \omega_0\left(1 - \frac{\delta M_{re}}{2M_{re}}\right) \quad (14)$$

That is, the change in the vibration frequency when the effective mass $M_{re}$ increases by $\delta M_{re}$ is shown by the following expression.

$$\Delta\omega_{re} \approx -\frac{\delta M_{re}}{2M_{re}}\omega_0 \quad (15)$$

Thus, the vibration frequency changes when a substance having a mass attaches to the disc type resonator 20. Therefore, by detecting the change in the vibration frequency, it is possible to detect a very-small mass. According to the above expression (15), it is found that the fluctuation value of a frequency increases when the ratio between the $\delta M_{re}$ corresponding to a very small mass and the effective mass $M_{re}$ decreases and the sensitivity of a very-small mass detector is high. In this case, the thickness t of the disc type resonator 20 is not related to the vibration frequency. Therefore, by decreasing the thickness t of the disc type resonator 20 up to a range allowed by the mechanical strength and decreasing the effective mass $M_{re}$, it is possible to easily improve the sensitivity.

In the case of the above disc type resonator 20, the vibration amplitude depends on a position on the disc type resonator 20. The way of vibration of the disc type resonator 20 depends on the vibration mode and higher-harmonic vibration order. Therefore, a position where the vibration amplitude is large changes. However, by detecting attachment of a substance at the position where the vibration amplitude is large, it is possible to detect a substance with higher sensitivity.

FIGS. 2 to 7 respectively show a distribution of the magnitude of the vibration amplitude on the surface of a disc type resonator in each vibration mode including harmonic vibration up to fourth order by sequentially separating the distribution to 10 stages in 10% separation when assuming the maximum amplitude as 100%. Specifically, this is a result of calculating the magnitude D of the vibration amplitude at a place (r,θ) by the following expression. In this case, in FIGS. 2 to 7, areas separated into 10 stages are set to regions A1, A2, . . . , A10 from the largest vibration amplitude in order. However, in each drawing, the regions A1 to A10 are shown only for the vibration at the lowest order and at least the region A1 is shown for vibrations of other orders. Moreover, n denotes the number of modes of the vibration mode and m denotes the order of higher-harmonic vibration.

$$D = \sqrt{V(r,\theta)^2 + U(r,\theta)^2} \quad (16)$$

As shown in FIGS. 2 to 7, a region having a large vibration amplitude is restricted in most vibration modes.

Figure 2:
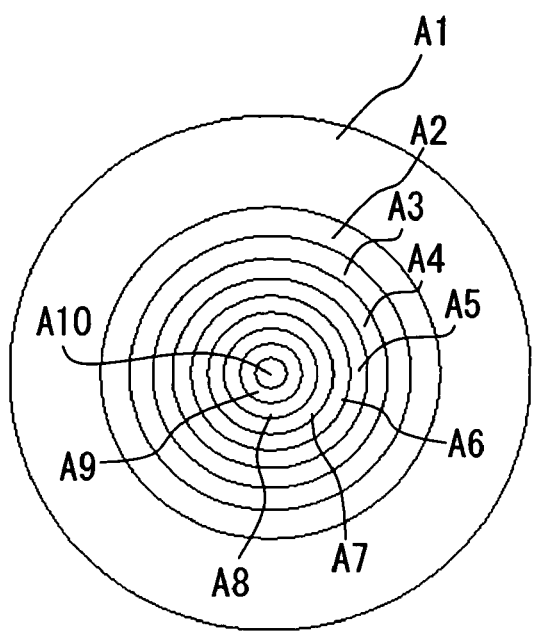
FIG. 2 shows a distribution of the vibration amplitude of a disc type resonator by separating it into 10 stages, in which an example of vibrating a resonator in the radial mode is shown in the vibration mode n=0 and harmonic vibration order m=1, 2, 3 and 4.
Figure 2:
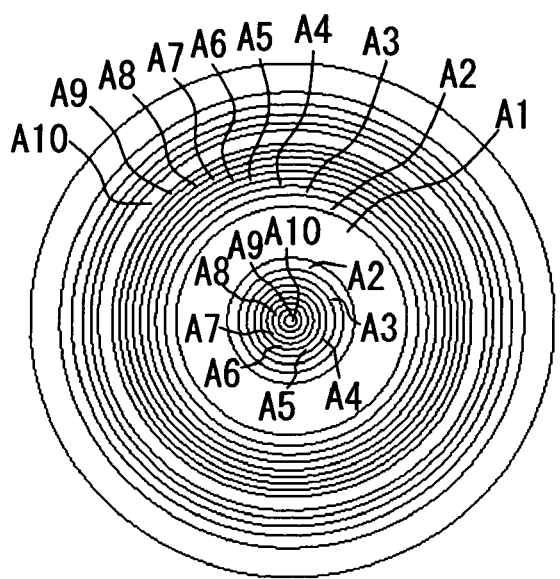
Figure 2:
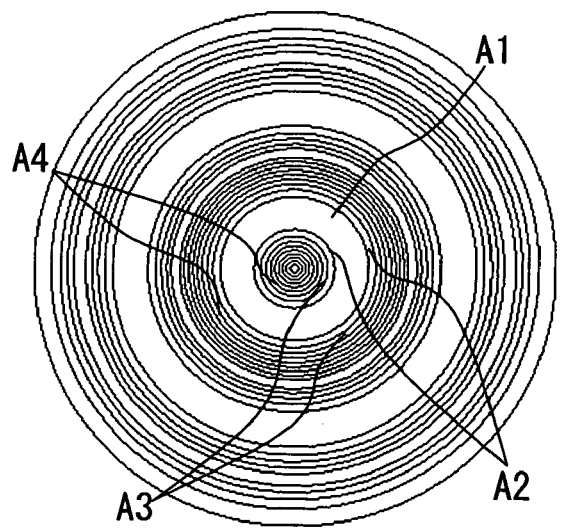
Figure 2:
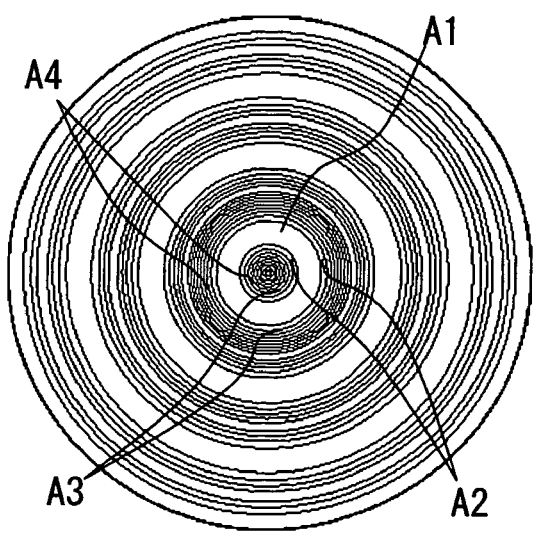
Figure 3:
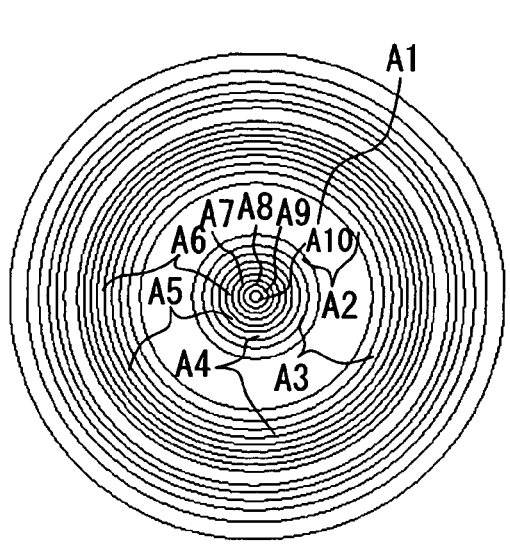
FIG. 3 similarly shows a distribution of the vibration amplitude of a disc type resonator in the tangential mode, the vibration mode n=0 and harmonic vibration order m=1, 2, 3 and 4.
Figure 3:
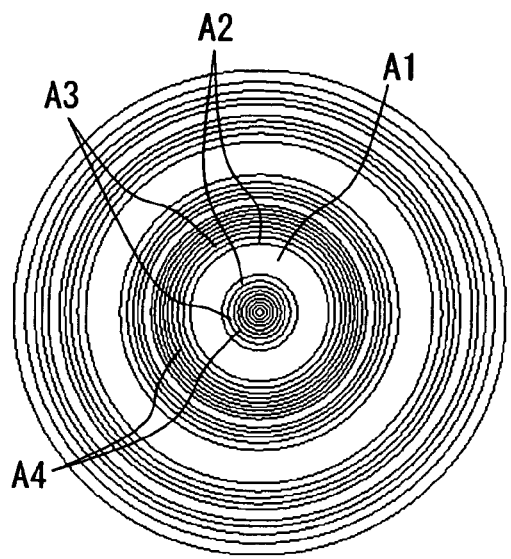
Figure 3:
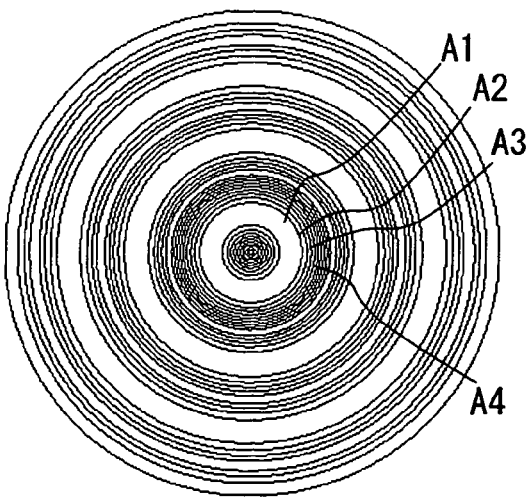
Figure 3:
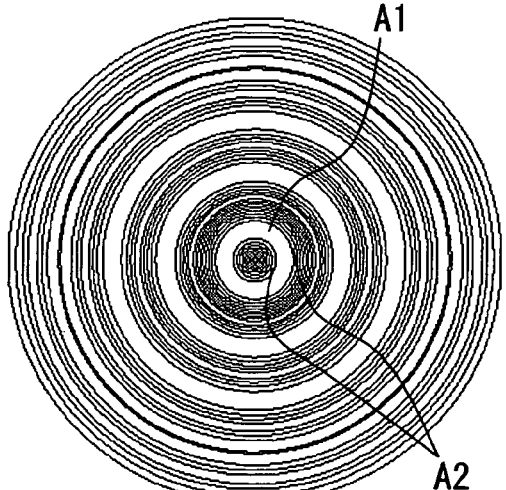
Figure 4:
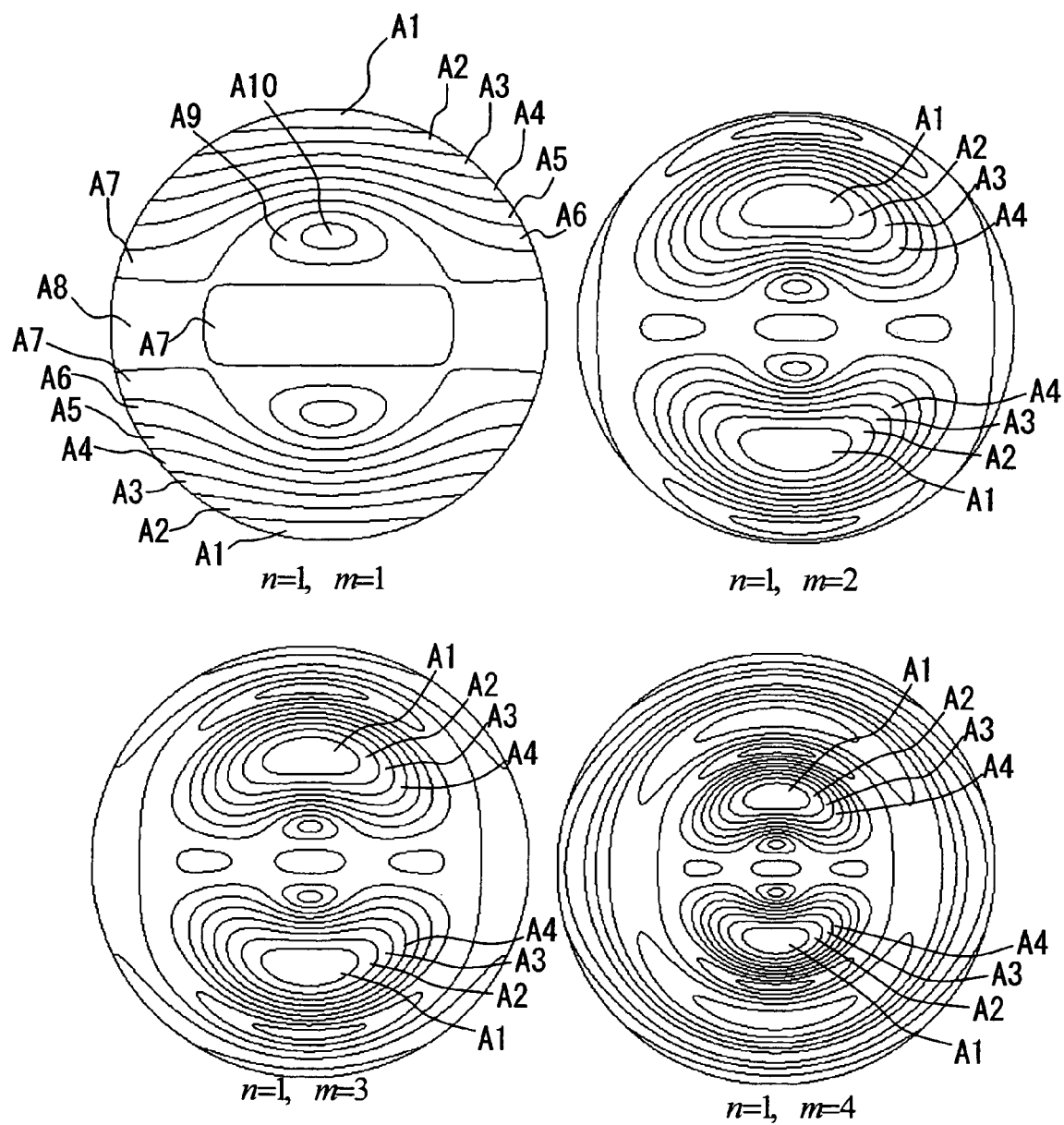
FIG. 4 similarly shows a distribution of the vibration amplitude of a disc type resonator in the compound mode, vibration mode n=1, and harmonic vibration order m=1, 2, 3 and 4.

As shown in FIG. 2, in the case of vibration of n=0, the magnitude of the vibration amplitude of a resonator is separated like a concentric circle and each region becomes annular. Moreover, as shown in FIGS. 4 to 7, in the case of the vibration of n≧1, the region A1 having the maximum vibration amplitude is present at a plurality of places.

FIGS. 8 to 13 respectively show a mass ratio between the effective mass occupied by the region separated into 10 stages and all effective masses and the area ratio between the area of the region and all the surface area of the resonator, from the largest vibration amplitude in order.

As shown in FIG. 8 to 13, it is found that the value of effective mass ratio in a region having a large vibration amplitude is larger than the value of the area ratio of the region in every vibration mode and higher-harmonic vibration order. That is, a region having a large vibration amplitude has a large effective mass though it actually has a small mass. In other words, when attaching a very-small substance to be measured to the region having the large vibration amplitude, this denotes that it is possible to feel an effective mass larger than the real mass of the very-small substance.

Therefore, FIGS. 14 to 19 respectively show a graph in which a rate of accumulated effective mass obtained by sequentially adding the effective mass descending order of regions having larger vibration amplitude to the whole effective mass of the disc type resonator is assigned to the axis of ordinate and a rate (area ratio) of accumulated area obtained by sequentially adding the area of each region to the whole area of the disc type resonator is assigned to the axis of abscissa. According to FIGS. 14 to 19, in the case of the lowest subsequence mode of the radial mode when m=1 in FIG. 14, the ratio becomes 65%/50%, i.e., 1 or more, because the accumulated effective mass is approx. 65% of the effective mass when the accumulate area is 50%. In the cases of n=2 and m=2, n=2 and m=3 shown in FIG. 17, and n=3 and m=2, n=3 and m=3 shown in FIG. 18, the accumulated effective mass becomes 90% or more when the accumulated area is 50% and the ratio becomes 90%/50% which is a value close to 2. Moreover, in thee modes, the accumulated effective mass when the area ratio is as small as 10%, becomes a value of approx. 40% of the whole. This shows that it is possible to feel a small mass as a large effective mass in a region having a large vibration amplitude. Therefore, it is suggested that by attaching a very-small substance to be detected to the portion having a large vibration amplitude, it is possible to improve a detection sensitivity.

Improvement of detection sensitivity according to the method having been described is studied in detail. First, the total mass of a resonator is assumed as M, density of it is assumed as $\rho$, thickness of it is assumed as t, area of it is assumed as S, mass of a very-small substance is assumed as $\delta M$, and density of it is assumed as $\delta\rho$. When a very-small substance is uniformly attached to the surface of a resonator, M can be shown in accordance with the following expression.

$$M+\partial M = \rho t S + \partial \rho t S \qquad (17)$$

When concentrating a very-small substance having the same mass $\delta M$ on the area $\delta S$ and selectively attaching the very-small substance to the area $\delta S$, expression (15) is obtained. Therefore, it is possible to show an equivalent density $\delta\rho'$ by expression (19).

$$M+\partial M = \rho t S + \partial \rho' t \partial S \qquad (18)$$

$$\partial \rho' = \partial \rho S / \partial S \qquad (19)$$

Moreover, when the effective mass of a resonator is rewritten as expression (20) and the total effective mass when uniformly attaching a very-small substance on the face of a resonator by using expression (20) is shown by expression (21). In this case, the effective mass of the very-small substance is $\delta M^U_{re}$.

$$M_{re} = \rho t \frac{\int_0^R \int_0^{2\pi} [U(r,\theta) + V(r,\theta)]^2 r\, dr\, d\theta}{[U(r_0,\theta_0)]^2 + [V(r_0,\theta_0)]^2} = C_0 \rho t \int_S F(S)\, dS \qquad (20)$$

$$M_{re} + \partial M^U_{re} = C_0 \rho t \int_S F(s)\, dS + C_0 \partial \rho t \int_S F(s)\, dS \qquad (21)$$

Furthermore, the effective mass when concentrating a very-small substance on the area $\delta S$ and attaching the substance to the area is shown by the following expression. In this case, $\delta M^S_{re}$ is the effective mass of the very-small substance.

$$Th\, M_{re} + \partial M^S_{re} = C_0 \rho t \int_S F(s)\, dS + C_0 \partial \rho t \frac{S}{\partial S} \int_{\partial S} F(s)\, dS \qquad (22)$$

mass of a very-small substance when uniformly attaching the very-small substance and the effective mass when selectively attaching the very-small substance to a specific region is SIR (Sensitivity Improve Ratio) and the following expression can be obtained from expressions (21) and (22). However, integration of molecules is executed for a region to which a very-small substance is selectively attached.

$$SIR = \frac{\partial M^S_{re}}{\partial M^U_{re}} = \frac{\int_{\partial S} F(s)\, dS / \partial S}{\int_S F(s)\, dS / S} \qquad (23)$$

In accordance with the above-mentioned considerations, FIGS. 20 to 25 respectively show a result of calculating the sensitivity improvement as a result of selecting a specific surface of the resonator, that is, a region having a large vibration amplitude and attaching a very-small substance to the region. From FIGS. 20 to 25 it is read that sensitivity improvement of the maximum of 11.2 times in the calculation range is possible by selectively selecting a portion having a large vibration amplitude and attaching a very-small substance to the portion.

A specific very-small-substance attaching region depends on each mode or the order of the higher-harmonic vibration of the mode. However, in the case of vibration modes including the radial mode, it can be read from the axis of ordinate when the axis of abscissa (area ratio) in FIGS. 20 to 25 is 0.1: seeing the sensitivity improve ratio SIR that the region A1 shown (maximum vibration amplitude of 90% or more) in FIGS. 2 to 7 is a region having the largest vibration amplitude and it is possible to improve the sensitivity of three- to four-times by using the region.

Moreover, when expecting the highest sensitivity, it is also found that it is possible to realize sensitivity improvement of maximum of 10 times or more by concentrically attaching a very-small substance to a local portion having the largest vibration amplitude in the region A where the vibration amplitude is large. It is a matter of course that it is not necessary to restrict the portion to the region A1. By attaching the very-small substance to the region A1 and its peripheral portion, its advantage is high enough.

In the case of FIGS. 26 to 31, the standardized vibration amplitude (relative amplitude) when assuming the maximum amplitude as 1 is taken to the axis of abscissa and the sensitivity improve ratio (SIR) at the amplitude shown in expression (23) is taken to the axis of ordinate. It is found that the sensitivity improve ratio becomes 1 or more when the vibration amplitude is at approx. 50% or more of the maximum vibration amplitude and the detection sensitivity is improved compared to the case of uniformly applying a very-small substance on the surface of a resonator.

Thus, when detecting a substance, it is possible to detect a substance with high sensitivity by attaching the substance to a specific region of the resonator having a large vibration amplitude.

That is, to detect a substance, it is preferable to at least select one or more regions respectively including a portion having the maximum vibration amplitude from regions A1 to A10 as a specific region and attach a substance to the specific region. It is preferable to at least assume only the region A1 including a portion having the maximum vibration amplitude as a specific region to detect attached substance. Moreover, to securely improve the sensitivity, it is preferable to assume the regions A1 to A5 respectively having 50% or more of the maximum vibration amplitude as specific regions and attach a substance to the specific regions to detect the substance.

In the case of a vibration mode of n=1 or more, that is, the compound mode, a plurality of maximum vibration amplitude portions are present. Therefore, even if a very-small substance is similarly attached to the portions or the substance is attached to a specific portion among them, the advantage is the same unless a quantity of very-small substance influencing the vibration mode is attached.

Therefore, it may be possible to realize a structure capable of detecting many kinds of very-small substances at the same time and with high sensitivity by assuming a plurality of regions A1 respectively including a portion which has the maximum vibration amplitude or a plurality of regions including the region A1 and its peripheral regions as specific regions, attaching very-small substances different from each other to these specific regions, and monitoring the diffusion state of the very-small substances in accordance with the fluctuation of the vibration frequency of a resonator. In this case, when the resonator vibrates in the compound mode of (n,m), the maximum amplitude region can be shown by the number of maximum amplitude regions=2n.

Moreover, when the resonator vibrates in the radial mode of (mR) or tangential mode, the maximum vibration region appears as a ring. Thus, it is possible to simultaneously detect a plurality of very-small substances by dividing the ring in accordance with the number of very-small substances to be detected and attaching the very-small substances of different kinds to each divided specific region.

From these study results, a trend is shown that the improvement degree of detection sensitivity is raised as the order of harmonic vibration rises. Particularly, the trend becomes remarkable in the radial mode (mR) and tangential mode (mT).

Thus, in the case of a detection sensor using a frequency change of a resonator as the detection principle, it is possible to improve the detection sensitivity by "causing a detection substance to be selectively attached or adsorbed to a place having a large vibration amplitude".

A plurality of embodiments are shown as the sensor 10 using the disc type resonator 20.

First Embodiment

As shown in FIG. 1, the disc type resonator 20A of this embodiment is formed of, for example, Si and supported so that only a support portion 20a is fixed and the remaining peripheral portion becomes a free end.

A driving electrode (driving unit) 21 and a detecting electrode 22 are set nearby the disc type resonator 20A.

The driving electrode 21 and detecting electrode 22 are arranged by keeping a small gap so that electrostatic coupling occurs when applying a predetermined voltage to the disc type resonator 20A. In the case of the configuration shown in FIG. 1, the radial mode is set which vibrates the disc type resonator 20A in the radial direction. The radial mode is hardly influenced by the viscosity of air and a high Q value (Quality Factor) can be easily obtained.

In the case of this disc type resonator 20A, when applying an electrical signal having a predetermined frequency to the driving electrode 21 from a power supply, the disc type resonator 20A vibrates at the above frequency in accordance with electrostatic coupling. The detecting electrode 22 detects the electrical vibration of the disc type resonator 20A in accordance with electrostatic coupling and outputs the vibration to the detection unit 30. In this case, when a substance having a mass attaches to the disc type resonator 20A, the number of vibrations of the disc type resonator 20 is changed due to the mass. Therefore, the detection unit 30 can detect presence or absence of attachment of a substance to the disc type resonator 20A or detect the quantity of the substance attached to the disc type resonator 20A by monitoring the electrical vibration outputted from the detecting electrode 22.

To efficiently drive the disc type resonator 20A, it is necessary to increase the coupling capacity by forming a very small gap of, for example, 100 nm or less between the disc type resonator 20A and the driving electrode 21.

The sensor 10 having the above configuration can detect presence or absence of a substance having mass or the mass with high-sensitivity by using the disc type resonator 20A.

Moreover, the disc type resonator 20A uses single-crystal or polycrystalline Si as a structural material and can be fabricated by the MEMS technique. Therefore, it is possible to build the sensor 10 in the same chip as a Si semiconductor.

A molecule or the like to be detected drops on and attaches to the upper face of the disc type resonator 20A. In this case, to improve the attachment efficiency of the molecule or the like to be detected to the region A1 to be set as a specific region and including a portion having the largest vibration amplitude or the region A1 and its peripheral region, it is preferable to form irregularity, groove or the like on a portion corresponding to a specific region on the surface of the disc type resonator 20A. Thereby, the upper face of the disc type resonator 20A easily catches a molecule or the like dropped in, for example, a diagonal direction.

Second Embodiment

An example when the outer periphery of the disc type resonator 20A is not fixed is described above. However, it is also possible to use a structure for fixing the outer periphery. Because the configuration of the whole sensor 10 is the same as the case of the above first embodiment, description is made by focusing on only a disc type resonator 20B and description of other configurations is omitted.

Figure 32:
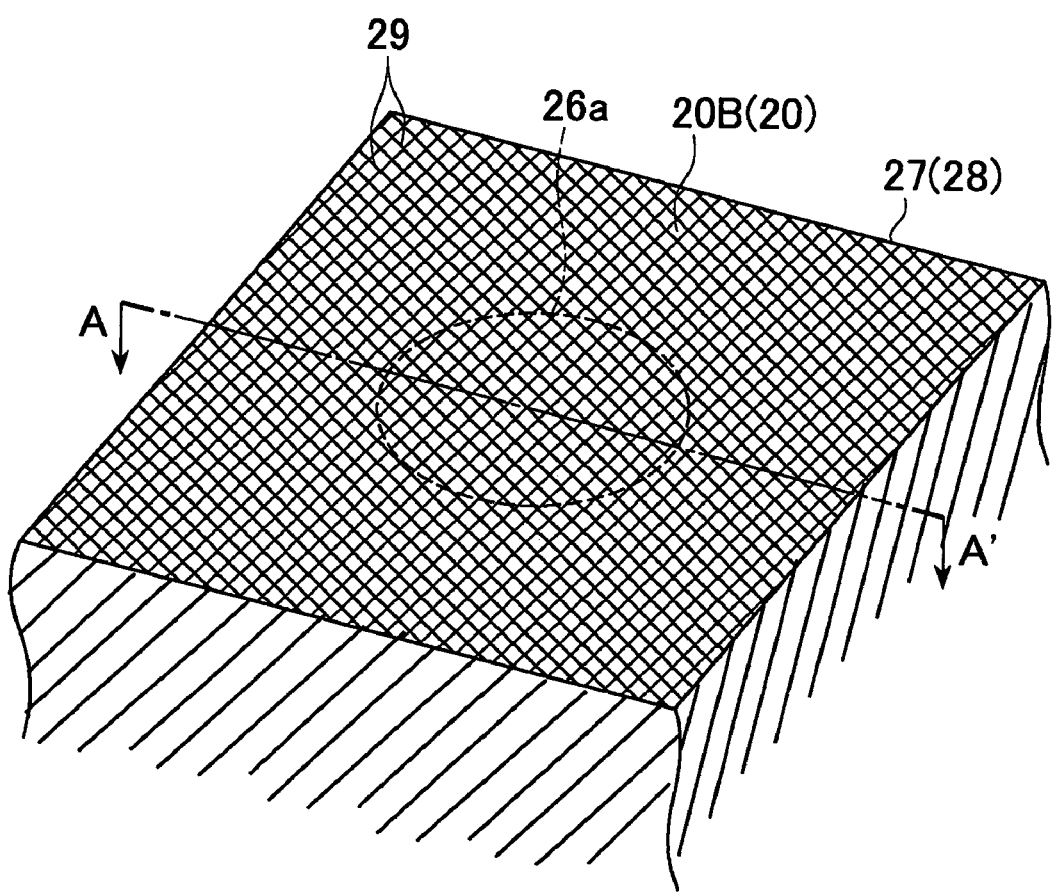
FIG. 32 shows a state in which a groove is formed on the surface of the sensor of a second embodiment.
Figure 33:
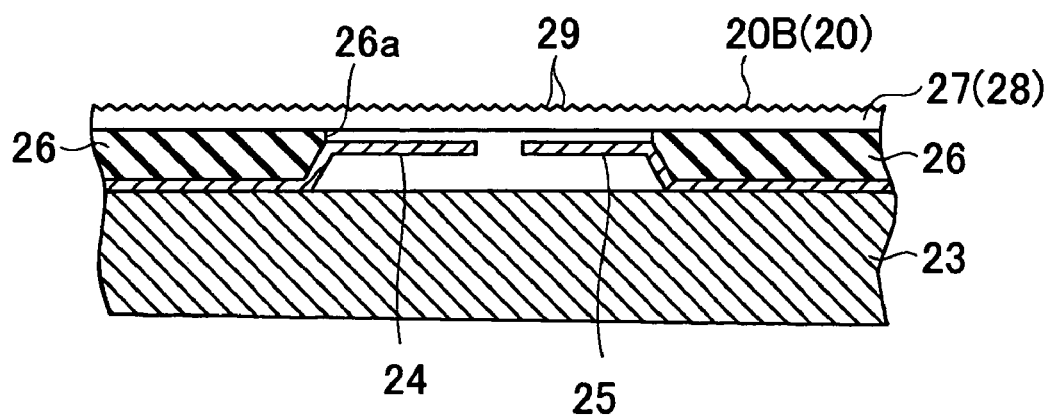
FIG. 33 is a cross-sectional view taken along the line A-A' in FIG. 32.

FIGS. 32 and 33 are illustrations showing a configuration of the fixed-end-type disc type resonator 20B and FIG. 33 is a cross-sectional view taken along the line A-A' in FIG. 32.

As shown in FIG. 33, the fixed-end-type disc type resonator 20B has a configuration in which a driving electrode (driving unit) 24 and a detecting electrode 25 are formed on a substrate 23 made of Si having an insulating property and a Si layer 27 is laminated on the electrodes 24 and 25 through an insulating material 26. In this case, as shown in FIGS. 32 and 33, a circular or rectangular opening 26a is formed on the insulating material 26 and thereby, the Si layer 27 can vibrate as a resonator body 28 at the portion of the opening 26a. Also in this case, it is preferable to form irregularity, groove 29 or the like on the surface of the Si layer 27 in order to improve the attachment efficiency of a molecule or the like to be detected.

Moreover, the driving electrode 24 and detecting electrode 25 are formed so as to be almost parallel with the resonator body 28 while keeping a predetermined gap between the electrodes and the resonator body 28 at the portion of the opening 26a.

Figure 34:
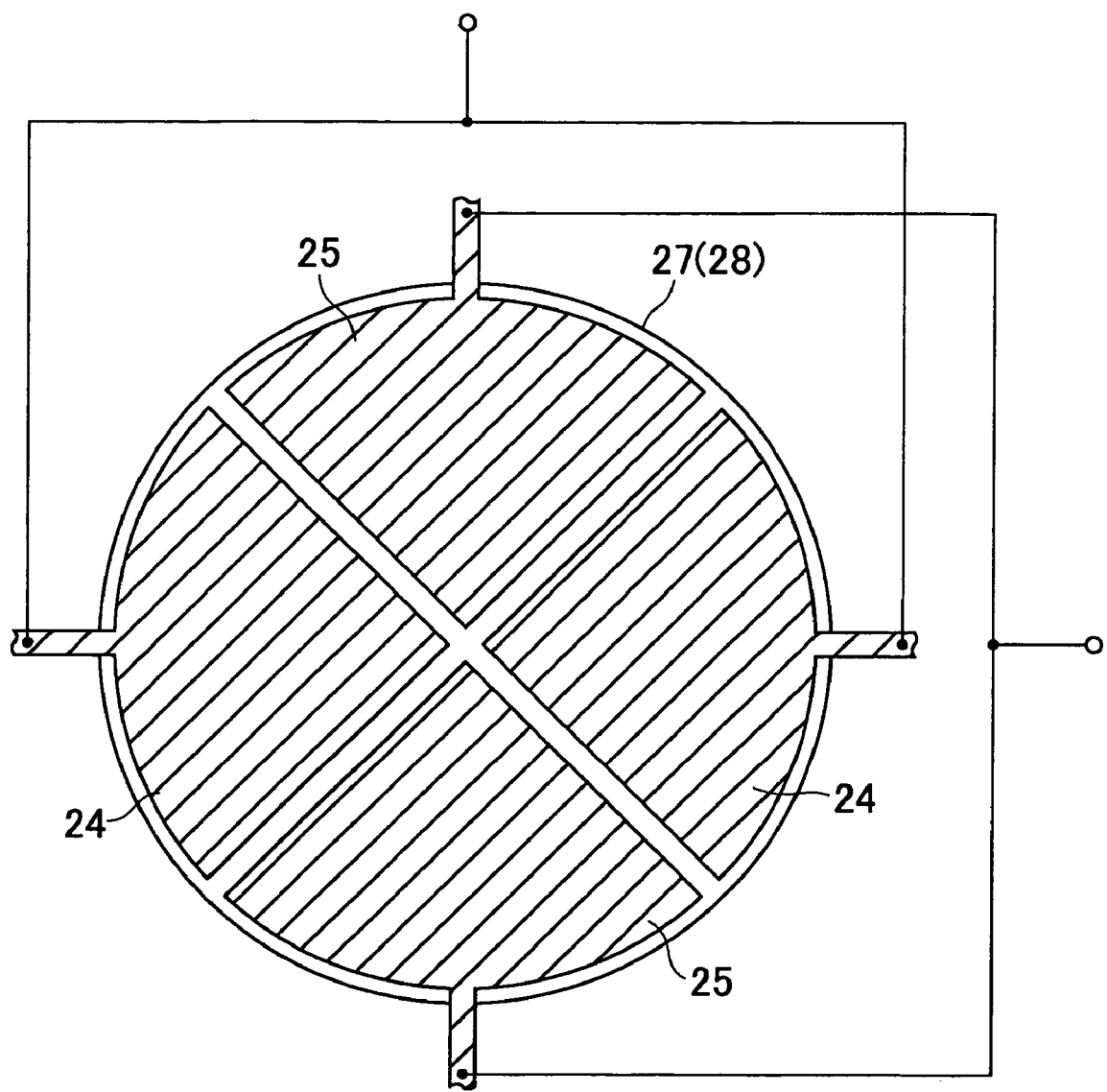
FIG. 34 shows a driving electrode and detection electrode set to a sensor.

When these driving electrode 24 and detecting electrode 25 vibrate in the compound mode of n=2, it is preferable to set two sets of electrodes respectively by forming the driving electrode 24 and detecting electrode 25 like a fan as shown in FIG. 34. Moreover, when using the vibration in the compound mode of n=1, it is preferable to form the driving electrode 24 and detecting electrode 25 into a semicircle respectively and set a pair of electrodes respectively.

In the case of the sensor 10 constituted by using the disc type resonator 20B, when applying an electrical signal having a predetermined frequency to the driving electrode 24 from a power supply, the disc type resonator 20B vibrates at the above frequency in accordance with electrostatic coupling. The detecting electrode 25 detects the electrical vibration of the disc type resonator 20B in accordance with electrostatic coupling and outputs the vibration to the detection unit 30. In this case, when a substance having a mass attaches to the resonator body 28 of the disc type resonator 20B, the number of vibration of the resonator body 28 is changed due to the mass.

Also in the case of the vibration under a fixed-end condition when the outer periphery is fixed, the radial mode of n=0, tangential mode, and compound mode of n≧1 are present in the vibration of the resonator body 28 similarly to the disc type resonator 20A in the first embodiment. However, in the case of the above configuration in which the driving electrode 21 and detecting electrode 22 are set to the disc type resonator 20B whose outer periphery is fixed almost in parallel, it is preferable to use the compound mode. In this case, a performance same as the case of open-end condition is obtained for Q value.

Also in the case of this configuration, the detection unit 30 can detect presence or absence of attachment of a substance to a specific region of the resonator body 28 or the quantity of the substance attached to the resonator body 28 with high sensitivity similarly to the case of the above first embodiment by monitoring electrical vibration outputted from the detecting electrode 25.

Moreover, the resonator body 28, and driving electrode 24 and detecting electrode 25 can be electrostatically coupled through faces arranged in almost parallel with each other. Thereby, it is possible to increase a coupling capacity and further increase the driving and detecting efficiencies.

Furthermore, when forming the disc type resonator 20B into a unit, it is possible to conceal the driving electrode 24 and detecting electrode 25 on the back side of the Si layer 27. In the case of the open-end-type disc type resonator 20A shown in the above first embodiment, it is necessary to form a very small gap (for example, approx. 100 nm or less) between the disc type resonator 20A on one hand and the driving electrode 21 and detecting electrode 22 on the other in order to secure the necessary amount of electrostatic coupling. Because of this structure, a substance having a very-small mass or dust, etc. enders the small gap and a situation in which measurement cannot be made may occur. However, in the case of the disc type resonator 20B, it is possible to arrange the driving electrode 24 and detecting electrode 25 on the back side. Therefore, it is possible to avoid the above problem from occurring. Moreover, because only the Si layer 27 is exposed to the outside, it is possible to make the sensor 10 superior in design.

Third Embodiment

Then, a sensor 10 is described which is constituted by electrostatically coupling two disc type resonators 20C and 20D as still another embodiment of the present invention.

Figure 35:
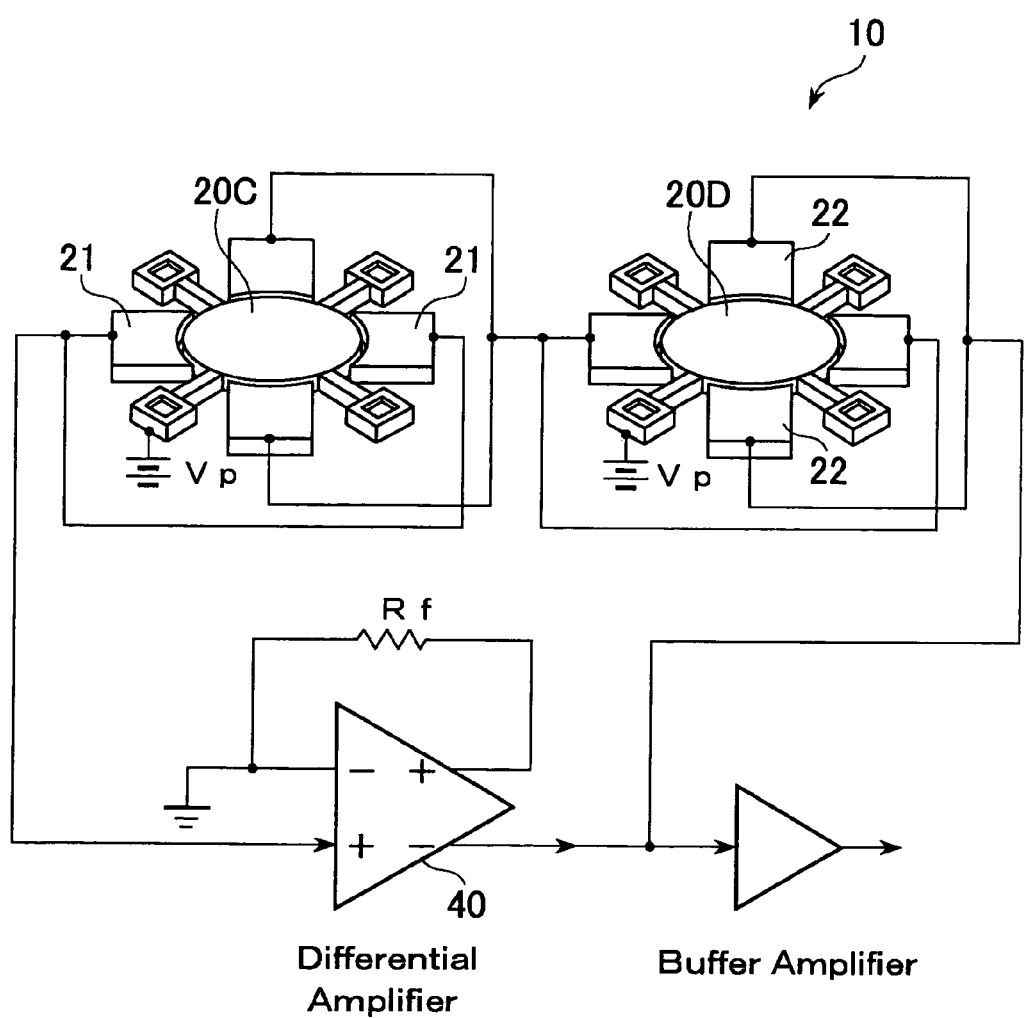
FIG. 35 shows a configuration of the sensor of a third embodiment.

As shown in FIG. 35, the sensor 10 has the disc type resonators 20C and 20D by electrostatically coupling them. In this case, a disc type resonator same as the disc type resonator 20A of the first embodiment is used as an example for the disc type resonators 20C and 20D. However, it is a matter of course that the disc type resonator 20B of the second embodiment can be used.

In the case of this sensor 10, two disc type resonators 20C and 20D are used and a phenomenon is used in which the difference between the vibration frequency specific to each of the disc type resonators 20C and 20D and the frequency changed when the electrostatic coupling between two disc type resonators 20C and 20D acts is changed by a very-small mass attached to specific regions on the surfaces of the disc type resonators 20C and 20D.

In the case of the above configuration, two disc type resonators 20C and 20D which are coupled in accordance with electrostatic coupling are first studied. As to the two disc type resonators 20C and 20D, the vibration frequency of the disc type resonator 20C is determined by expression (9) when n is equal to 2 in accordance with the open-end condition similar to the case of no electrostatic coupling to each other and the state of the vibration is shown by expression (10). Also in this case, the vibration frequency $\omega_0$ is shown by the following expression in accordance with the effective mass $M_{re}$ and effective rigidity $K_{re}$ from the relation same as expressions (12) and (13).

$$\omega_0 = \sqrt{\frac{K_{re}}{M_{re}}} \tag{24}$$

Other disc type resonator 20D is influenced by the electrostatic coupling between the disc type resonators 20C and 20D. When assuming the effective rigidity by the coupling capacity between the two disc type resonators 20C and 20D as $K_{elec}$, the vibration frequency of the other disc type resonator 20D is shown by the following expression.

$$\omega_1 = \omega_0 \sqrt{1 + \frac{2K_{elec}}{K_{re}}} \tag{25}$$

In this case, $K_{elec}$ is shown by the following expression in the case of the vibration of a both-end fixed beam.

$$K_{elec} = -\frac{\varepsilon}{g}\left(\frac{\Delta V_p}{g}\right)^2 \int_0^l \int_0^h U(x, y)^2 \, dx \, dy \tag{26}$$

In this case, $\epsilon$: dielectric constant between resonators, g: distance between resonators, $\Delta V_p$: difference between polarization voltages of resonator: l: length of resonator, and h: thickness of resonator To electrostatically couple the two disc type resonators 20C and 20D, it is only necessary to make the two disc type resonators 20C and 20D approach to each other and stack them. Moreover, it is allowed to couple the two disc type resonators 20C and 20D through an electrostatic coupling electrode. In this case, the above expression (26) is changed to the following expression.

$$K_{elec} = -\frac{\varepsilon}{2g}\left(\frac{\Delta V_p}{2g}\right)\int_0^{2R}\int_0^\alpha U(r,\theta)^2 r\,dr\,d\theta \quad (27)$$

In this case, R: radius of disc type resonators 20C and 20D and $\alpha$: angle of portion coupled with electrostatically-coupling terminal.

The difference $\Delta\omega$ between $\omega_0$ and $\omega_1$ is shown by the following expression in accordance with expressions (24) and (25).

$$\Delta\omega = \omega_0 - \omega_1 \cong \omega_0 \frac{K_{elec}}{K_{re}} = \frac{K_{elec}}{\sqrt{M_{re}K_{re}}} \quad (28)$$

When mass is increased by $\delta m_{re}$ in the disc type resonators 20C and 20D, the difference $\Delta\omega$ of a vibration frequency is shown by the following expression.

$$\delta(\Delta\omega) \cong -\Delta\omega \frac{\delta M_{re}}{2M_{re}} \quad (29)$$

As shown by this expression, when a substance having a mass is similarly added to the mass of the disc type resonators 20C and 20D, the difference between vibration frequencies is changed at the same sensitivity in the disc type resonators 20C and 20D.

Figure 36:
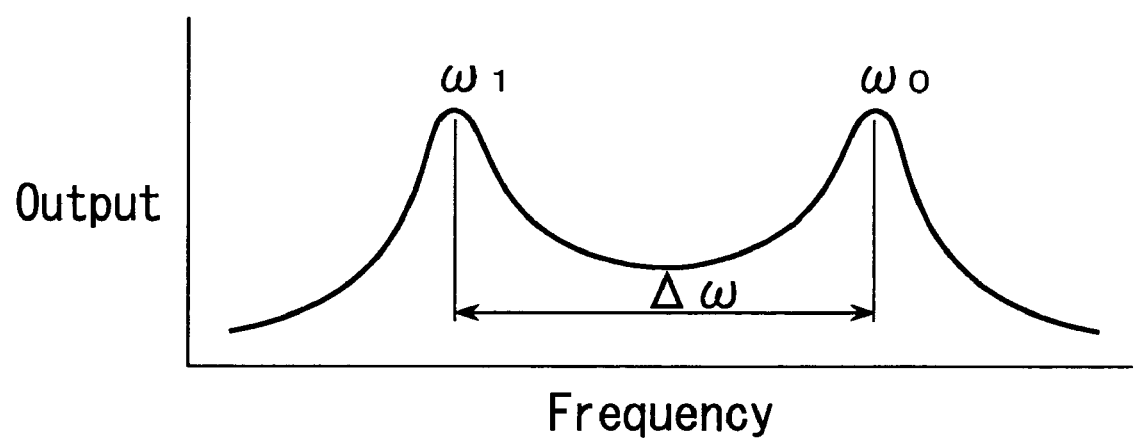
FIG. 36 shows an example of a frequency spectrum obtained by the sensor of the third and fourth embodiments.

The frequency spectrum in this case becomes a frequency spectrum having a peak in two different frequencies as shown in FIG. 36. When constituting a transmitter by using the electrostatically-coupled disc type resonators 20C and 20D as a feedback circuit of a differential amplifier 40 and operating the amplifier so as to be originated by two vibration frequencies $\omega_0$ and $\omega_1$, five frequency spectrums $\omega_0$, $\omega_1$, $\omega_0-\omega_1$, $2\omega_0$, and $2\omega_1$ are observed even if only a secondary nonlinear component having the strongest nonlinearity is taken into consideration because the originating operation of the differential amplifier 40 is a nonlinear operation.

As one of the frequency spectrums, it is possible to directly observe the difference $\Delta\omega=\omega_0-\omega_1$ between the vibration frequencies and easily independently extract the difference $\Delta\omega$ between the vibration frequencies by using a proper low-pass filter. That is, it is possible to directly observe two frequencies generated due to attachment of a minute mass and the difference between the frequencies and easily perform high-sensitivity mass detection. Moreover, the difference $\Delta\omega$ between vibration frequencies has an advantage that the frequency lowers and the processing as a high-frequency circuit is easy.

In the case of the sensor 10 having the configuration, because two disc type resonators 20C and 20D operate in the completely same environment, it can be considered that the resonators receive the same influence due to disturbance. That is, the fluctuation of a frequency due to disturbance is cancelled between the disc type resonators 20C and 20D at the stage of obtaining the difference between vibration frequencies by the detection unit 30. Therefore, the sensor 10 can perform high-accuracy mass detection strong in disturbance in accordance with this configuration.

Fourth Embodiment

Then, a sensor 10 having a configuration for attaching a mass only to one-hand disc type resonator 20F by using two disc type resonators 20E and 20F is described as still another embodiment of the present invention.

Figure 37:
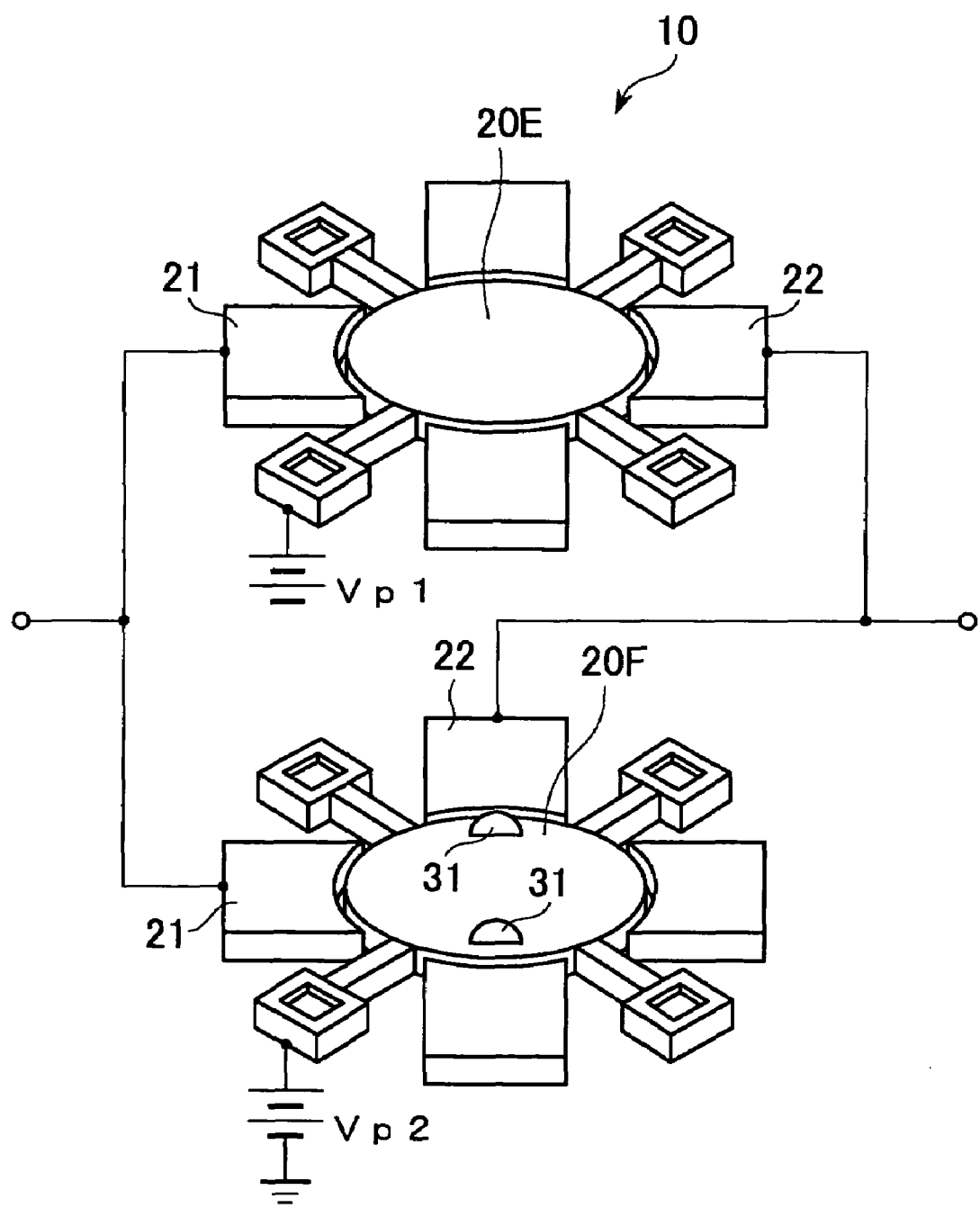
FIG. 37 shows a configuration of the sensor of the fourth embodiment.

As shown in FIG. 37, the sensor 10 has the two disc type resonators 20E and 20F in parallel. The disc type resonators 20E and 20F are respectively set so as to vibrate in the compound mode of n=2, (the so-called wine-glass mode).

The disc type resonators 20E and 20F which vibrate in the wind-glass mode have four coupling electrodes by including the driving electrode 21 and detecting electrode 22, and vibrate in opposite phase to each other in a portion corresponding to electrodes adjacent to each other and in phase in a portion corresponding to electrodes faced each other. Therefore, one-hand disc type resonator 20E is connected as shown in FIG. 37 so that a signal in-phase with a signal input from the driving electrode 21 can be fetched and an opposite-phase signal can be fetched from the other disc type resonator 20F. Thereby, in the detection unit 30, the vibration frequency generated from one-hand disc type resonator 20E and the vibration frequency generated from the other-hand disc type resonator 20F are observed as spectrums.

In the case of the sensor 10, one-hand disc type resonator 20E is covered with a not-illustrated cover so that a substance to be detected does not attach to the resonator 20E as a reference resonator, on the while, it is attached to the other-hand disc type resonator 20F. In this case, when the substance attaches to the disc type resonator 20F and its mass increases by $\delta M_{re}$, only the vibration frequency of the disc type resonator 20F changes as shown in the above expression (14). Because the substance does not attach to the remaining disc type resonator 20E, the vibration frequency is constant. The difference between the frequency of the disc type resonator 20F and the frequency of the disc type resonator 20E whose mass does not change is shown by the following expression.

$$\Delta\omega \approx -\omega_0 \frac{M_{re}}{2M_{re}} \quad (30)$$

By forming a configuration for attaching a substance having a mass only to the other-hand disc type resonator 20F by using two disc type resonators 20E and 20F, a change in vibration frequencies in the disc type resonator 20F is detected by using the disc type resonator 20E as a reference. Moreover, one-hand disc type resonator 20E and the other-hand disc type resonator 20F are connected so that phases of two vibration frequencies become in-phase and at the same time, vibrate in two different frequencies. In these two frequencies, the amplitude is attenuated to the frequency in one-hand disc type resonator 20E and the amplitude is increased in the other-hand disc type resonator 20F. Because the phase when the amplitude increases and the phase when the amplitude attenuates become an opposite-phase state, a deep spectrum trough is formed between two frequencies. That is, by clarifying the difference between two frequencies, it is possible to detect a mass with high-sensitivity.

Figure 5:
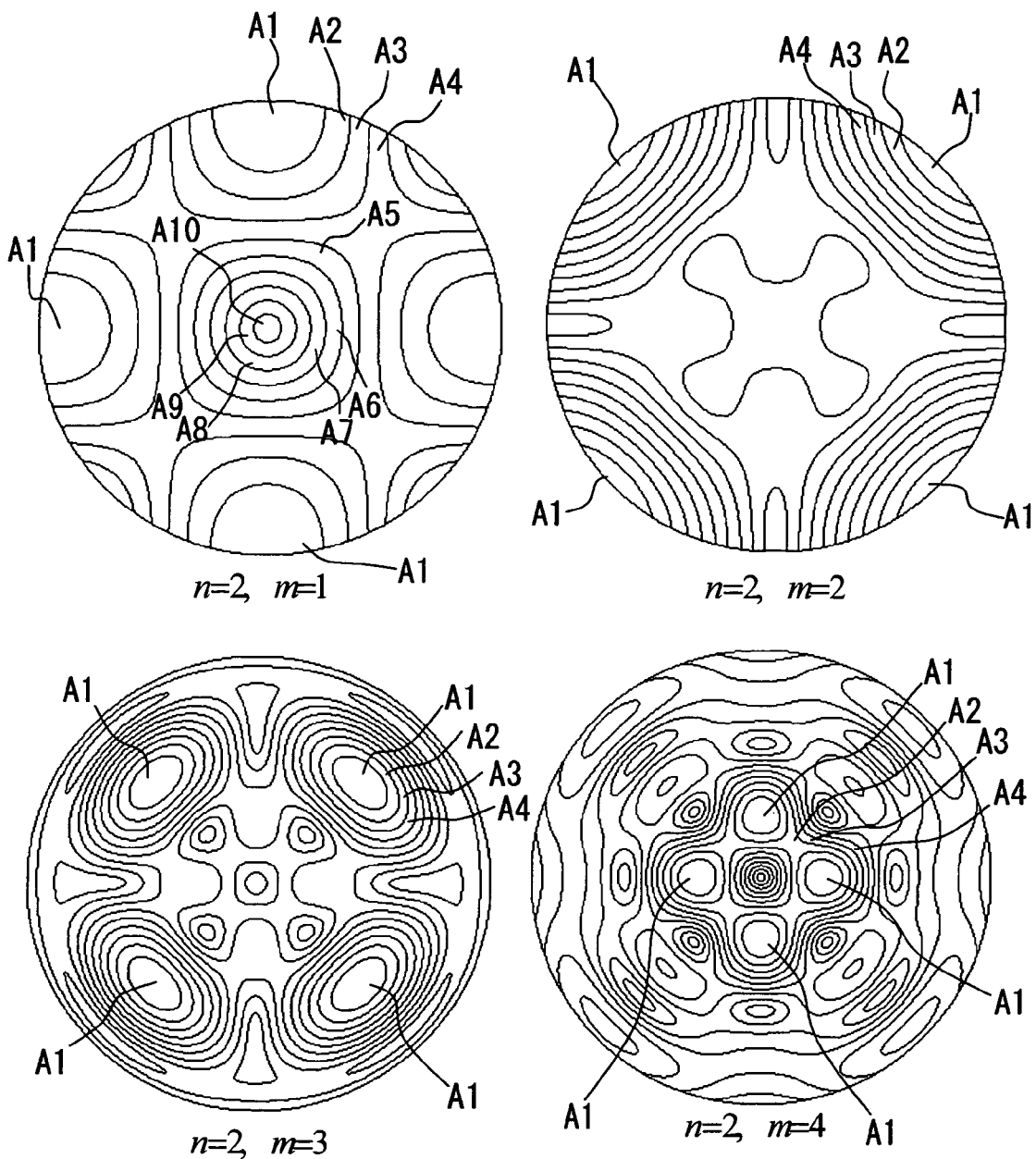
FIG. 5 similarly shows a distribution of the vibration amplitude of a disc type resonator in the compound mode, vibration mode n=2, and harmonic vibration order m=1, 2, 3 and 4.
Figure 6:
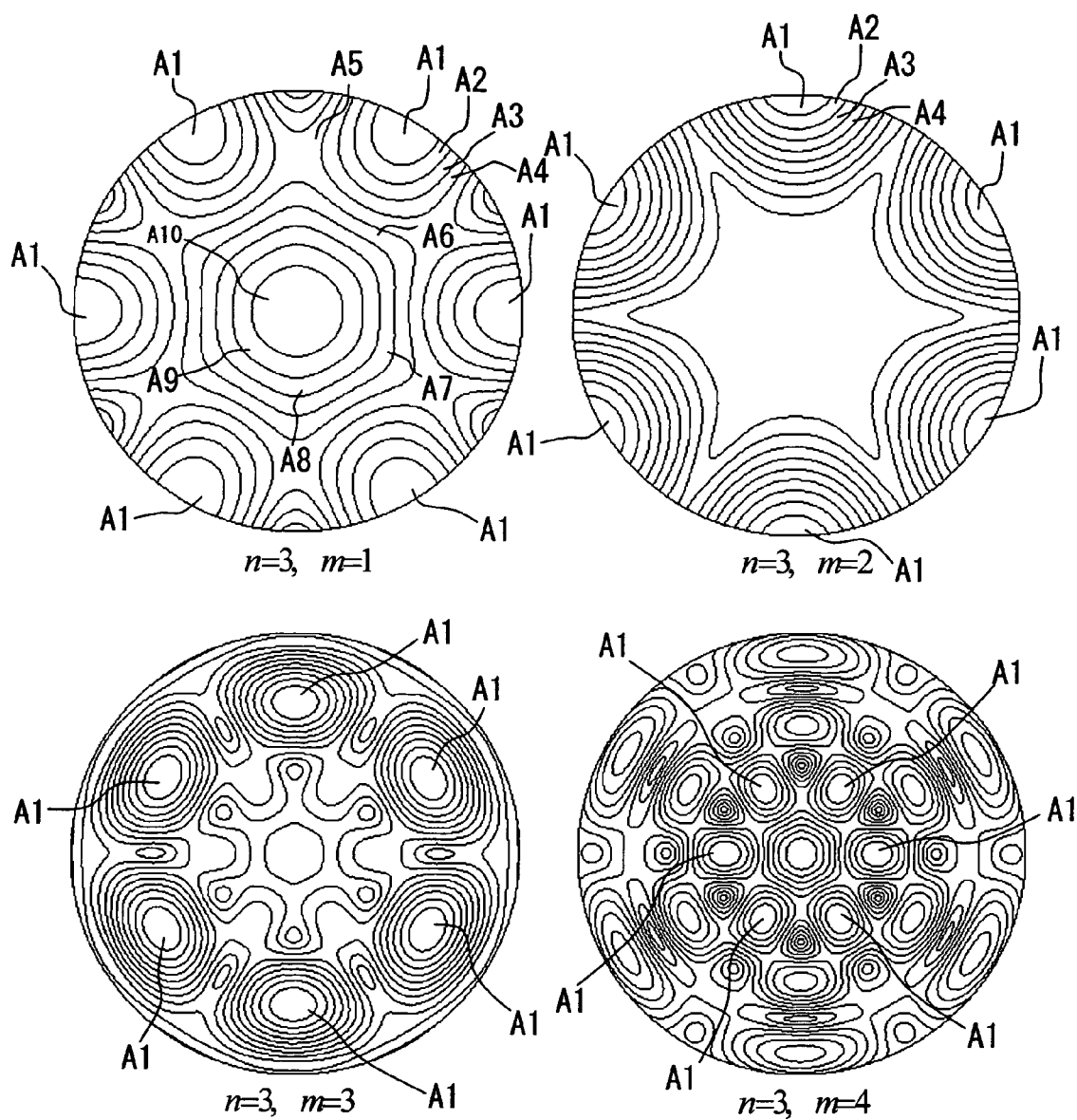
FIG. 6 similarly shows a distribution of the vibration amplitude of a disc type resonator in the compound mode, vibration mode n=3, and harmonic vibration order m=1, 2, 3 and 4.
Figure 7:
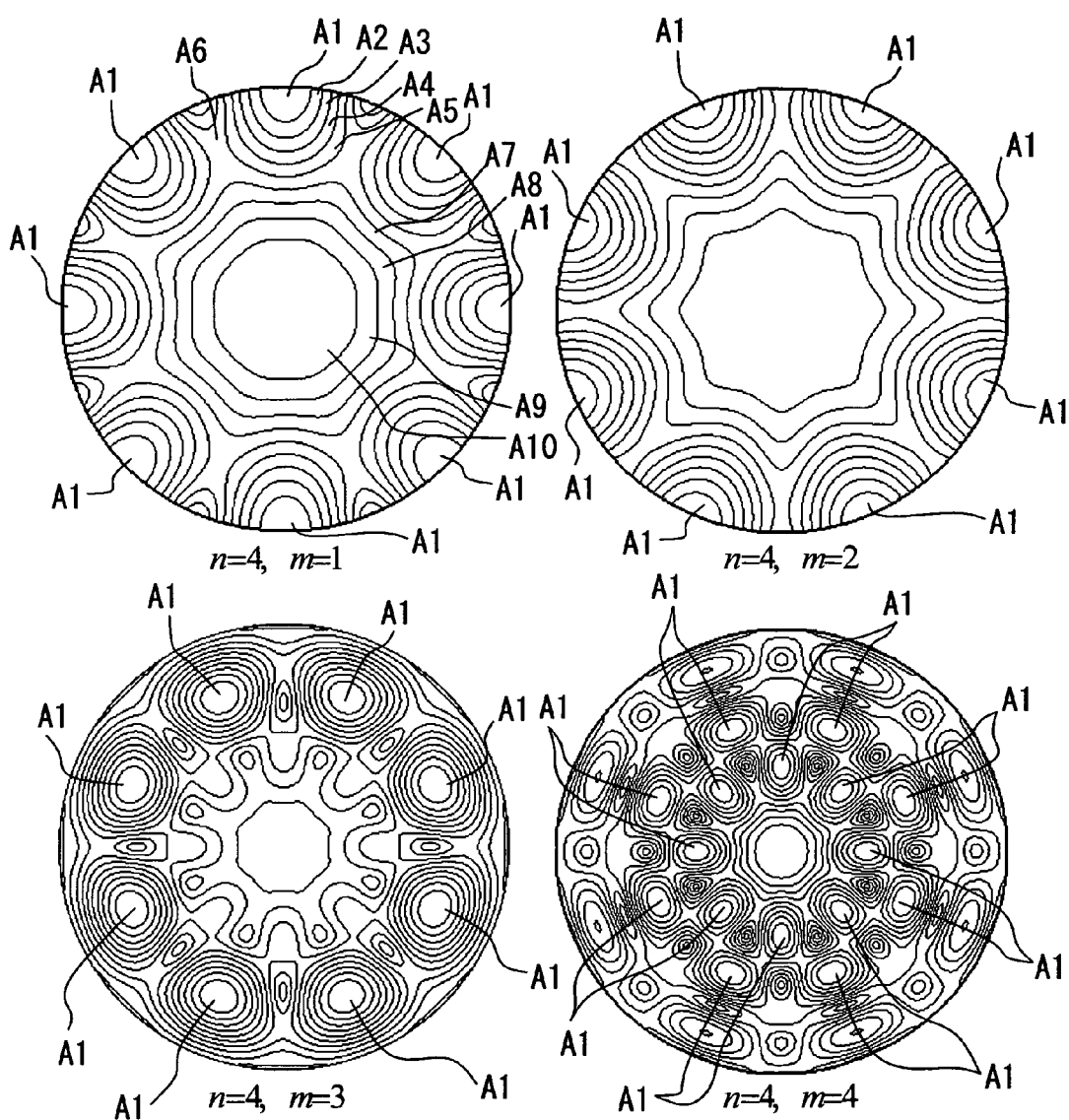
FIG. 7 similarly shows a distribution of the vibration amplitude of a disc type resonator in the compound mode, vibration mode n=4, and harmonic vibration order m=1, 2, 3 and 4.
Figure 8B:
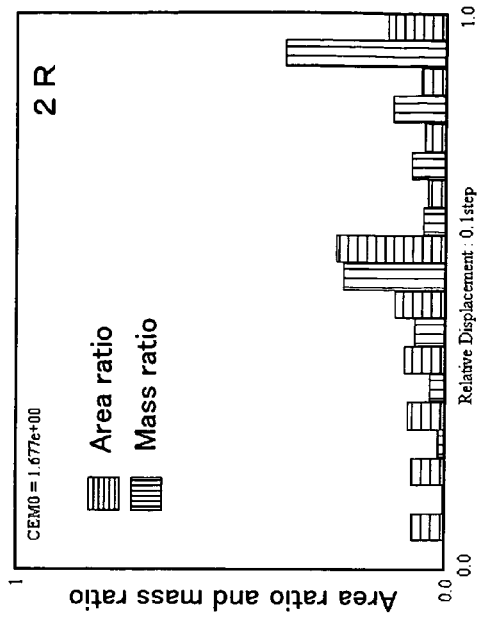
FIGS. 8A to 8D show the mass ratio between the effective mass occupied by one of the region separated into 10 stages and all effective masses and the area ratio between the area of the region and all the surface area of a resonator, from the largest vibration amplitude in order, when a resonator vibrates in the radial mode, vibration mode n=0, and harmonic vibration order m=1, 2, 3 and 4.
Figure 8D:
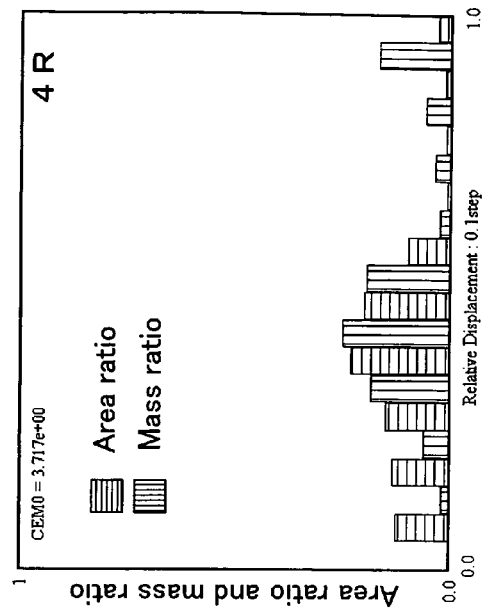
Figure 8A:
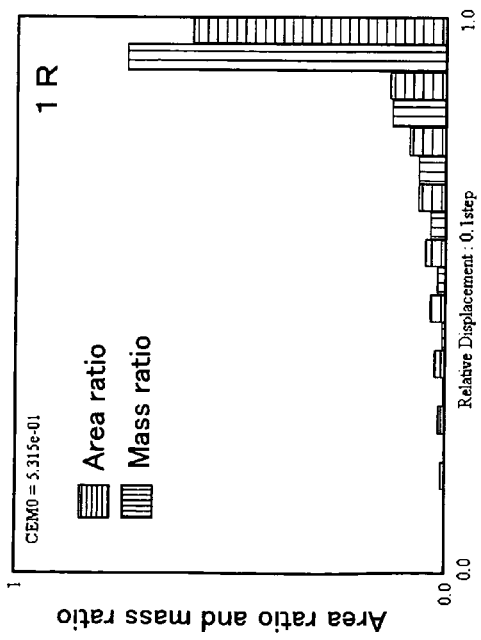
Figure 8C:
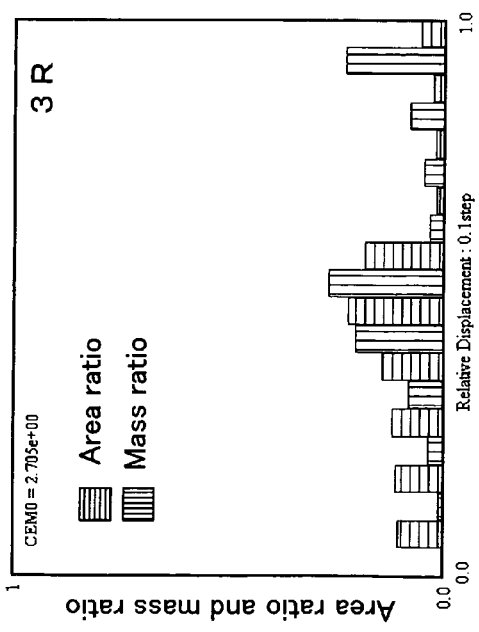
Figure 9A:
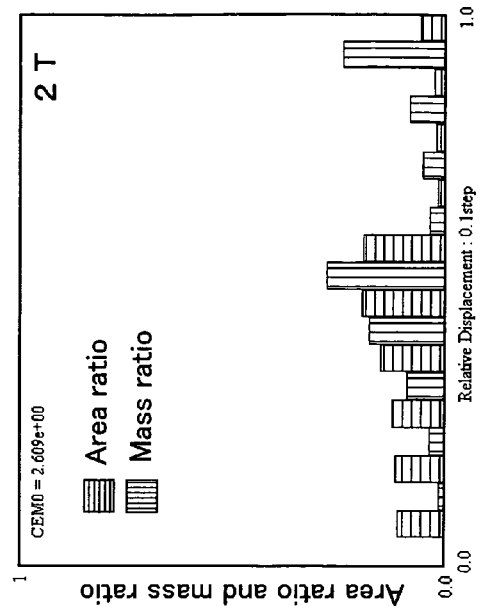
FIGS. 9A to 9D similarly show the mass ratio and the area ratio when a resonator vibrates in the tangential mode, vibration mode n=0, and harmonic vibration order m=1, 2, 3 and 4.
Figure 9B:
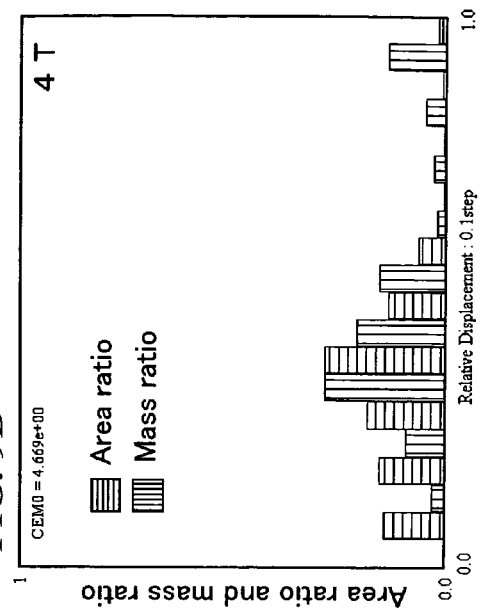
Figure 9C:
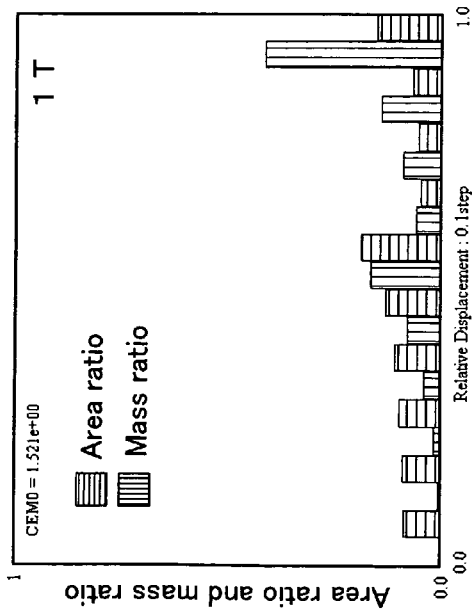
Figure 9D:
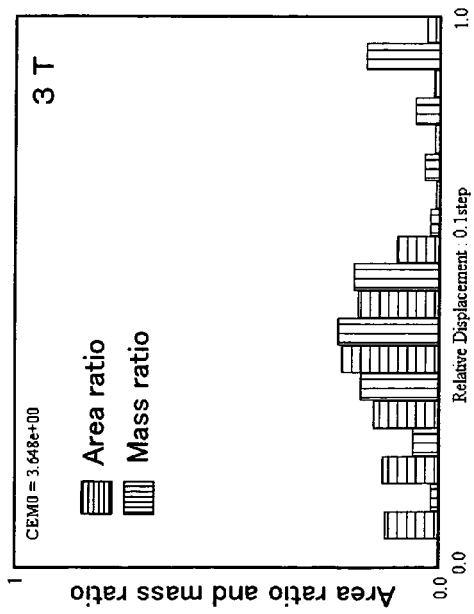
Figure 10A:
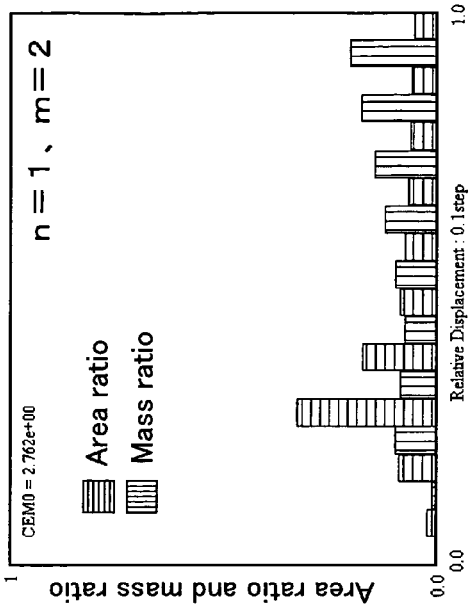
FIGS. 10A to 10D similarly show the mass ratio and the area ratio when a resonator is vibrated in the compound mode, vibration mode n=1, and harmonic vibration order m=1, 2, 3 and 4.
Figure 10B:
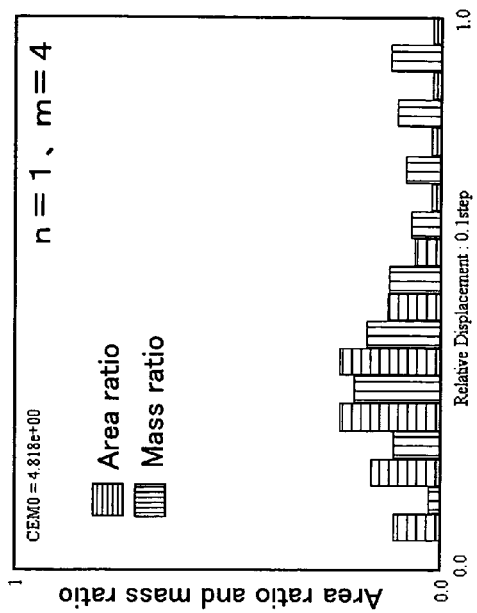
Figure 10C:
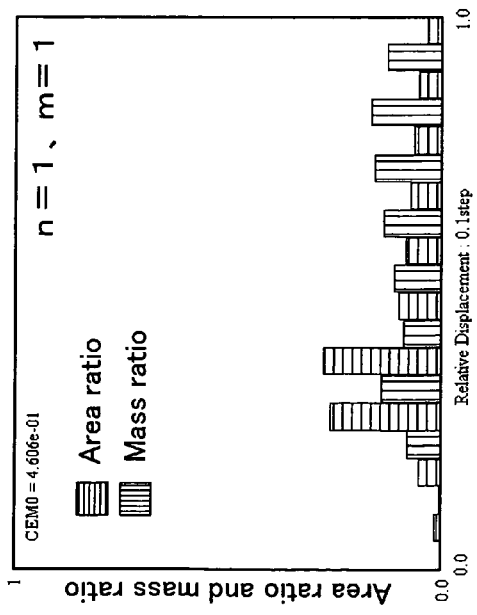
Figure 10D:
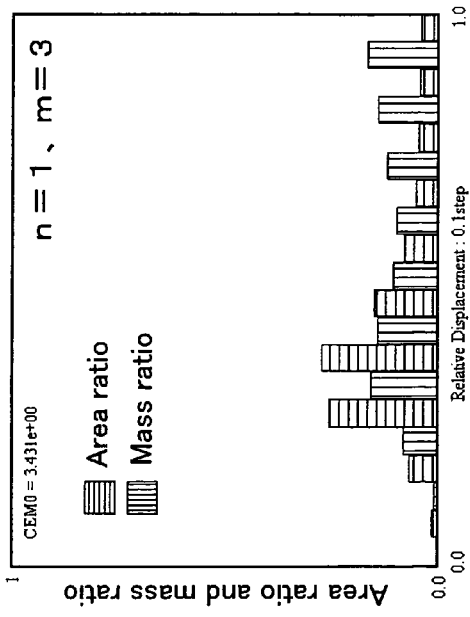
Figure 11A:
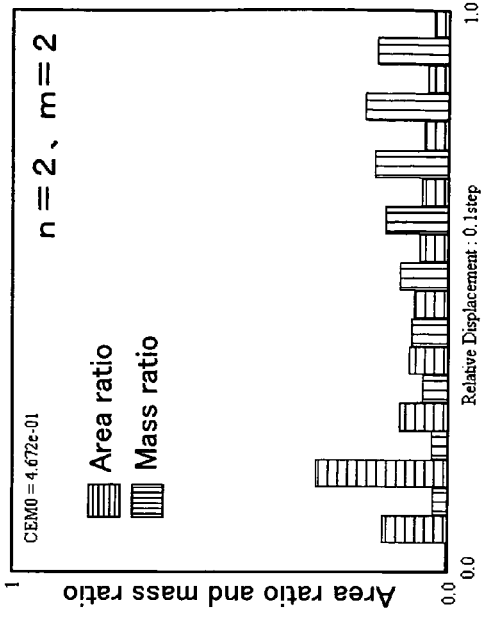
FIGS. 11A to 11D similarly show the mass ratio and the area ratio when a resonator vibrates in the compound mode, vibration mode n=2, and harmonic vibration order m=1, 2, 3 and 4.
Figure 11B:
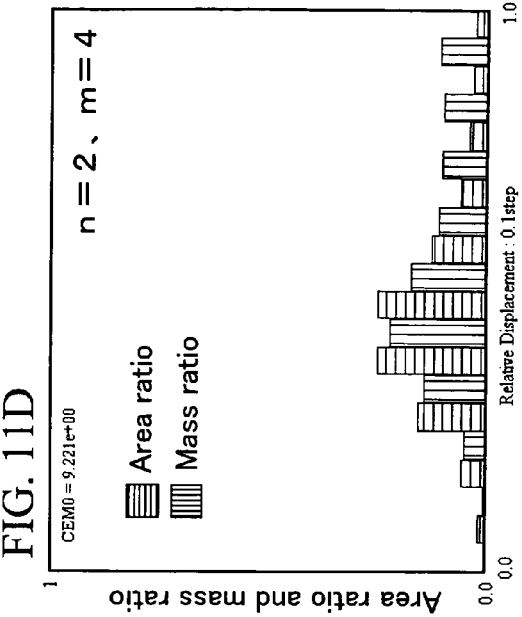
Figure 11C:
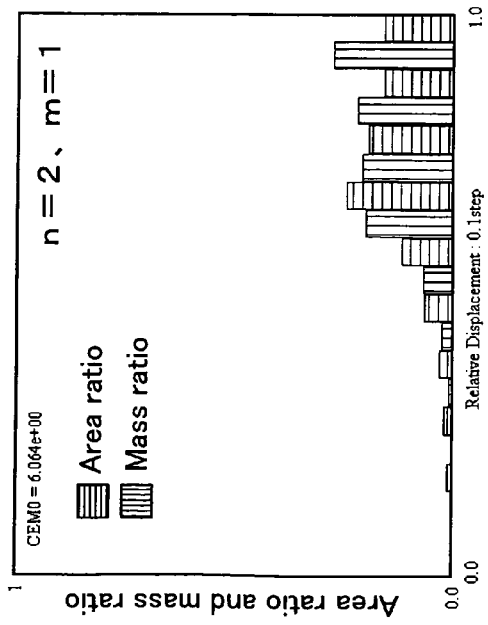
Figure 11D:
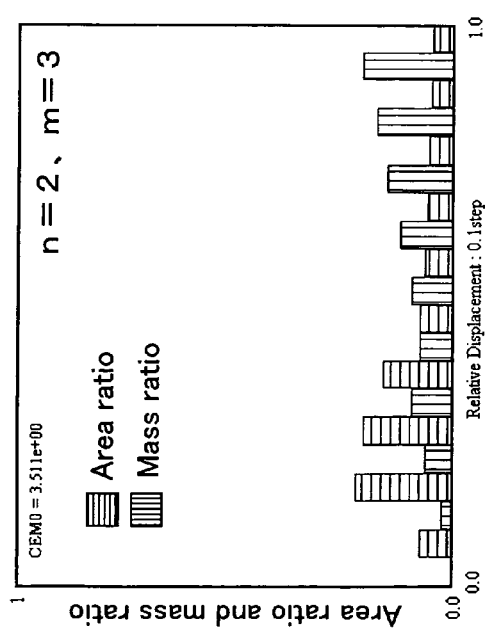
Figure 12B:
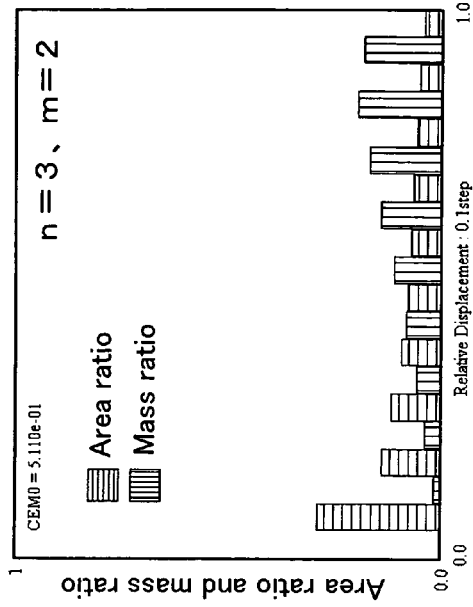
FIGS. 12A to 12D similarly show the mass ratio and the area ratio when a resonator vibrates in the compound mode, vibration mode n=3, and harmonic vibration order m=1, 2, 3 and 4.
Figure 12D:
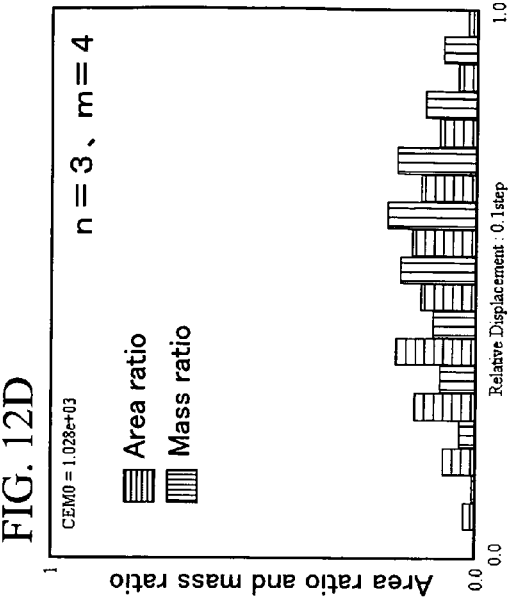
Figure 12A:
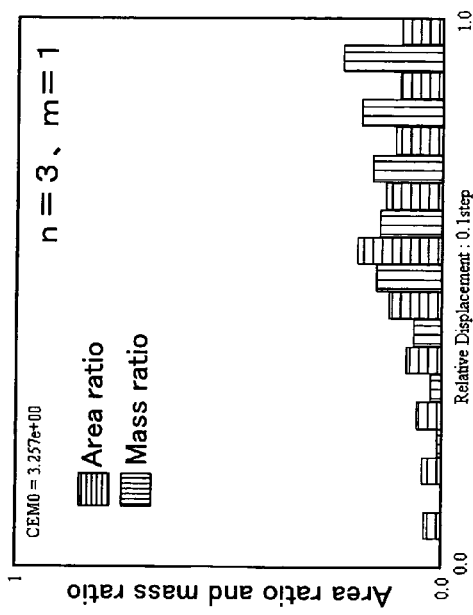
Figure 12C:
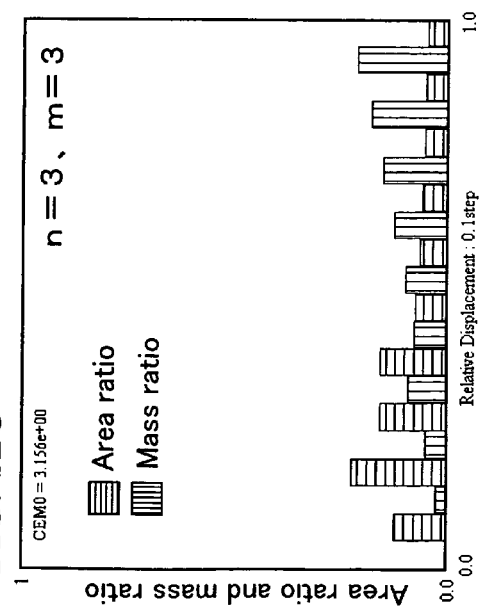
Figure 13A:
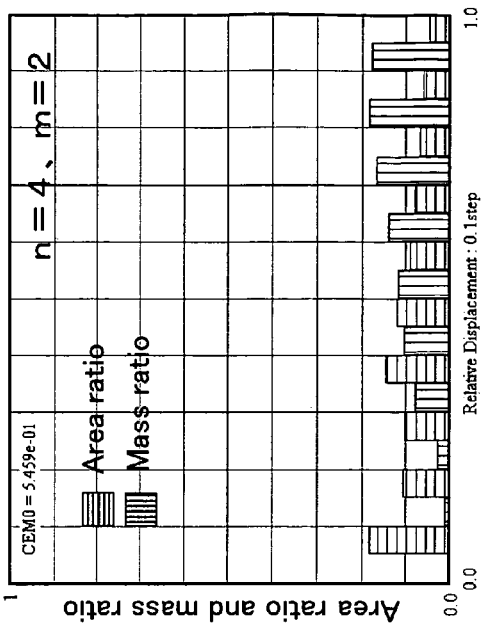
FIGS. 13A to 13D similarly show the mass ratio and the area ratio when a resonator vibrates in the compound mode, vibration mode n=4, and harmonic vibration order m=1, 2, 3 and 4.
Figure 13B:
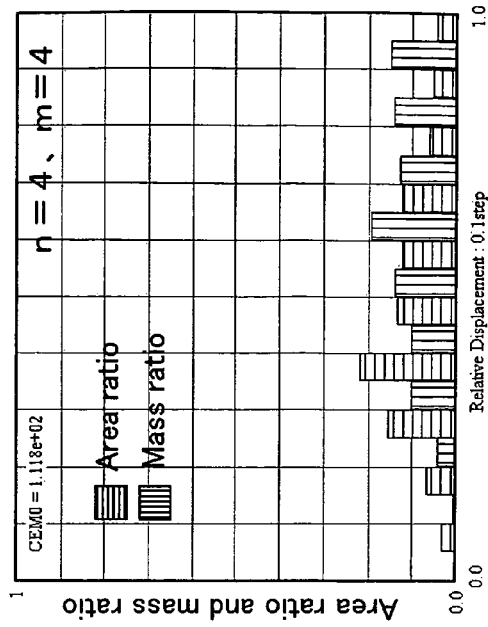
Figure 13C:
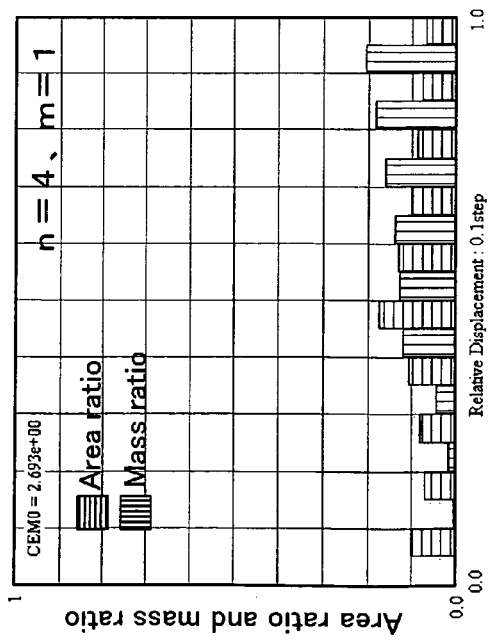
Figure 13D:
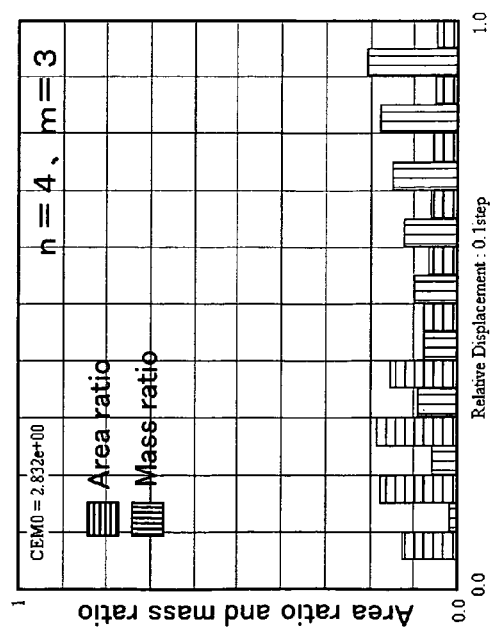
Figure 14:
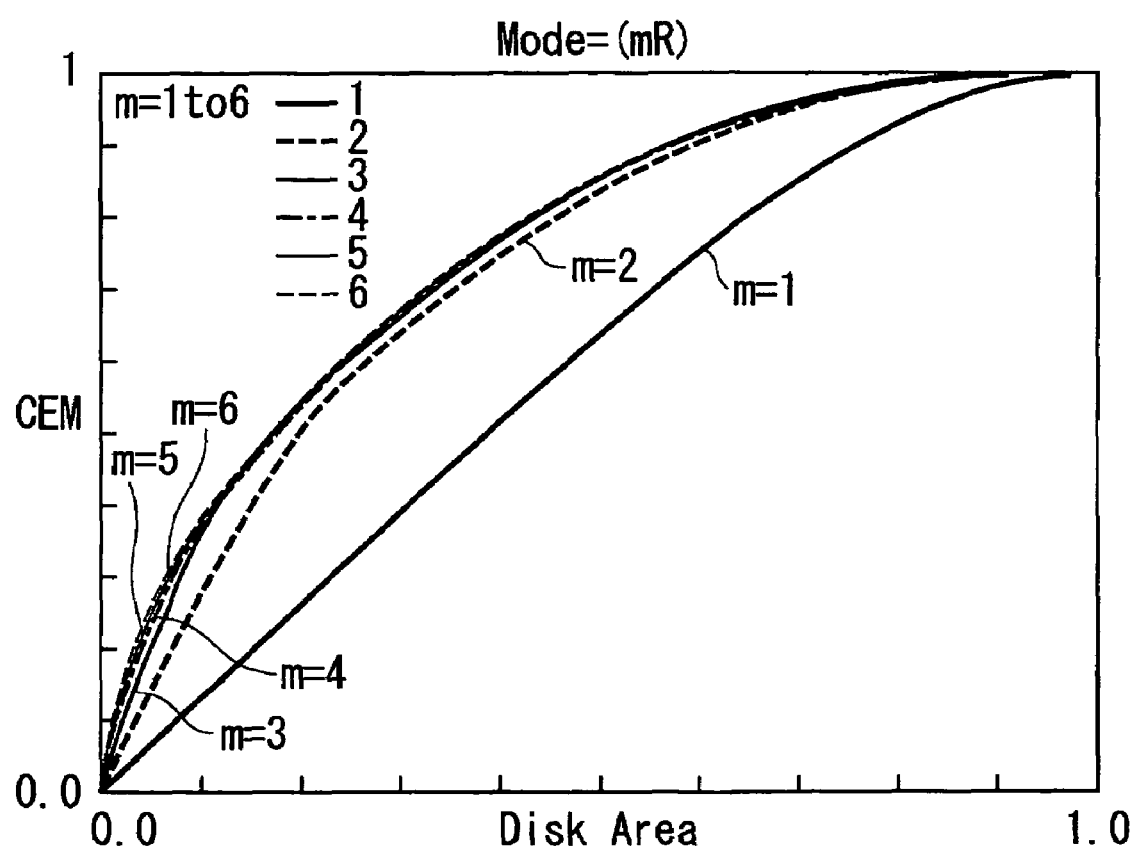
FIG. 14 shows the relation between the rate of the accumulated effective mass obtained by sequentially adding the effective mass in descending order of regions having larger vibration amplitude to the whole effective mass of the disc type resonator and a rate (area ratio) of the accumulated area obtained by sequentially adding areas for each region to the whole area of the disc type resonator, when a resonator is vibrated in the radial mode, vibration mode n=0, and harmonic vibration order m=1 to 6.
Figure 15:
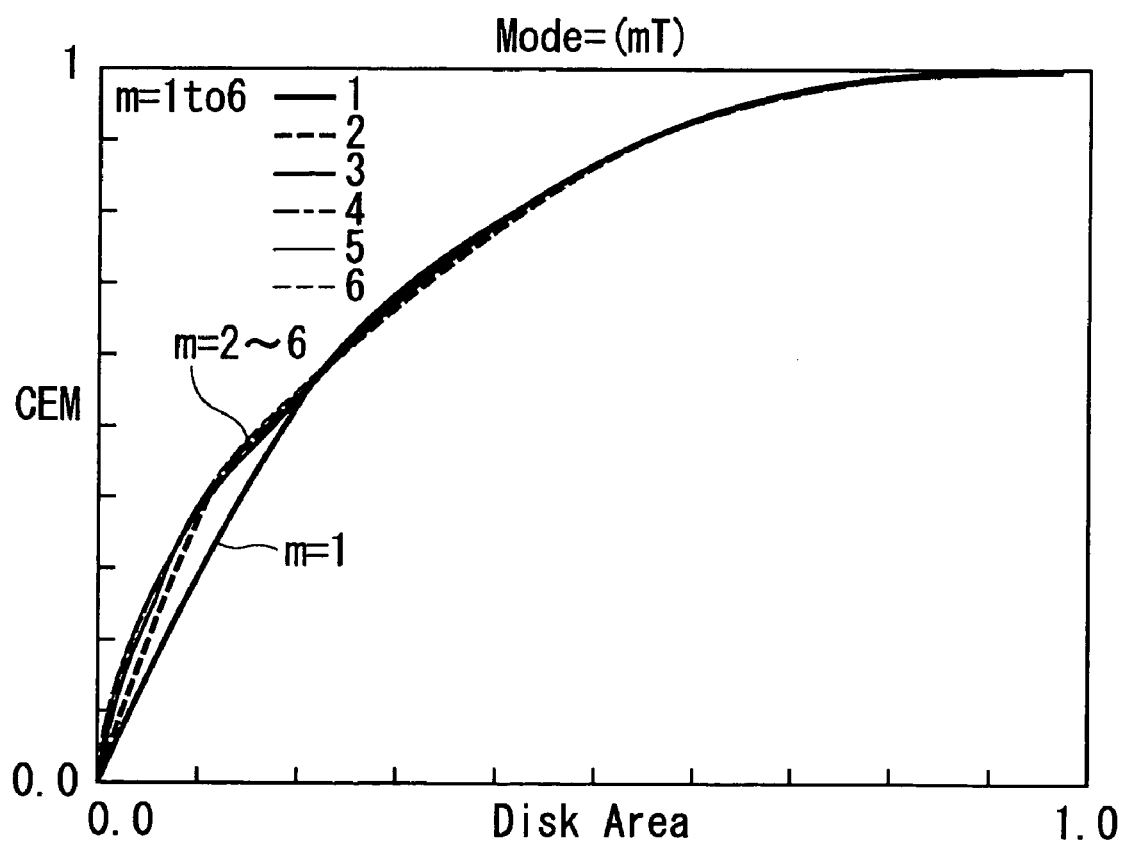
FIG. 15 similarly shows the relation between the rate of the accumulated effective mass and the rate of the accumulated area when a resonator vibrates in the tangential mode, vibration mode n=0, and harmonic vibration order m=1 to 6.
Figure 16:
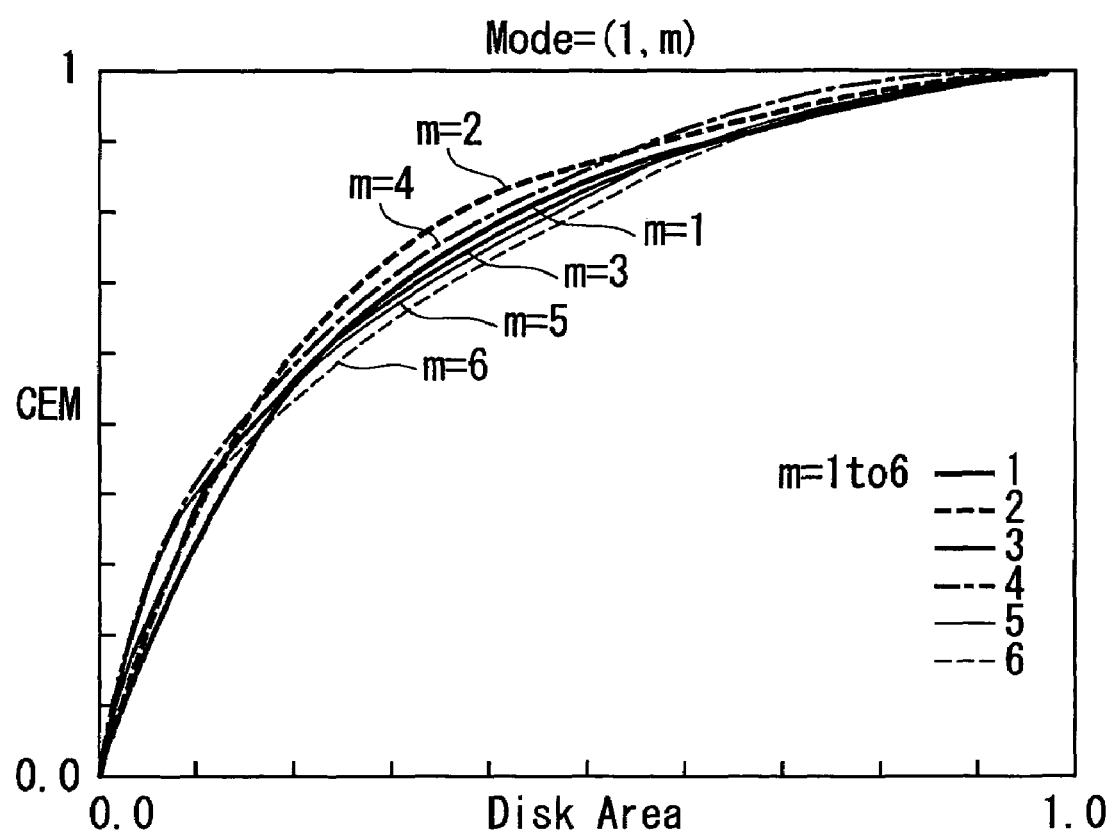
FIG. 16 similarly shows the relation between the rate of the accumulated effective mass and the rate of the accumulated area when a resonator is vibrated in the compound mode, vibration mode n=1, and harmonic vibration order m=1 to 6.
Figure 17:
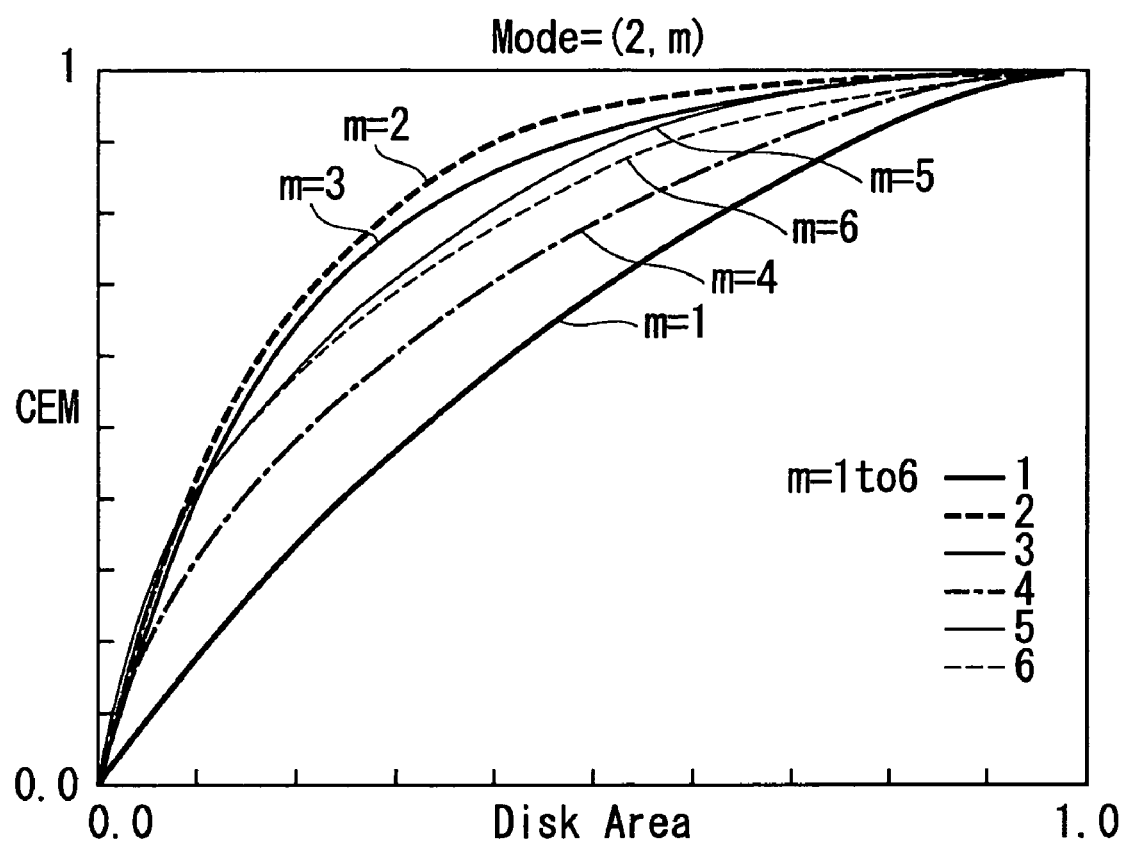
FIG. 17 similarly shows the relation between the rate of the accumulated effective mass and the rate of the accumulated area when a resonator vibrates in the compound mode, vibration mode n=2, and harmonic vibration order m=1 to 6.
Figure 18:
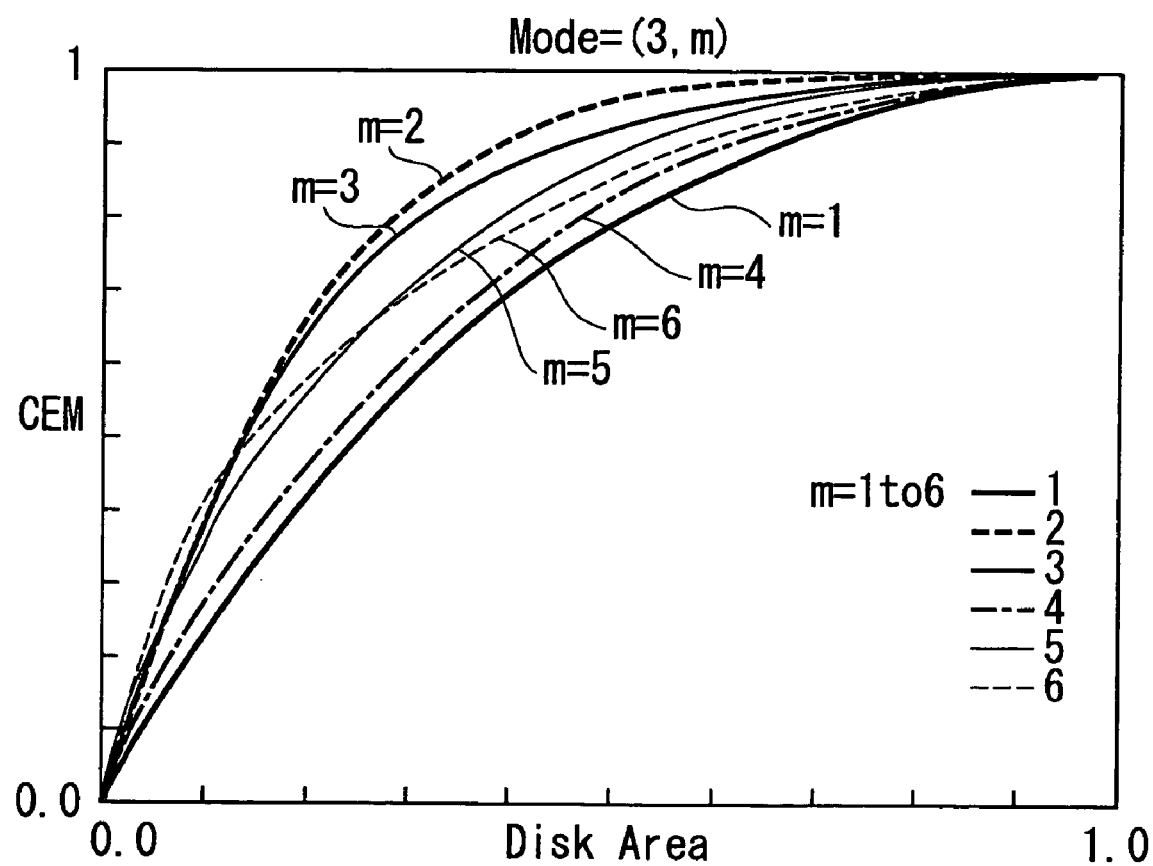
FIG. 18 similarly shows the relation between the rate of the accumulated effective mass and the rate of the accumulated area when a resonator vibrates in the compound mode, vibration mode n=3, and harmonic vibration order m=1 to 6.
Figure 19:
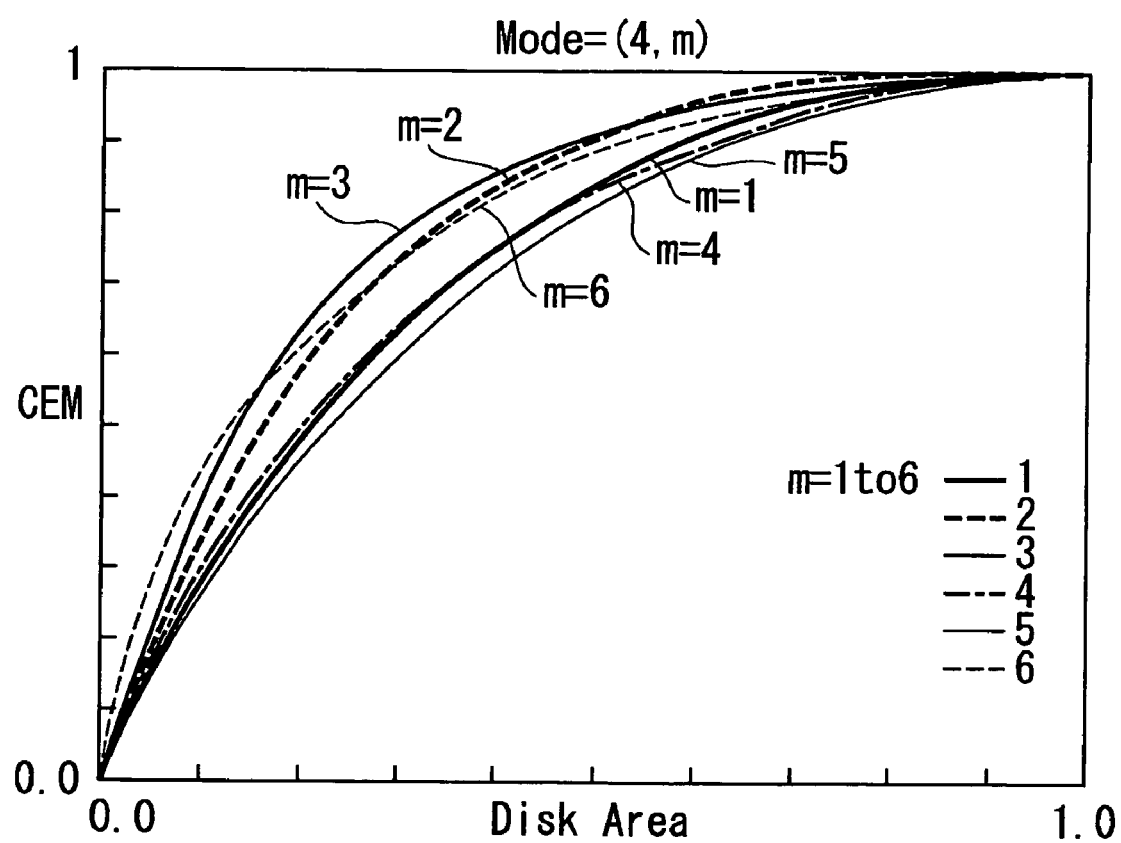
FIG. 19 similarly shows the relation between the rate of the accumulated effective mass and the rate of the accumulated area when a resonator vibrates in the compound mode, vibration mode n=4, and harmonic vibration order m=1 to 6.
Figure 20:
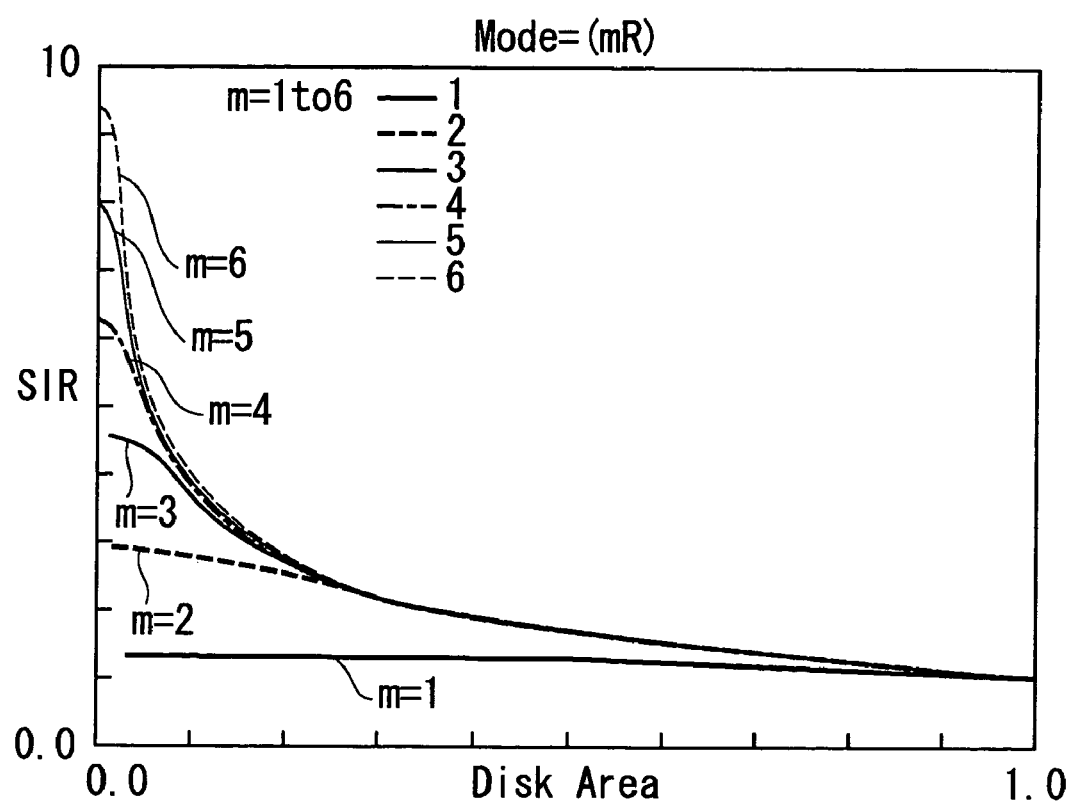
FIG. 20 shows a sensitivity improve ratio SIR resulting from attaching a very-small substance to the specific surface of a resonator, when a resonator vibrates in the radial mode, vibration mode n=0, and harmonic vibration order m=1 to 6.
Figure 21:
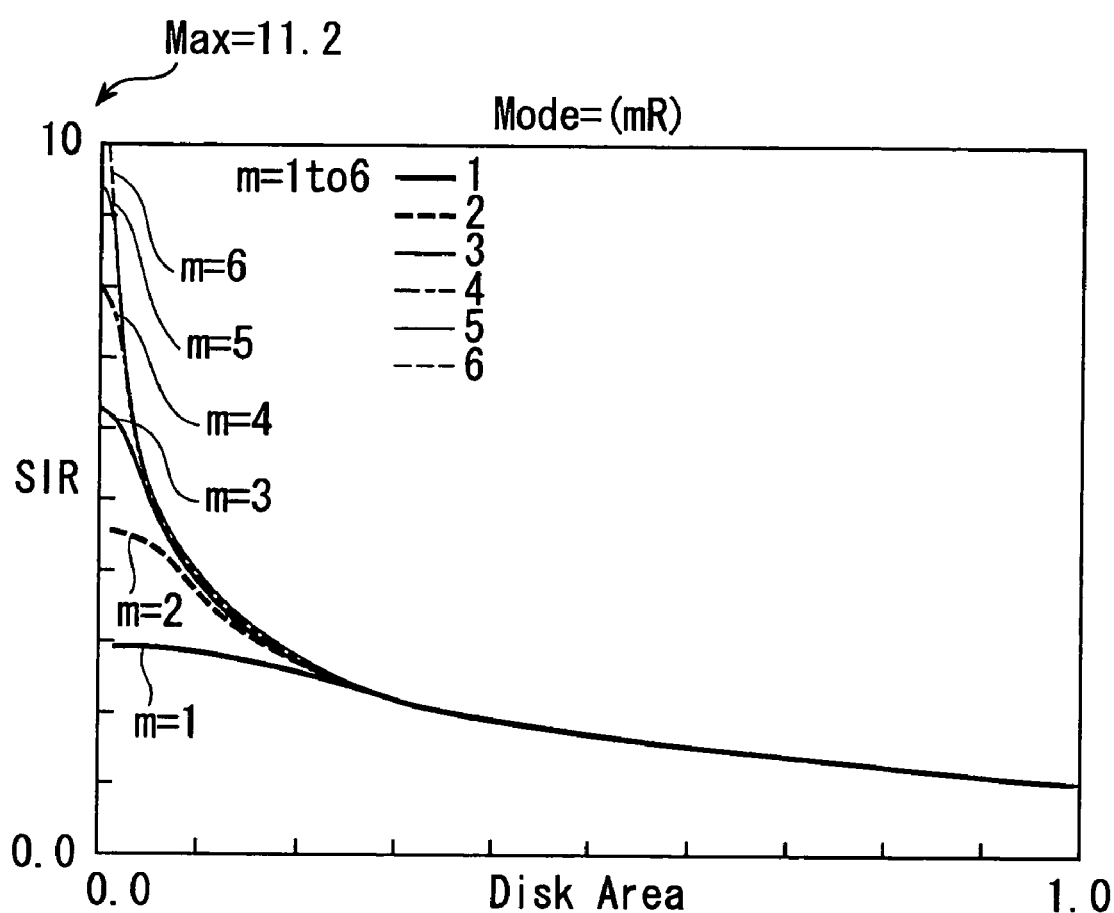
FIG. 21 similarly shows a sensitivity improve ratio SIR when a resonator vibrates in the tangential mode, vibration mode n=0, and harmonic vibration order m=1 to 6.
Figure 22:
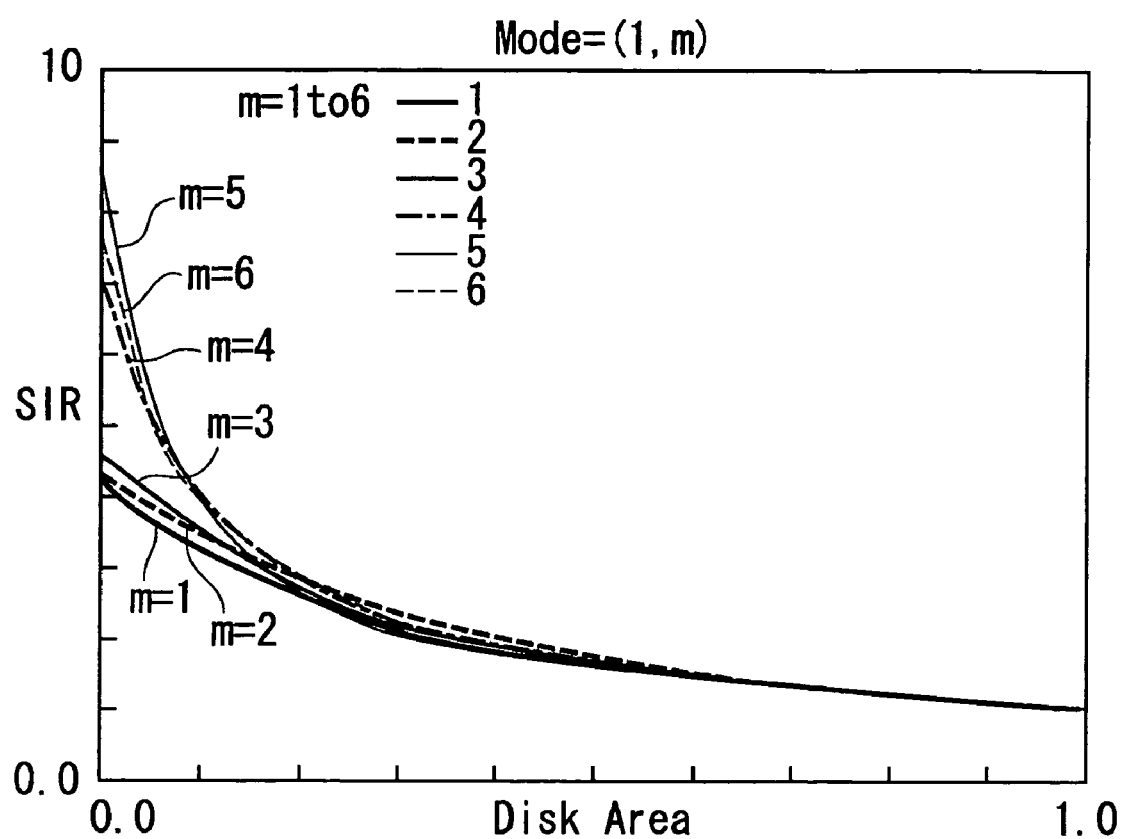
FIG. 22 similarly shows a sensitivity improve ratio SIR when a resonator vibrates in the compound mode, vibration mode n=1, and harmonic vibration order m=1 to 6.
Figure 23:
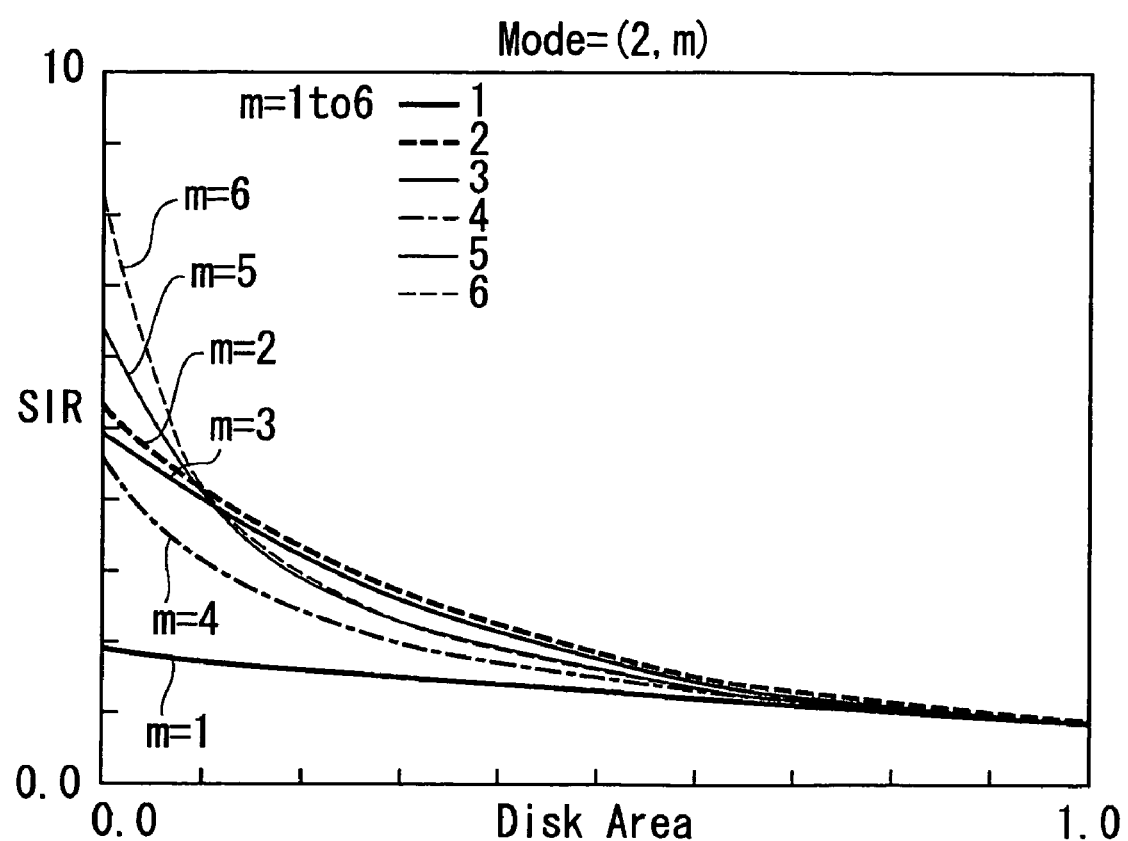
FIG. 23 similarly shows a sensitivity improve ratio SIR when a resonator vibrates in the compound mode, vibration mode n=2, and harmonic vibration order m=1 to 6.
Figure 24:
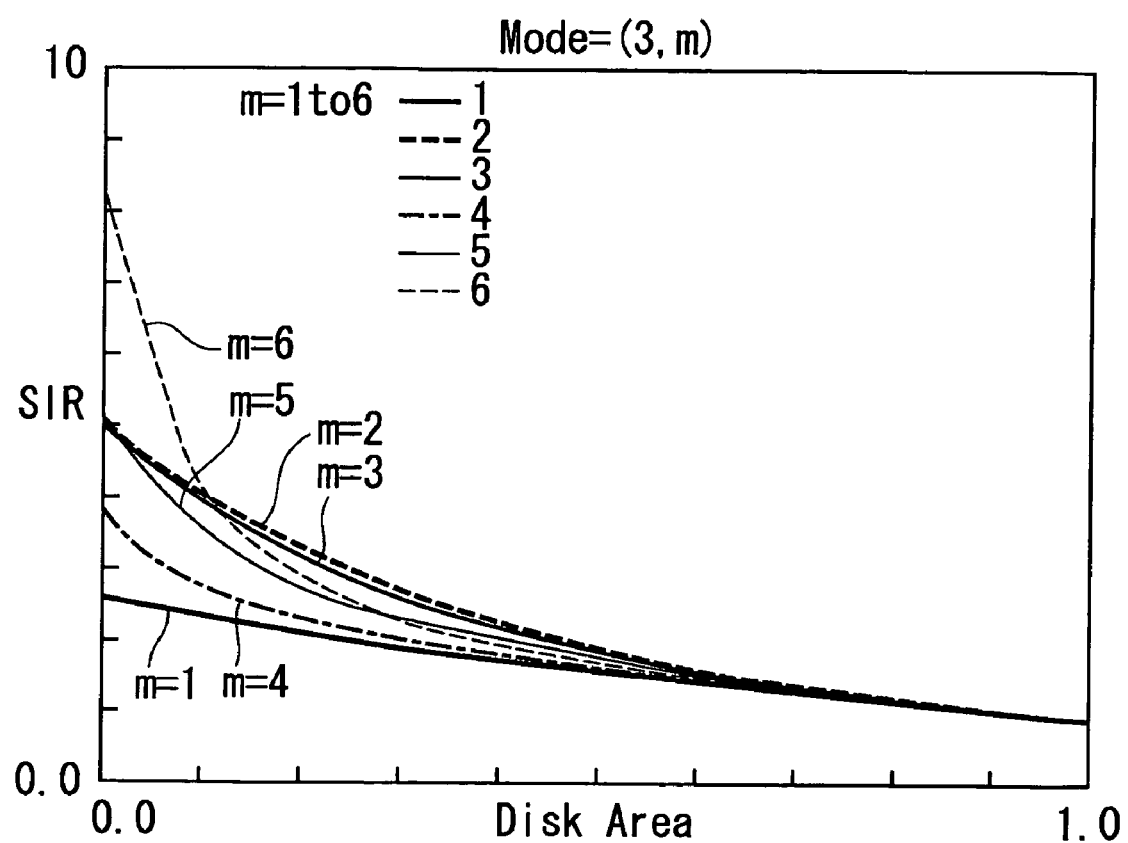
FIG. 24 similarly shows a sensitivity improve ratio SIR when a resonator vibrates in the compound mode, vibration mode n=3, and harmonic vibration order m=1 to 6.
Figure 25:
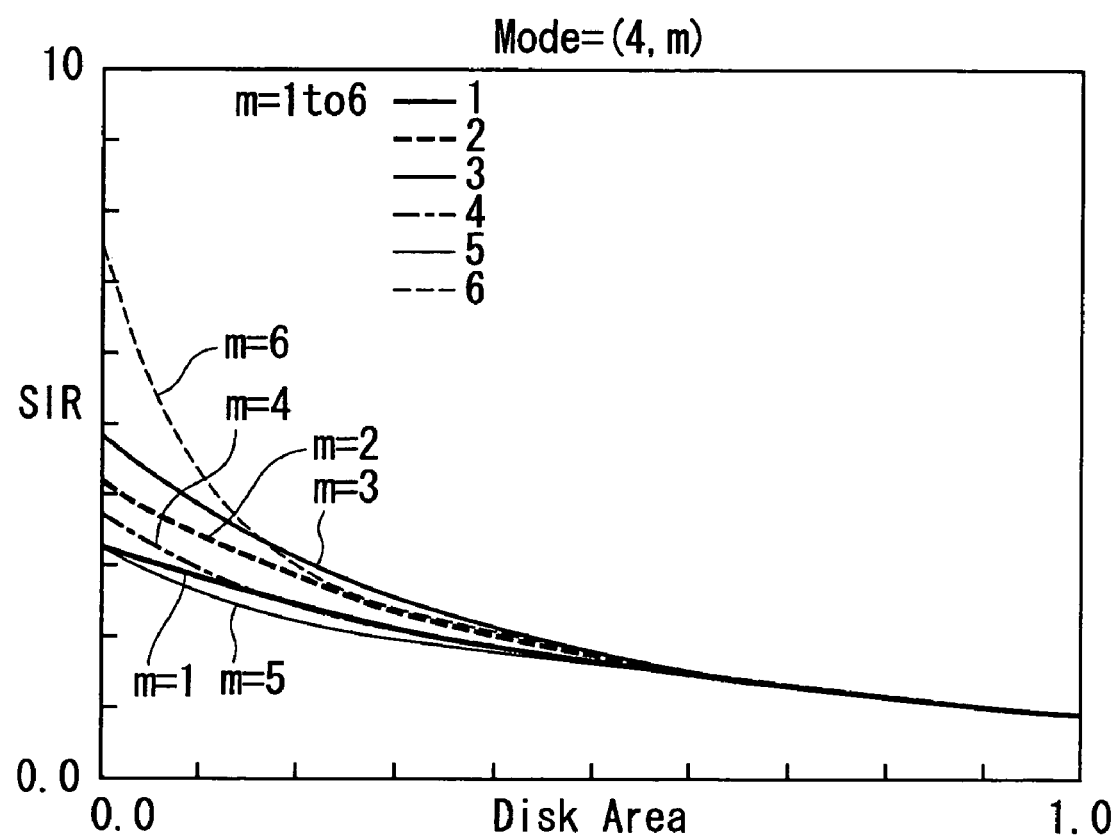
FIG. 25 similarly shows a sensitivity improve ratio SIR when a resonator vibrates in the compound mode, vibration mode n=4, and harmonic vibration order m=1 to 6.
Figure 26:
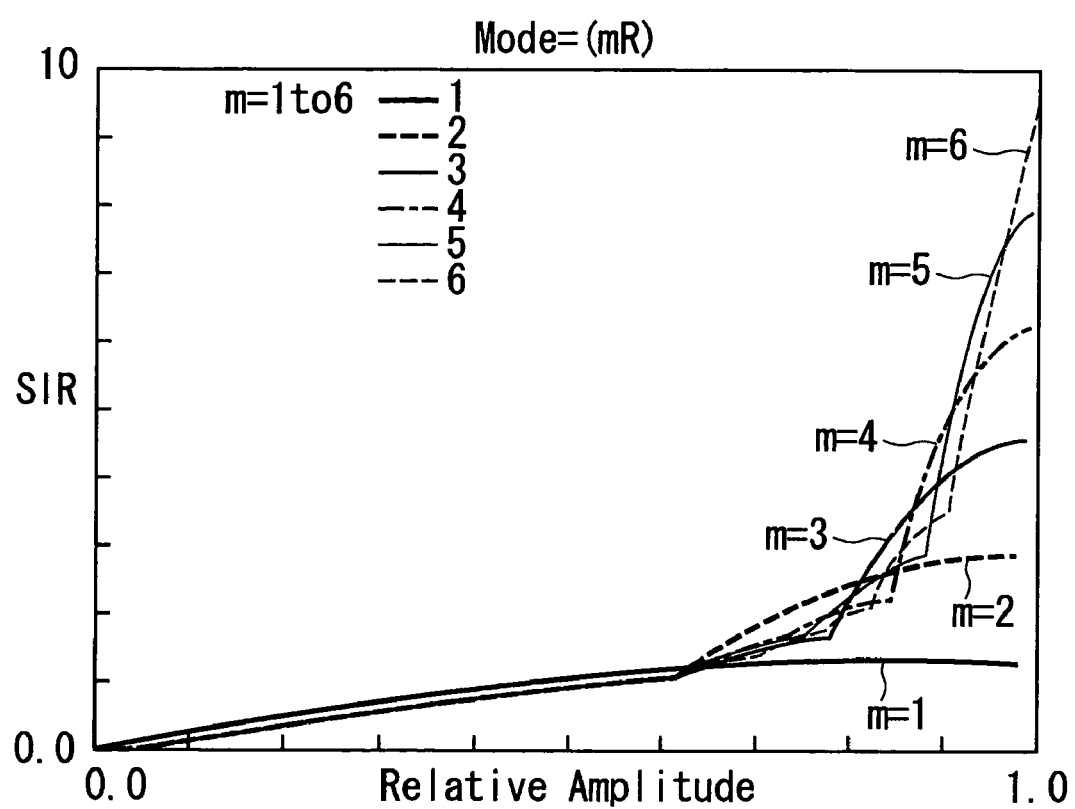
FIG. 26 shows the relation between standardized vibration amplitude when assuming the maximum amplitude is 1 and the sensitivity improve ratio (SIR) of detection sensitivity, when a resonator vibrates in the radial mode, vibration mode n=0, and harmonic vibration order m=1 to 6.
Figure 27:
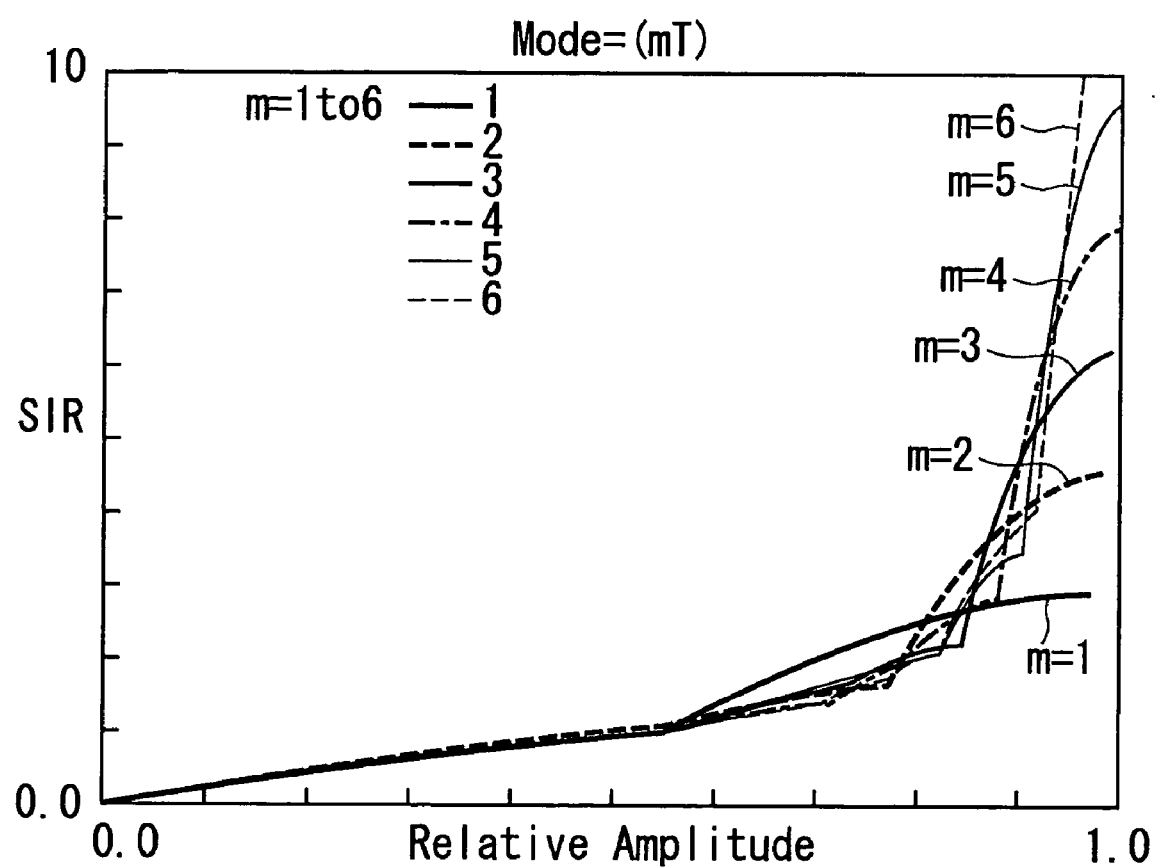
FIG. 27 similarly shows the relation between the standardized vibration amplitude and the sensitivity improve ratio (SIR) when a resonator vibrates in the tangential mode, vibration mode n=0, and harmonic vibration order m=1 to 6.
Figure 28:
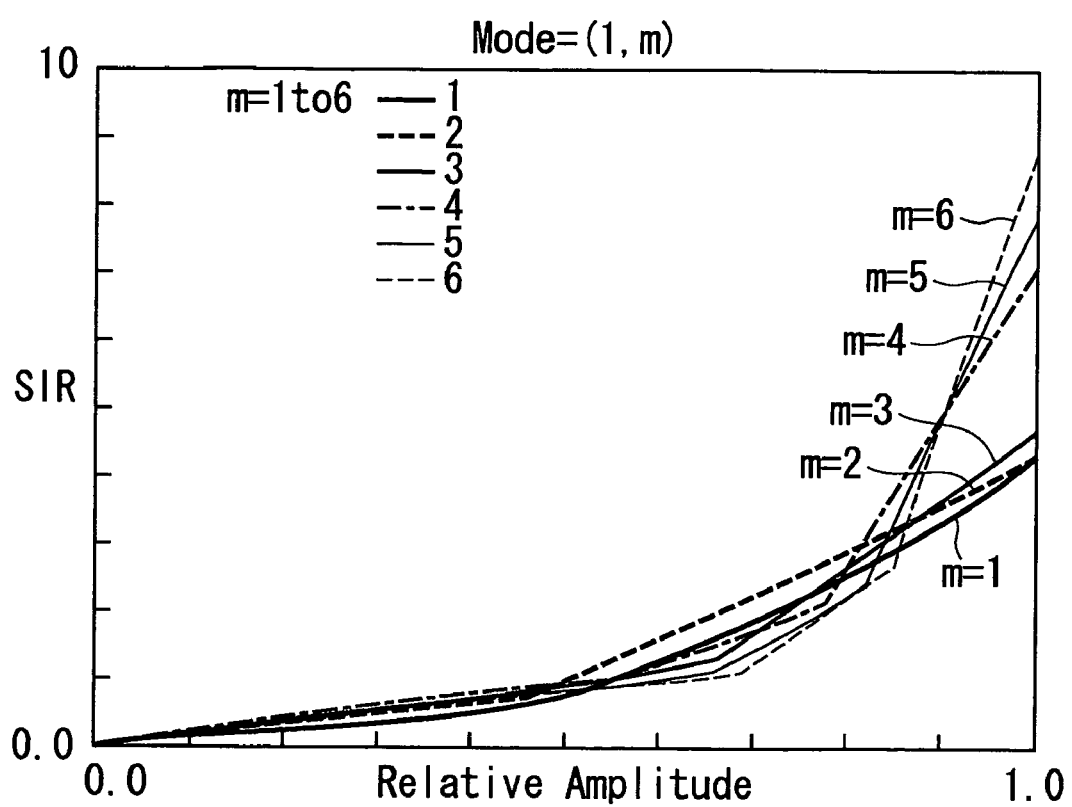
FIG. 28 similarly shows the relation between the standardized vibration amplitude and the sensitivity improve ratio (SIR) when a resonator vibrates in the compound mode, vibration mode n=1, and harmonic vibration order m=1 to 6.
Figure 29:
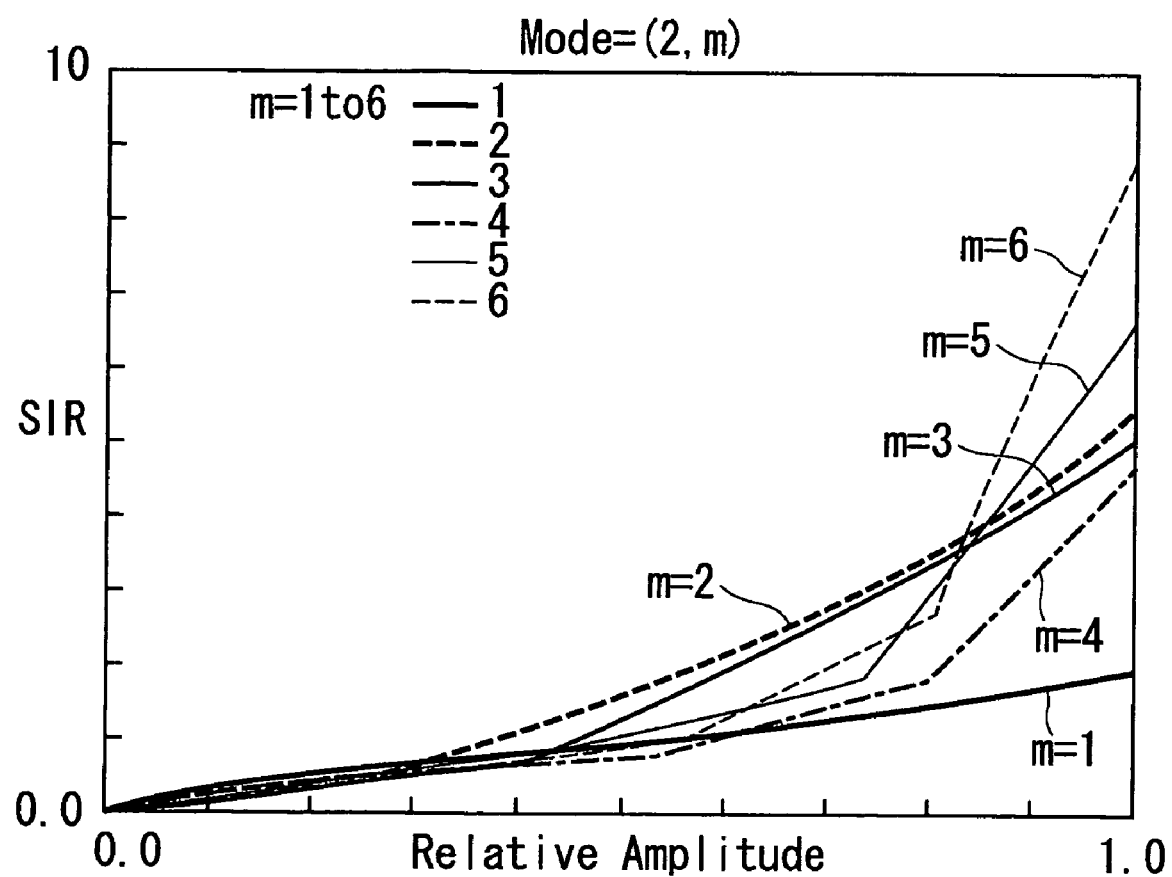
FIG. 29 similarly shows the relation between the standardized vibration amplitude and the sensitivity improve ratio (SIR) when a resonator vibrates in the compound mode, vibration mode n=2, and harmonic vibration order m=1 to 6.
Figure 30:
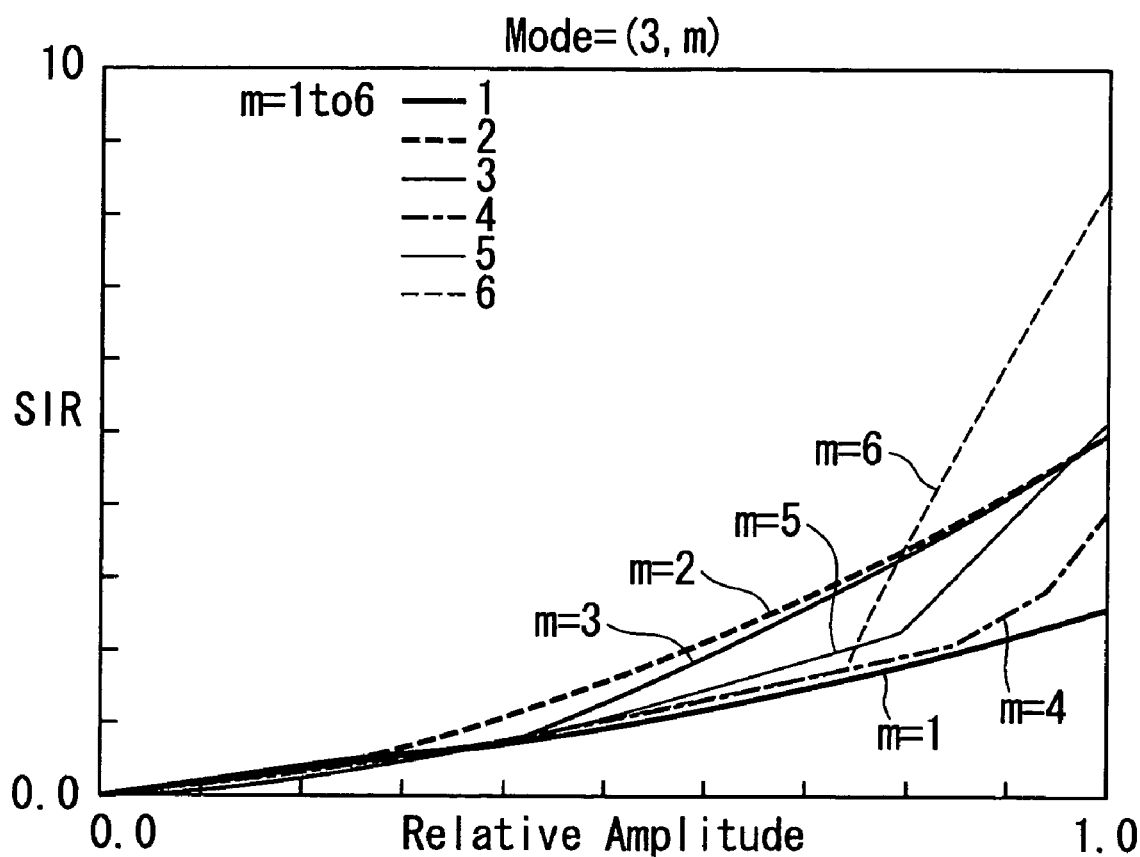
FIG. 30 similarly shows the relation between the standardized vibration amplitude and the sensitivity improve ratio (SIR) when a resonator vibrates in the compound mode, vibration mode n=3, and harmonic vibration order m=1 to 6.
Figure 31:
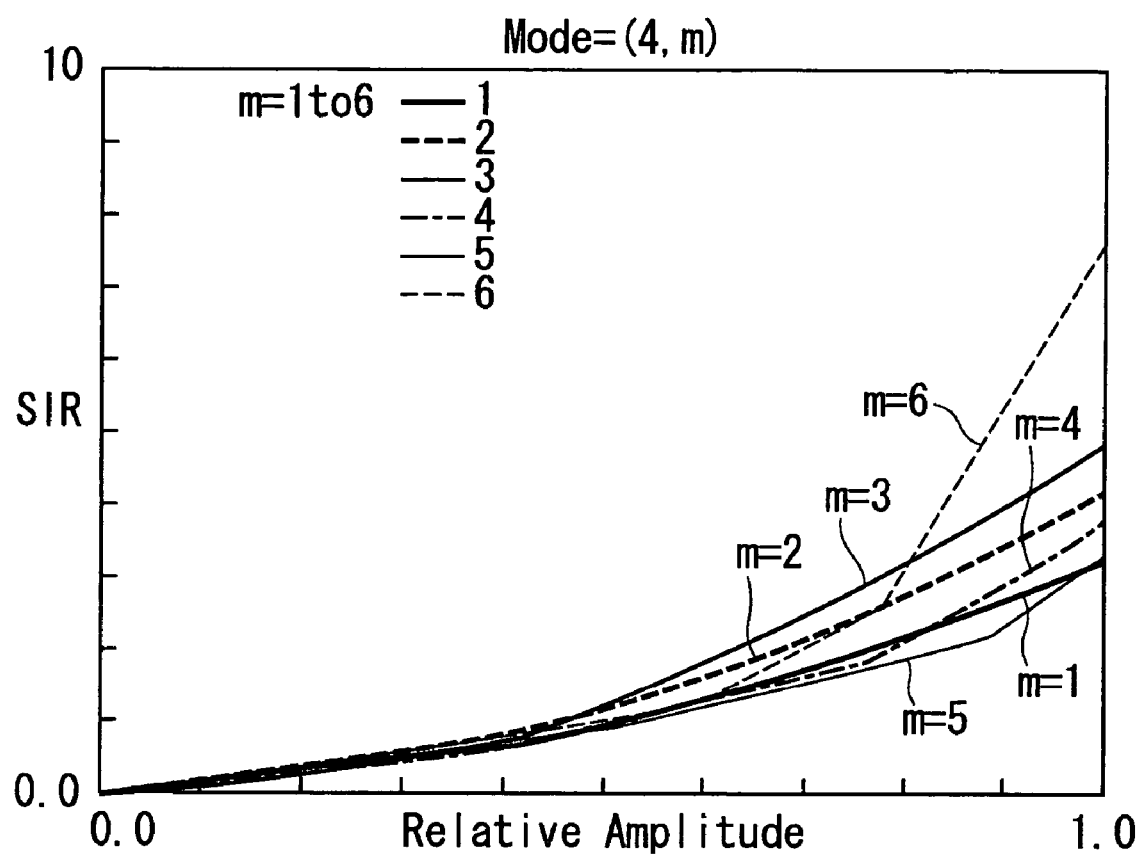
FIG. 31 similarly shows the relation between the standardized vibration amplitude and the sensitivity improve ratio (SIR) when a resonator vibrates in the compound mode, vibration mode n=4, and harmonic vibration order m=1 to 6.

When considering up to secondary nonlinearity, the spectrum shown in FIG. 6 is obtained as an originated spectrum when constituting a transmitter by using the thus-constituted two disc type resonators 20E and 20F for the feedback circuit of an amplifier as in FIG. 5. Moreover, because the disc type resonators 20E and 20F are opposite-phase-connected, two frequencies are clearly separated even if a difference of very-small frequency occurs. Therefore, it is possible to constitute the sensor 10 capable of detecting a very-small mass with very high sensitivity.

As shown in FIG. 37, it is possible to set a frequency tuning mass 31 to the disc type resonators 20E and 20F in order to perform rough frequency adjustment of the disc type resonators 20E and 20F but this is not always necessary. Delicate frequency adjustment by polarization voltage is rather realistic. For example, it is preferable to use a method for observing a frequency change by adjusting two frequencies so as to completely coincide with each other or so that a specific frequency difference is realized and attaching a very-small mass to the disc type resonators 20E and 20F under the above state.

The above third and fourth embodiments are described by using open-end-conditional disc type resonators 20C, 20D, 20E, and 20F. However, the invention is not limited to this, and it is also possible to realize the configuration by using the fixed-end-conditional disc type resonator 20B shown in the second embodiment.

Moreover, when assuming the maximum vibration amplitude as 100% in accordance with the distribution of vibration amplitudes, the resonator is separated into 10 stages every 10% to separate the areas A1 to A10. However, the invention is not limited to this, and it is allowed to properly set an area for detecting a change in vibrations of a resonator due to attachment of a substance within the range of the gist of the present invention.

Furthermore, it is enough that a resonator is the disc type and for example, the resonator can be formed into a shape having a hole at the central portion. This type of the disc type resonator is also referred to as Annular Ring, Hollow-Disk, or RBAR (Radial Bulk Annular Resonator).

Figure 38A:
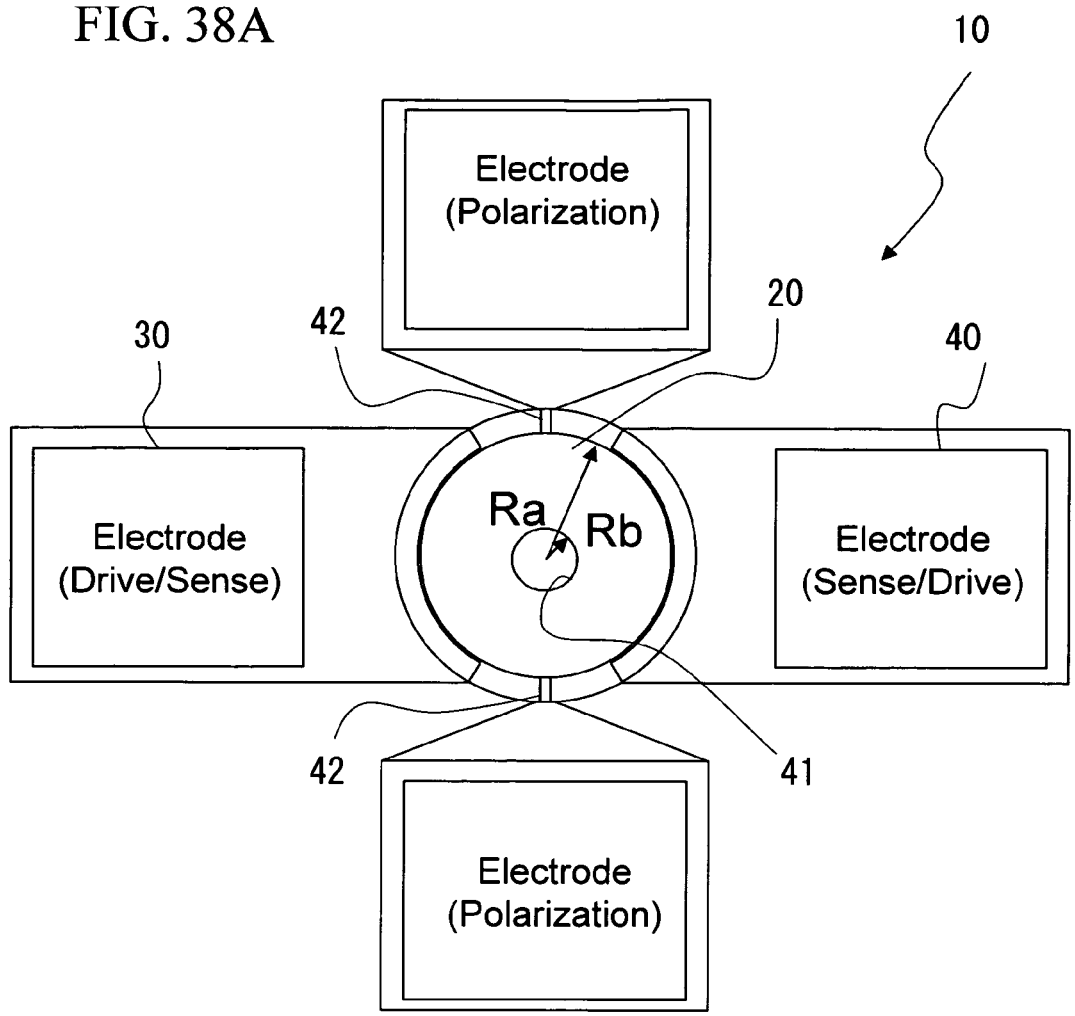
FIG. 38A shows a configuration of a sensor having an opening at the central portion of a disc type resonator and FIG. 38B shows the central portion thereof.
Figure 38B:
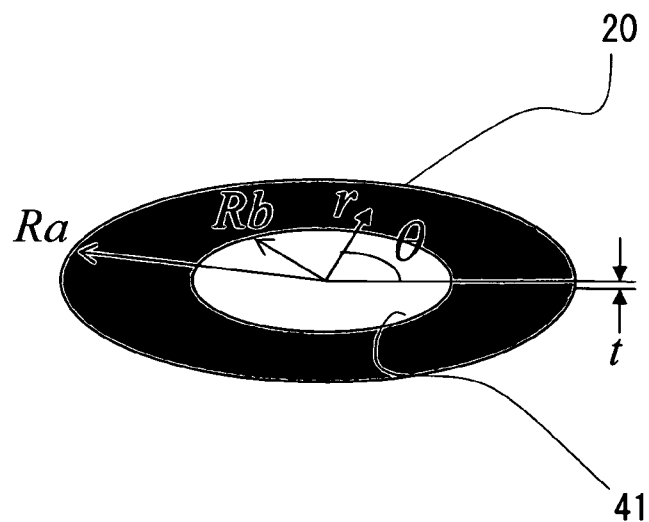

Then, as shown in FIG. 38, a case is described in which an opening 41 is formed at the central portion of a disc type resonator 20 in the sensor 10.

This disc type resonator 20 is supported by only a support member 42 connected to a predetermined position of the outer periphery and remaining other portions are all brought into a free state.

In this case, when assuming the outside diameter of the disc type resonator 20 as Ra and the diameter of the opening 41 as Rb, it is preferable to set the outside diameter Ra of the disc type resonator 20 and the diameter (inside diameter of the disc type resonator 20) Rb of the opening 41 so that Rb/Ra almost satisfies the following condition.

The vibration generated in the disc type resonator 20 includes three modes such as (a) radial mode (mode in which vibration occurs only in diameter direction (r direction), (b) tangential mode (mode in which vibration occurs only in θ direction), and (c) compound mode (mode in which diameter-directional vibration and θ-directional vibration are conjugated.

The determinant of a resonant frequency in the compound mode of the disc type resonator 20 is shown by the following expression (31).

$$f(K) = \begin{vmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{vmatrix} = 0 \quad (31)$$

In this case, $a_{11}$ to $a_{44}$ are shown below.

$$a_{11} = -J_n(K)[(K\xi)^2/2 - n(n+1) + M_n(K)], \; a_{12} = nJ_n(K\xi)[M_n(K\xi) - (n+1)]$$

$$a_{13} = -Y_n(K)[(K\xi)^2/2 - n(n+1) + N_n(K)], \; a_{14} = nY_n(K\xi)[N_n(K\xi) - (n+1)]$$

$$a_{21} = -J_n(L)[(L\xi)^2/2 - n(n+1) + M_n(L)], \; a_{22} = nJ_n(L\xi)[M_n(L\xi) - (n+1)]$$

$$a_{23} = -Y_n(L)[(L\xi)^2/2 - n(n+1) + N_n(L)], \; a_{24} = nY_n(L\xi)[N_n(L\xi) - (n+1)] \quad (32)$$

$$a_{31} = -nJ_n(K)[M_n(K) - (n+1)], \; a_{32} = J_n(K\xi)[(K\xi)^2/2 - n(n+1) + M_n(K\xi)]$$

$$a_{33} = -nY_n(K)[N_n(K) - (n+1)], \; a_{34} = Y_n(K\xi)[(K\xi)^2/2 - n(n+1) + N_n(K\xi)]$$

$$a_{41} = -nJ_n(L)[M_n(L) - (n+1)], \; a_{42} = J_n(L\xi)[(L\xi)^2/2 - n(n+1) + M_n(L\xi)]$$

$$a_{43} = -nY_n(L)[N_n(L) - (n+1)], \; a_{44} = Y_n(L\xi)[(L\xi)^2/2 - n(n+1) + N_n(L\xi)]$$

However, $$K = hR_a, \; L = hR_b, \; M_n(x) = xJ_{n-1}(x)/J_n(x), \; N_n(x) = xY_{n-1}(x)/Y_n(x)$$

$$\xi = \sqrt{2/(1-\sigma)}, \; h = \omega\sqrt{\rho(1-(1-\sigma^2)/E}$$

In this case, σ: Poisson's ratio of resonator material, E: Young's ratio of resonator material, ρ: density of resonator material, and ω: angular frequency ($=2\pi f$)

Two boundaries of the disc type resonator 20 having the opening 41, that is, outside-diameter portion and inside-diameter portion have free-free condition. Therefore, the remaining stress in the radial direction and the remaining stress in the tangential direction are eliminated and thereby, four boundary conditions are determined. Moreover, the displacement U(r,θ) in the radial direction and the displacement V(r,θ) in the tangential direction can be shown by the following expressions.

$$U(r,\theta) = \begin{bmatrix} A_5 \frac{\partial}{\partial r} J_n(hr) + A_6 \frac{n}{r} J_n(kr) + \\ A_7 \frac{\partial}{\partial r} Y_n(hr) + A_8 \frac{n}{r} Y_n(kr) \end{bmatrix} \cos n\theta \quad (33)$$

$$V(r,\theta) = \begin{bmatrix} A_5 \frac{n}{r} J_n(hr) + A_6 \frac{\partial}{\partial r} J_n(kr) + \\ A_7 \frac{n}{r} Y_n(hr) + A_8 \frac{\partial}{\partial r} Y_n(kr) \end{bmatrix} \sin n\theta$$

In this case, $$h = \omega\sqrt{\frac{\rho(1-\sigma^2)}{E}},$$

-continued $$k = \omega\sqrt{\frac{\rho(2+2\sigma)}{E}},$$

$$k = h\sqrt{\frac{2}{1-\sigma}}$$

Then, by applying the above-described four boundary conditions to the expression (33), the following relational expression is obtained.

$$\begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} A_5 \\ A_6 \\ A_7 \\ A_8 \end{bmatrix} = 0 \quad (34)$$

Moreover, the determinant of the resonant frequency in expression (3) denotes that expression (34) is effected in any one of A5, A6, A7, and A8. In the case of this expression (3), determinant=0 of 4×4 matrix of expression (34) becomes a condition. This is expression (3) for determining a resonant frequency.

Coefficients A5, A6, A7, and A8 of expression (33) which is a mode function are undetermined. If they are undetermined, vibration state of the disc type resonator 20 is not fixed. In addition, when these coefficients at the time of resonance are not determined, the coefficients A5, A6, A7, and A8 are undetermined because expression (34) is effected for any one of A5, A6, A7, and A8 in the case of a resonant condition and they cannot be determined. However, by releasing the matrix of expression (34) into a linear expression and showing it, expression (35) is obtained.

$$a_{11}A_5 + a_{12}A_6 + a_{13}A_7 + a_{14}A_8 = 0$$

$$a_{21}A_5 + a_{22}A_6 + a_{23}A_7 + a_{24}A_8 = 0$$

$$a_{31}A_5 + a_{32}A_6 + a_{33}A_7 + a_{34}A_8 = 0$$

$$a_{41}A_5 + a_{42}A_6 + a_{43}A_7 + a_{44}A_8 = 0 \quad (35)$$

By fetching three optional expressions out of four linear expression of expression (34) thus obtained, it is possible to obtain a coefficient as a ratio to any one of the coefficients A5, A6, A7, and A8. For example, by fetching the above three expressions out of expression (35) and dividing them by A5, simultaneous linear equations shown in expression (36) is obtained.

$$a_{11} + a_{12}\frac{A_6}{A_5} + a_{13}\frac{A_7}{A_5} + a_{14}\frac{A_8}{A_5} = 0 \quad (36)$$

$$a_{21} + a_{22}\frac{A_6}{A_5} + a_{23}\frac{A_7}{A_5} + a_{24}\frac{A_8}{A_5} = 0$$

$$a_{31} + a_{32}\frac{A_6}{A_5} + a_{33}\frac{A_7}{A_5} + a_{34}\frac{A_8}{A_5} = 0$$

It is possible to obtain coefficient ratios A6/A5, A7/A5, and A8/A5 respectively using A5 as a denominator from expression (36). By substituting the result for expression (33), radial-directional and tangential-directional displacements at the time of resonance, that is, all mode functions can be determined. In this case, though the above three expressions in expression (35) are used, it is similarly possible to obtain the result using three different expressions selected at random. In this case, four simultaneous linear equations are obtained but obtained results are the same.

Because all equations are proportional to A5, a mode function is not substantially changed even if A5=1 is set. Therefore, by newly setting A5=1 and showing the radial-directional r component in each mode as U(r) and the tangential-directional r component in each mode as V(r), the mode function of expression (33) is shown by the following expression (37).

$$U(r,\theta) = U(r)\cos n\theta$$

$$V(r,\theta) = V(r)\sin n\theta \quad (37)$$

In this case, U(r) and V(r) are shown by the following expression (38).

$$U(r) = \frac{\partial}{\partial r}J_n(hr) + A_6\frac{n}{r}J_n(kr) + A_7\frac{\partial}{\partial r}Y_n(hr) + A_8\frac{n}{r}Y_n(kr) \quad (38)$$

$$V(r) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)$$

This analysis is performed for the circular disc type resonator 20 having the opening 41 differently from a normal disc type resonator. In the case of the disc type resonator 20, U(r) and V(r) shown by expression (38) are greatly changed depending on the ratio between the outside diameter Ra and the inside diameter Rb of the disc type resonator 20. When the ratio between the outside diameter Ra and the inside diameter Rb of the disc type resonator 20 becomes a specific value, U(r) or V(r) may become 0.

For example, in the case of the outside diameter Ra of the disc type resonator 20, when U(Ra)=0, the vibration at the outside-diameter portion of the disc type resonator 20 disappears. Therefore, the outside-diameter portion of the disc type resonator 20 is supported by the support member 42.

In this case, even if V(Ra) is not equal to 0, because the tangential-directional displacement is obtained by multiplying V(Ra) by sin(nθ), vibration does not occur in V(r,θ) of expression (37) at a position where sin(nθ) becomes 0. In the case of the vibration mode of n=1, by holding the disc type resonator 20 by the support member 42 at positions of V(Ra, 0) and V(Ra,π), the vibration energy of the disc type resonator 20 is not lost through the support member 42.

In contrast, when V(Ra) is equal to 0, it is preferable to hold the disc type resonator 20 at a position where cos(nθ) is equal to 0 because the radial-directional displacement is obtained by multiplying U(Ra) by cos(nθ) even if U(Ra) is not equal to 0.

A method for holding the perforated disc type resonator 20 at its outside diameter has been described. However, even when holding the disc type resonator 20 at the inside diameter, it is possible to determine the position in accordance with the same idea.

FIGS. 39 to 41 are illustrations for respectively showing r component in each vibration mode from n=1 to n=3, that is, the state of fluctuations of U(r) and V(r) shown in expression (38) by using the ratio Rb/Ra between the inside diameter Rb and outside diameter Ra as the axis of abscissa. In this case, by assuming Si single crystal as the material of the disc type resonator 20, Poisson's ratio is set to σ=0.28. Moreover, n denotes the mode number of vibration modes and m denotes the order of higher-harmonic vibration.

FIGS. 39 to 41 respectively show from the lowest resonant frequency (m=1) to the fourth resonant frequency (m=4) in each mode and show them as (n,m) in accordance with the normal mode expression.

Figure 39A:
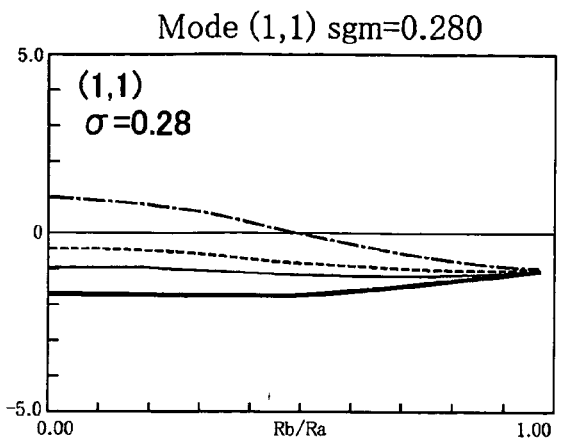
FIGS. 39A to 39D show the relation between the ratio of the outside diameter and inside diameter of a disc type resonator and values of U(Ra), U(Rb), V(Ra), and V(Rb) in n=1 mode.
Figure 39B:
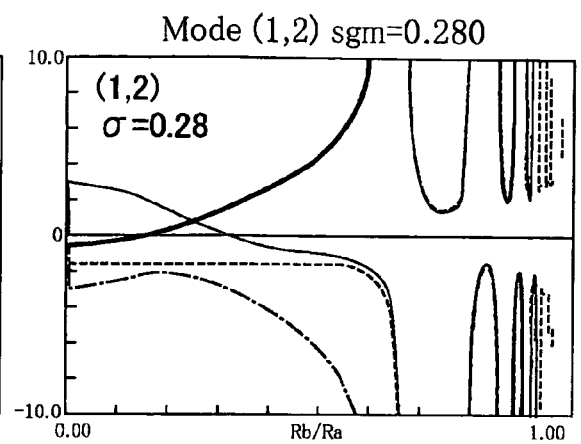
Figure 39C:
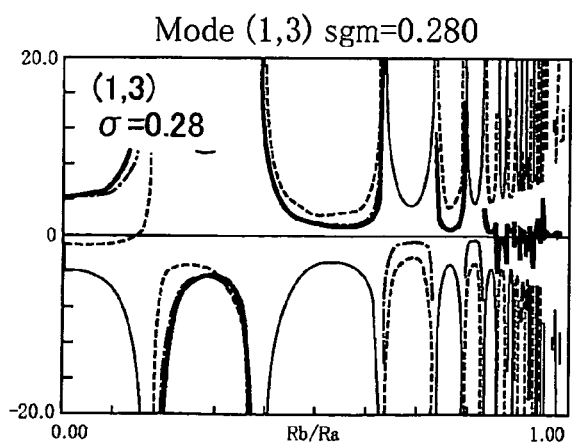
Figure 39D:
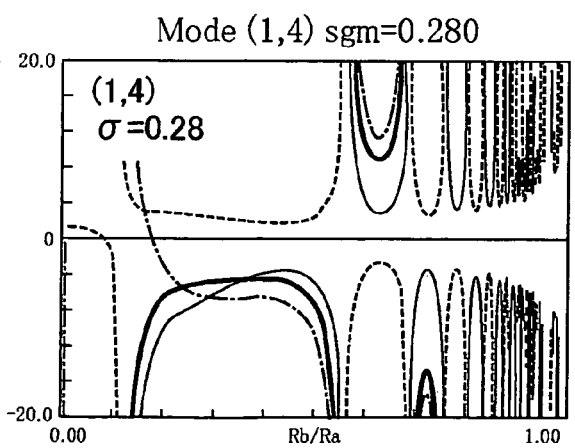
Figure 40A:
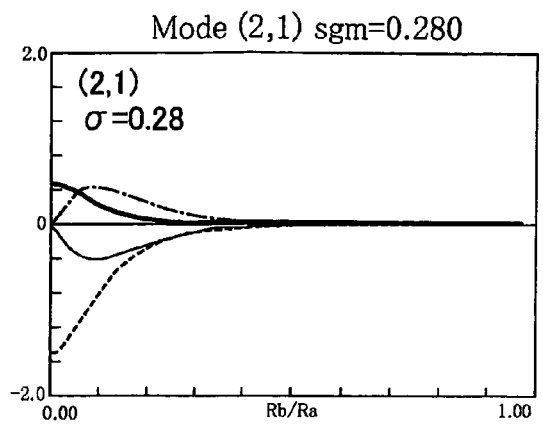
FIGS. 40A to 40D show the relation between the ratio of the outside diameter and inside diameter of a disc type resonator and values of U(Ra), U(Rb), V(Ra), and V(Rb) in n=2 mode.
Figure 40B:
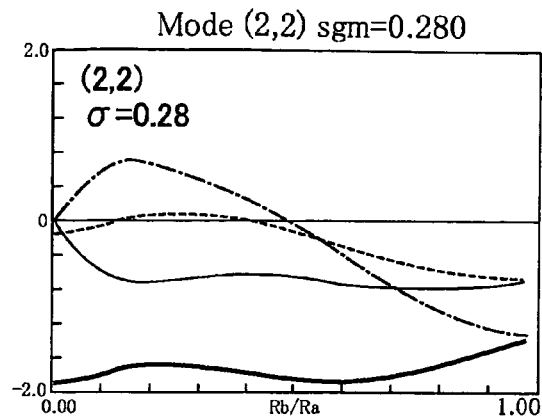
Figure 40C:
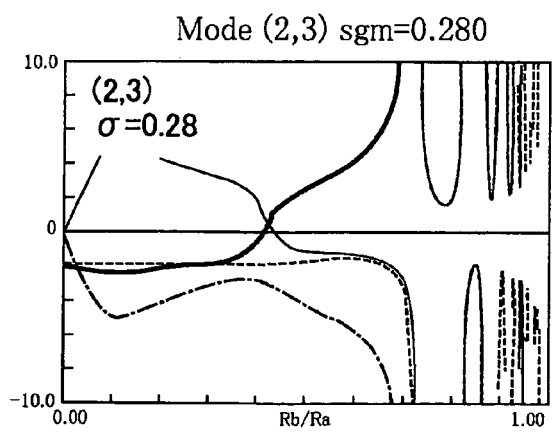
Figure 40D:
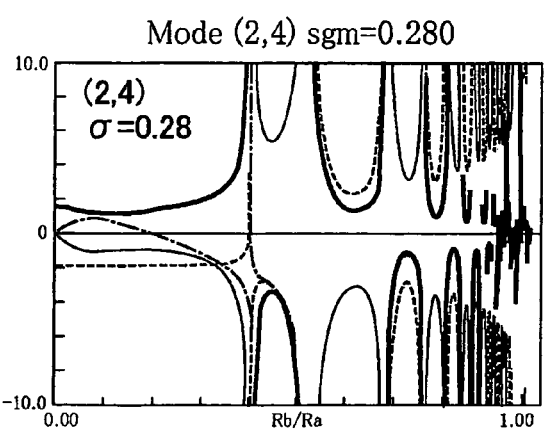
Figure 41A:
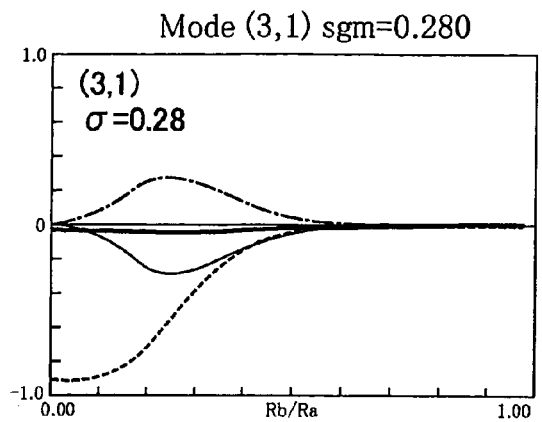
FIGS. 41A to 41D show the relation between the ratio of the outside diameter and inside diameter of a disc type resonator and values of U(Ra) U(Rb), V(Ra), and V(Rb) in n=3 mode.
Figure 41B:
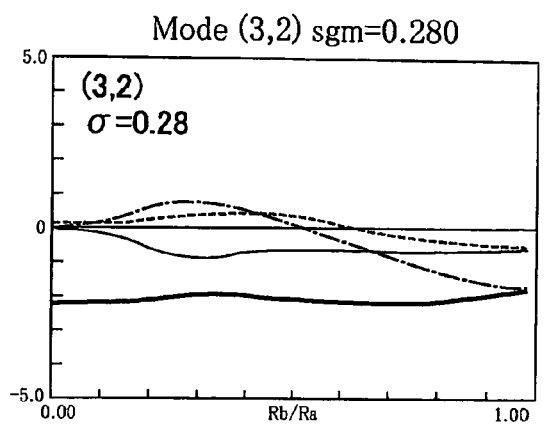
Figure 41C:
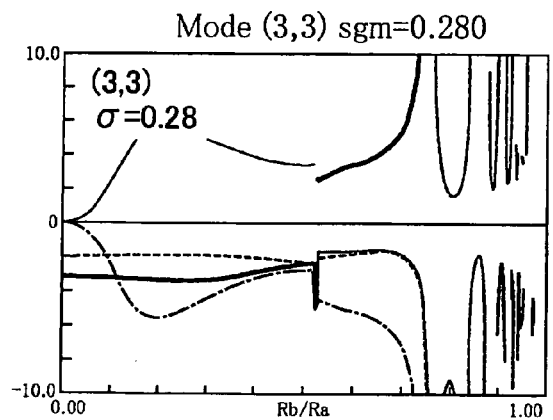
Figure 41D:
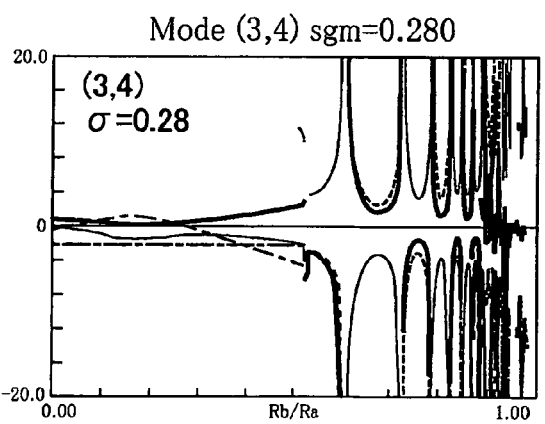
Figure 42A:
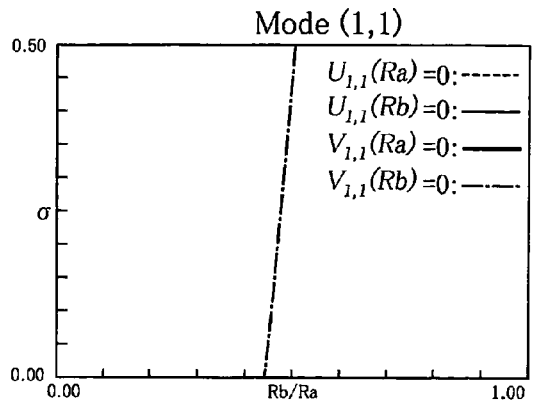
FIGS. 42A to 42D show the relation between the ratio of the outside diameter and inside diameter of a disc type resonator when expression (12) is effected and the Poisson's ratio in n=1 mode.
Figure 42B:
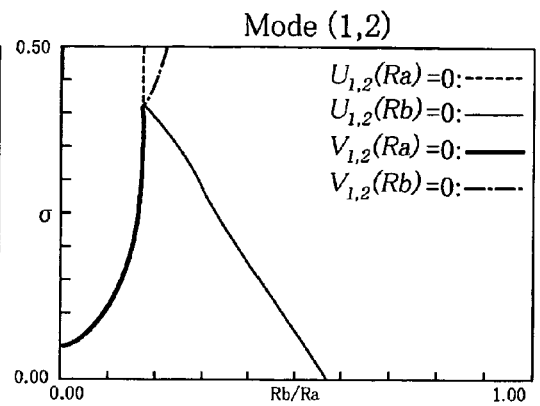
Figure 42C:
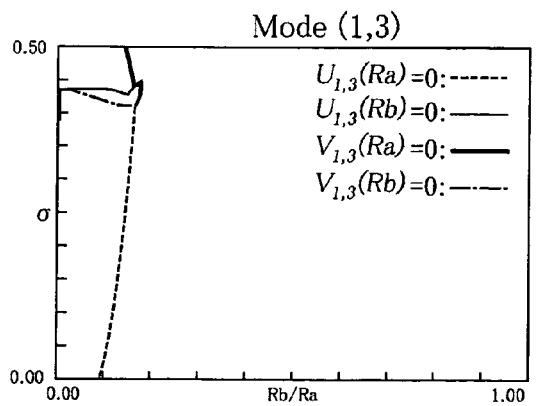
Figure 42D:
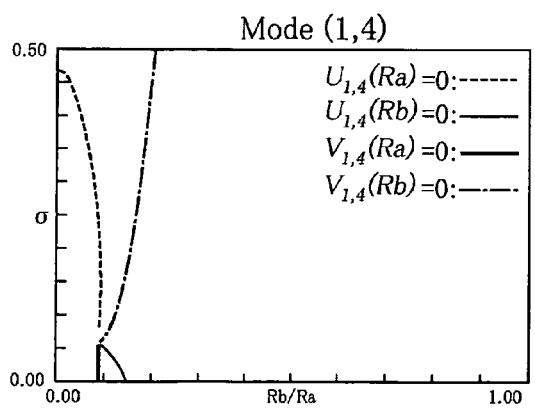
Figure 43A:
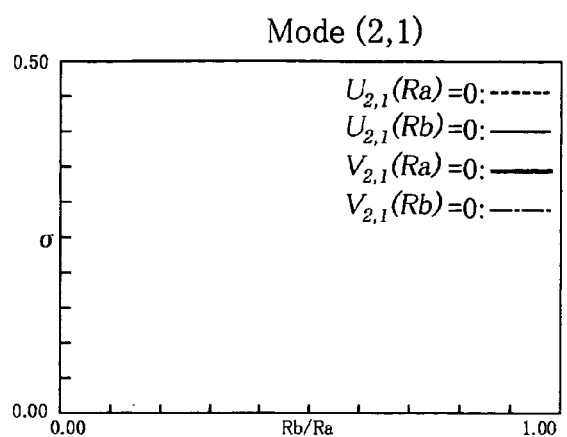
FIGS. 43A to 43D show the relation between the ratio of the outside diameter and inside diameter of a disc type resonator when expression (12) is effected and the Poisson's ratio in n=2 mode.
Figure 43B:
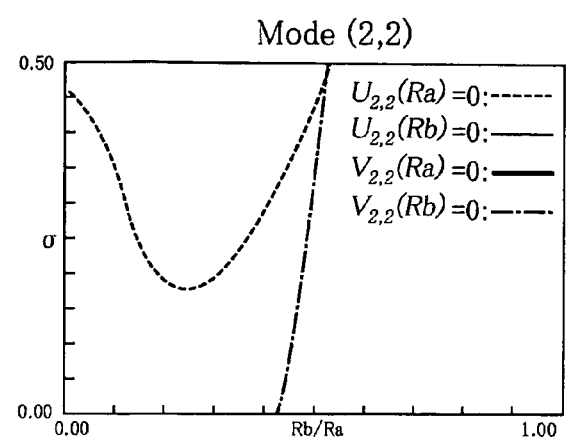
Figure 43C:
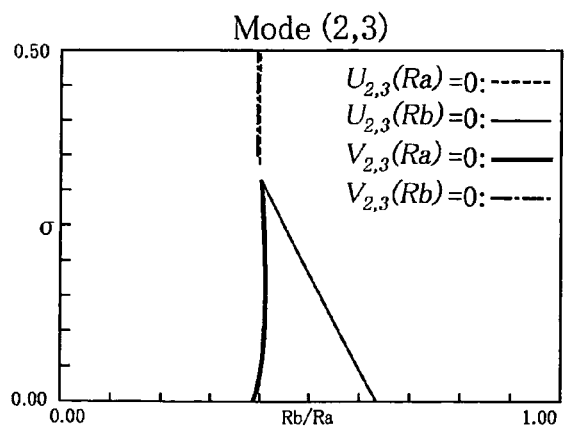
Figure 43D:
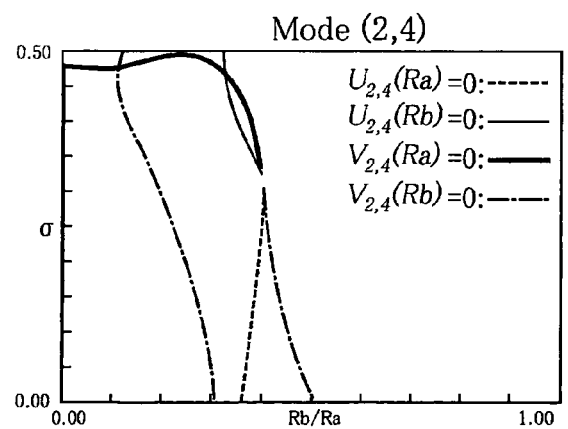
Figure 44A:
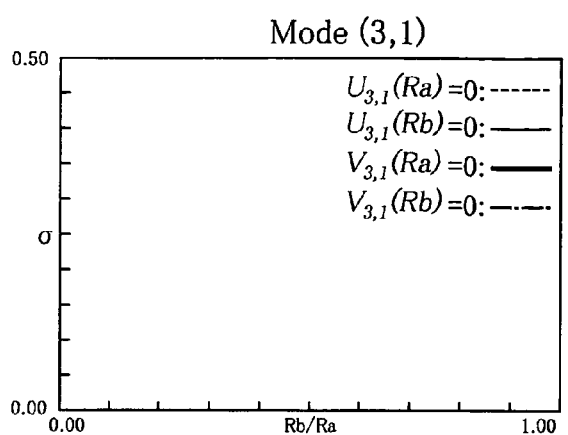
FIGS. 44A to 44D show the relation between the ratio of the outside diameter and inside diameter of a disc type resonator when expression (12) is effected and the Poisson's ratio in n=3 mode.
Figure 44B:
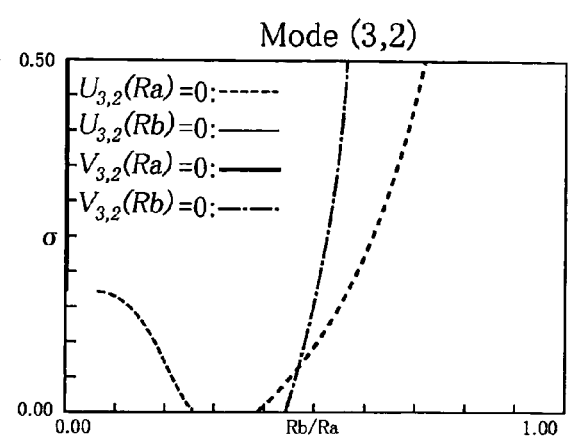
Figure 44C:
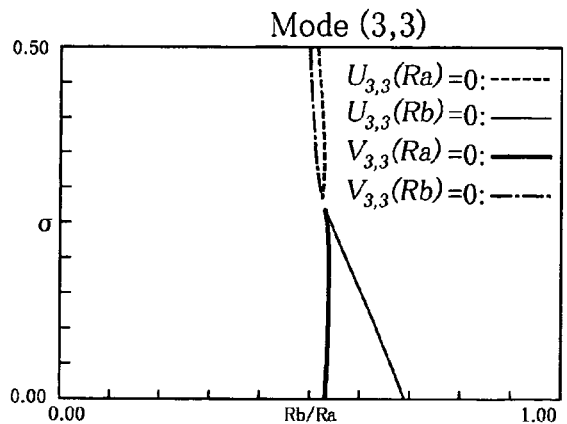
Figure 44D:
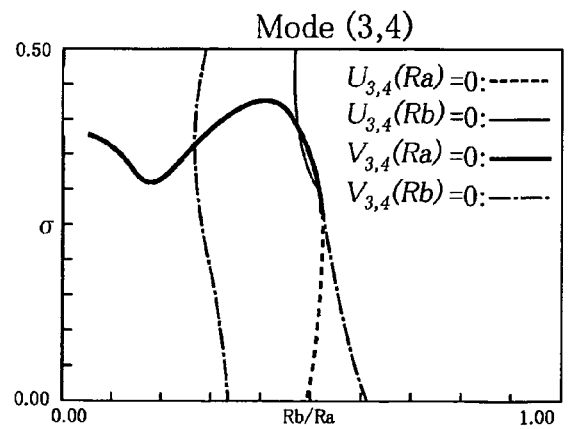

In FIGS. 39 to 41, it is observed that any one of U(Ra), U(Rb), V(Ra), and V(Rb) becomes 0 at proper Rb/Ra except the (2,1) mode in FIG. 40A and the (3,1) mode in FIG. 41A.

For example, in the case of the (1,2) mode shown in FIG. 39B, it is shown that V(Ra) becomes 0 at Rb/Ra=0.17. Therefore, to design the disc type resonator 20 used for the (1,2) mode by using a material having a Poisson's ratio of 0.28 (for example, single crystal Si), by selecting the ratio between inside diameter Rb and outside diameter Ra as 0.17 so as to hold the disc type resonator 20 at an angle of cos θ=0, that is, by the inside-diameter portion at the position of θ=±π/2, it is possible to hold the disc type resonator 20 without influencing the resonant vibration of the disc type resonator 20.

That is, in the case of the disc type resonator 20 having an outside diameter of 100 μm used for the (1,2) mode, when setting the diameter of the opening 41 to 17 μm whereas Rb/Ra becomes 0.17, the tangential-directional vibration at the outside-diameter portion of the disc type resonator 20 becomes 0. Moreover, in this case, by supporting the disc type resonator 20 at an angle of cos θ=0 at the outside-diameter portion of the opening 41, that is, the position of θ=±π/2, it is possible to realize a method for holding the disc type resonator 20 without influencing resonant vibration.

By the way, in the case of a material having Poisson' ratio of σ=0 to σ=0.5, when U(Ra), U(Rb), V(Ra), and V(Rb) become 0, it is very important to examine that the above phenomenon occurs in any Rb/Ra. Therefore, combinations of Rb/Ra with Poisson's ratio σ holding the following expression (39) are examined from expression (38) on modes (n=1-3 and m=1-4).

$$U(Ra) = \frac{\partial}{\partial r}J_n(hr) + A_6\frac{n}{r}J_n(kr) + A_7\frac{\partial}{\partial r}Y_n(hr) + A_8\frac{n}{r}Y_n(kr)|_{r=Ra} = 0 \quad (39)$$

$$U(Rb) = \frac{\partial}{\partial r}J_n(hr) + A_6\frac{n}{r}J_n(kr) + A_7\frac{\partial}{\partial r}Y_n(hr) + A_8\frac{n}{r}Y_n(kr)|_{r=Rb} = 0$$

$$V(Ra) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)|_{r=Ra} = 0$$

$$V(Rb) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)|_{r=Rb} = 0$$

FIGS. 42 to 44 show the examination results.

By using only Poisson' ratio as a variable, this denotes that all materials are examined because h and k have a relation of $k=h(2/(1-\sigma))^{1/2}$ and when assuming h and k as variables, two these variables are related only by the Poisson' ratio σ from expression (33).

FIGS. 42 to 44 show relations between the Poisson's ratio σ (axis of ordinate) satisfying expression (39) in modes of n=1 to 3 and m=1 to 4 and the ratio Rb/Ra (axis of abscissa) between the inside diameter Rb and the outside diameter Ra of the disc type resonator 20. That is, when the Poisson's ratio of a resonator material is known, it is possible to determine a vibration mode and a position for holding the disc type resonator 20 and the ratio between the inside diameter Rb and outside diameter Ra of the disc type resonator 20 from the relations in FIGS. 42 to 44. A resonant frequency is determined by changing the size, that is, outside diameter Ra of the disc type resonator 20.

Thus, by previously knowing the relations in FIGS. 42 to 44, it is possible to realize the high-performance disc type resonator 20 from which vibration energy does not escape through a holding portion.

In the case of the disc type resonator 20 used by vibrating it in the tangential direction, the support member 42 preferably has the length $L_R$ shown by expression (40). When adopting a driving method using the piezoelectric effect for a driving source (not illustrated), the disc type resonator 20 is used by vibrating it in the tangential direction. In this case, it is preferable to set the length of the support member 42 to $L_R$ shown by expression (40).

$$K = \frac{10(1+\sigma)}{12+11\sigma} \quad (40)$$

Moreover, in the case of the disc type resonator 20 used by vibrating it in the radial direction, the support member 42 preferably has the length $L_S$ shown by expression (41).

$$L_s = \frac{n_m\pi}{2\omega}\sqrt{\frac{KE}{\rho(2+2\sigma)}}, \quad (41)$$

$$n_m = 1, 3, 5 \ldots$$

However, $$K = \frac{10(1+\sigma)}{12+11\sigma}$$

Thus, by properly selecting the ratio Rb/Ra between the inside diameter Rb and outside diameter Ra of the disc type resonator 20, r component of radial-directional displacement, that is, U(Ra) or U(Rb) and r component of tangential-directional displacement, that is, V(Ra) or V(Rb) may become 0. By using a specific phenomenon particular to the disc type resonator 20 having the opening 41 under this shape, it is possible to hold the disc type resonator 20 without influencing the resonant vibration of the disc type resonator 20 and provide the disc type resonator 20 having a very high Q. Thereby, the sensor 10 can detect a substance having a mass and the mass with high sensitivity. Moreover, because the disc type resonator 20 can be fabricated by MEMS technique by using Si single crystal as a structural material, it is possible to build the sensor 10 in the same chip as a Si semiconductor.

An example of the disc type resonator 20 using Si single crystal (Poisson's ratio σ=0.28) is shown as the material of the resonator. However, it is a matter of course that the outside diameter Ra of the disc type resonator 20, inside diameter Rb of the opening 41, and support position by the support member 42 of the disc type vibrator 20 can be selected by performing the same study for other materials.

Moreover, it is possible to select the configuration used for the above embodiment or properly modify the configuration to another configuration as long as it is not deviated from the gist of the present invention.

According to the present invention, it is possible to change a detection sensor and resonator to high sensitivity, compact size, low price, and high accuracy. Moreover, it is possible to hold a resonator when there is no vibration component of the disc type resonator and provide a high-quality detection sensor having a high Q value.

What is claimed is:

1. A detection sensor comprising:
   a disc type mechanical resonator whose vibration characteristic is changed due to attachment or adsorption of a substance having a mass;
   a driving unit that vibrates the resonator; and
   a detection unit that detects the substance by detecting a change in vibrations of the resonator, wherein
   the driving unit and the detection unit are spaced apart from the resonator,
   the driving unit and the detection unit detect the vibration of the resonator and a change in vibrations of the resonator by electrostatically coupling with the resonator, and the resonator vibrates only in the in-disc-face direction of the resonator.

2. The detection sensor according to claim 1, wherein the substance is attached to the surface of the resonator.

3. The detection sensor according to claim 1, wherein the resonator has an adsorbing member that adsorbs the substance.

4. The detection sensor according to claim 1, wherein irregularity or a groove is formed on at least a part of the surface of the resonator.

5. The detection sensor according to claim 1, wherein the detection unit detects the quantity of the substance attached to the resonator.

6. The detection sensor according to claim 1, wherein the substance is a specific molecular or a plurality of types of molecules respectively having a specific characteristic or feature.

7. The detection sensor according to claim 1, wherein a plurality of the resonators are provided and one of the resonators and the other of the resonators are electrostatically coupled with each other, and
   the detection unit detects attachment of the substance to the resonators by detecting a change in the difference between vibration frequencies when the substance attaches to the one-hand resonator and the other-hand resonator.

8. The detection sensor according to claim 1, wherein the resonator is supported only at a peripheral portion of the resonator.

9. The detection sensor according to claim 1, wherein the vibration generated in the resonator has the following three modes: (a) radial mode (mode in which it vibrates only in the diameter direction), (b) tangential mode (mode in which it vibrates only in θ direction), and (c) compound mode (mode in which diameter-directional vibration and θ-directional vibration are conjugated).

10. The detection sensor according to claim 1, wherein the resonator uses single-crystal or polycrystalline Si as a structural material.

11. The detection sensor according to claim 1, wherein a reference resonator to which the substance does not attach is provided in parallel with the resonator, and
    the detection unit detects attachment of the substance to the resonator by detecting a change in vibrations of the resonator on the basis of the vibration of the reference resonator when the substance attaches to the resonator.

12. The detection sensor according to claim 11, wherein reverse phase vibration is generated in the resonator and the reference resonator.

13. The detection sensor according to claim 1, wherein the detection unit detects a change in vibrations of the resonator due to the substance directly or indirectly attached or adsorbed to an area on the surface of the resonator.

14. The detection sensor according to claim 13, wherein the area is a portion where the vibration amplitude of the resonator becomes 50% or more with respect to the maximum vibration amplitude of the resonator.

15. The detection sensor according to claim 13, wherein the area includes a portion where the vibration amplitude of the resonator is maximized.

16. The detection sensor according to claim 13, wherein a plurality of the areas are set and substances different from each other are attached or adsorbed to the areas.

17. The detection sensor according to claim 1, wherein the resonator is annular in which the outside diameter is Ra and the inside diameter is Rb because an opening is formed at the central portion, and
    the resonator is formed by the outside diameter Ra and the inside diameter Rb almost satisfying the radial-directional displacement U(r)=0 or tangential-directional displacement V(r)=0 when r=Ra or Rb, providing that the resonator vibrates on the positional coordinates (r, Θ), and the U(r) and V(r) at the position r are shown by expression (42).

$$U(r) = \frac{\partial}{\partial r}J_n(hr) + A_6 \frac{n}{r}J_n(kr) + A_7 \frac{\partial}{\partial r}Y_n(hr) + A_8 \frac{n}{r}Y_n(kr) \quad (42)$$

$$V(r) = \frac{n}{r}J_n(hr) + A_6 \frac{\partial}{\partial r}J_n(kr) + A_7 \frac{n}{r}Y_n(hr) + A_8 \frac{\partial}{\partial r}Y_n(kr)$$

In this case, $$h = \omega\sqrt{\frac{\rho(1-\sigma^2)}{E}},$$

$$k = \omega\sqrt{\frac{\rho(2+2\sigma)}{E}},$$

$$k = h\sqrt{\frac{2}{1-\sigma}}$$

σ: Poisson's ratio of resonator material, E: Young's modulus of resonator material, ρ: density of resonator material, ω: angular frequency, n: order of vibration mode, A6, A7, and A8: constants uniquely determined in accordance with specific vibration mode specified by outside diameter and inside diameter of resonator, Young's modulus, density and Poisson's ratio of resonator material, and boundary condition of resonator (in this case, free-free condition).

18. The detection sensor according to claim 17, wherein when r=Ra in the above expression (42) and U(r)=0 or V(r)=0 is almost satisfied, the resonator is supported by the outside diameter portion.

19. The detection sensor according to claim 17, wherein when r=Rb in the above expression (42) and U(r)=0 or V(r)=0 is almost satisfied, the resonator is supported by the inside diameter portion.

20. The detection sensor according to claim 18 or 19, wherein
    when r=Ra or Rb in the above expression (42) and U(r)=0 is almost satisfied, the resonator is supported at a position Θ of sin(nΘ)=0.

21. The detection sensor according to claim 18 or 19, wherein
    when r=Ra or Rb in the above expression (42) and V(r)=0 is almost satisfied, the resonator is supported at a position Θ of cos(nΘ)=0.

* * * * *